US007888064B2

(12) United States Patent
Berger et al.

(10) Patent No.: US 7,888,064 B2
(45) Date of Patent: Feb. 15, 2011

(54) GRAM POSITIVE BACTERIAL CELLS COMPRISING A DISRUPTED FLAGELLIN GENE, FLAGELLIN-BASED FUSION PROTEINS AND USE IN REMOVAL OF METAL IONS FROM A LIQUID

(75) Inventors: Eldie Berger, Pretoria (ZA); Maureen Elizabeth Louw, Pretoria (ZA); Michael Craig Crampton, Garsfontein East (ZA)

(73) Assignee: CSIR, Scientia, Pretoria (ZA)

( * ) Notice: Subject to any disclaimer, the term of this patent is extended or adjusted under 35 U.S.C. 154(b) by 848 days.

(21) Appl. No.: 11/792,242

(22) PCT Filed: Dec. 2, 2005

(86) PCT No.: PCT/IB2005/054022

§ 371 (c)(1),
(2), (4) Date: Jun. 1, 2007

(87) PCT Pub. No.: WO2006/072845

PCT Pub. Date: Jul. 13, 2006

(65) Prior Publication Data

US 2008/0003237 A1    Jan. 3, 2008

(30) Foreign Application Priority Data

Dec. 2, 2004    (ZA) .................................. 2004/9786

(51) Int. Cl.
  C12P 21/06    (2006.01)
  C07K 14/001    (2006.01)
(52) U.S. Cl. ................... 435/69.1; 435/325; 435/252.3; 435/320.1; 536/23.1; 530/350; 514/2
(58) Field of Classification Search .................. None
See application file for complete search history.

(56) References Cited

FOREIGN PATENT DOCUMENTS

| EP | 0 237 045 A2 | 9/1987 |
|---|---|---|
| EP | 1 661 910 A | 5/2006 |
| WO | 87/02385 A | 4/1987 |
| WO | 89/10967 A | 11/1989 |
| WO | 01/92471 A | 12/2001 |
| WO | 03/011487 A | 2/2003 |
| WO | 03/078451 A | 9/2003 |
| WO | 03/094049 A | 11/2003 |
| WO | 2004/080903 A | 9/2004 |

OTHER PUBLICATIONS

Barilla, D., et al; "Coupling of Flagellin Gene Transcription to Flagellar Assembly in *Bacillus subtilis*"; Journal of Bacteriology; Aug. 1994; pp. 4558-4564; vol. 176, No. 15.
Chen, L., et al; "The *Bacillus subtilis* Sigma D-dependent Operon Encoding the Flagellar Proteins FliD, FliS, and FliT"; Journal of Bacteriology; Jun. 1994; pp. 3093-3101; vol. 176, No. 11.
Westerlund-Wikstrom, B., et al; "Peptide Display on Bacterial Flagella: Principles and Applications"; International Journal of Medical Microbiology; pp. 223-230; Jul. 2000; vol. 290; Urban and Fischer Verlag; Germany.
Westerlund-Wikstrom, B., et al; "Functional Expression Of Adhesive Peptides As Fusions To *Escherichia coli* Flagellin"; Protein Engineering; Nov. 1997; pp. 1319-1326; vol. 10, No. 11; Oxford University Press; Surrey, GB.
Thai, Corrine, et al; "Identification and Characterization of Cu(2)O- and ZnO-Binding Polypeptides by *Escherichia coli* Cell Surface Display: Toward an Understanding of Metal Oxide Binding"; Biotechnology and Bioengineering; Jul. 20, 2004; pp. 129-137; vol. 87, No. 2.
Kriplani, Ushma, et al; "Selecting Peptides for Use in Nanoscale Materials Using Phage-Displayed Combinatorial Peptide Libraries"; Current Opinion in Biotechnology; Aug. 2005; pp. 470-475; vol. 16, No. 4.
Takami, Hideto, et al; "Reidentificaton of Facultatively Alkaliphilic Bacillus Sp. C-125 to *Bacillus halodurans*"; Bioscience Biotechnology and Biochemistry; 1999; pp. 943-945; vol. 63, No. 5.
Sakamoto, Yoh-Ichiro, et al; "Analysis of the Flagellin (hag) Gene of Alkalophilic Bacillus Sp. C-125"; Journal of General Microbiology; 1992; pp. 2159-2166; vol. 138, No. 10.
Lavallie, E. R., et al; "Cloning of the Flagellin Gene From *Bacillus subtilis* and Complementation Studies of an In Vitro-Derived Deletion Mutation"; Journal of Bacteriology; Jun. 1989; pp. 3085-3094; vol. 171, No. 6.
Kuwajima, G; "Construction of a Minimum-Size Functional Flagellin of *Escherichia coli*"; Journal of Bacteriology; Jul. 1988; pp. 3305-3309; vol. 170, No. 7.
Eaves-Pyles, T. D., et al; "Salmonella Flagellin-Dependent Proinflammatory Responses Are Localized to the Conserved Amino and Carboxyl Regions of the Protein"; Journal of Immunology; Dec. 15, 2001, pp. 7009-7016; vol. 167, No. 12.
Kobayashi, G., et al.; "Accumulation of an Artificial Cell Wall-binding Lipase by *Bacillus subtilis* wprA and/or sigD Mutants"; FEMS Microbiology Letters; Jul. 15, 2000; pp. 165-169; vol. 188, No. 2.
Mirel, D. B., et al.; "The *Bacillus subtilis* Flagellin Gene (hag) Is Transcribed by the [Sigma] 28 Form of RNA Polymerase"; Journal of Bacteriology; Jun. 1989; pp. 3095-3101; vol. 171, No. 6.

(Continued)

Primary Examiner—Karen Cochrane Carlson
(74) Attorney, Agent, or Firm—Fulwider Patton LLP

(57) ABSTRACT

The invention provides flagellin-based fusion proteins (FBFP) are useful for a variety of purposes, in bioremediation to remove metal ions from a liquid, to express an enzyme or an immunogen, nucleic acids encoding the FBFP, vectors containing the nucleic acids, and host cells harboring the vectors. Furthermore, the invention provides methods for obtaining over-expression and surface display of heterologous polypeptides in Gram-positive bacterial cells in *Bacillus halodurans* in particular. In addition, the invention features gene-disrupted bacterial are useful for expressing the recombinant FBFP on their surfaces. Also included in the invention genetic constructs are useful for making FBFP and methods of using the FBFP.

39 Claims, 20 Drawing Sheets

OTHER PUBLICATIONS

Zuberi, A. R., et al; "Transposon Tn917lacZ Mutagenesis of *Bacillus subtilis*: Identification of Two New Loci Required for Motility and Chemotaxis"; Journal of Bacteriology; Dec. 1990; pp. 6841-6848; vol. 172, No. 12.

Helmann, J. D., et al; "Cloning, Sequencing, and Disruption of the *Bacillus subtilis* [Sigma] 28 Gene"; Journal of Bacteriology; Apr. 1988; pp. 1568-1574; vol. 170, No. 4.

Márquez, L. M., et al; "Studies of [Sigma] D-dependent Functions in *Bacillus subtilis*"; Journal of Bacteriology; Jun. 1990; pp. 3435-3443; vol. 172, No. 6.

Stephenson, K., et al.; "Simultaneous Inactivation of the wprA and dltB Genes of *Bacillus subtilis* Reduces the Yield of [Alpha]-Amylase"; Letters in Applied Microbiology; 2002; pp. 394-397; vol. 34, No. 6.

Margot, P., et al.; "The wprA Gene of *Bacillus subtilis* 168, Expressed During Exponential Growth, Encodes A Cell-Wall-Associated Protease"; Microbiology (1996), 142, pp. 3437-3444.

Yamamoto, Hiroki, et al.; "Localization of the Vegetative Cell Wall Hydrolases LytC, LytE, and LytF on the *Bacillus subtilis* Cell Surface and Stability of These Enzymes to Cell Wall-Bound or Extracellular Proteases"; Journal of Bacteriology; Nov. 2003; pp. 6666-6677; vol. 185, No. 22.

Babe, L. M., et al.; "Purification and Biochemical Analysis of WprA, A 52-kDa Serine Protease Secreted by *B. subtilis* as an Active Complex With Its 23-kDa Propeptide"; Biochimica Et Biophysica Acta; Jul. 28, 1998; pp. 211-219; vol. 1386.

```
B halodurans Alk36:       1  MIINHNLPAANAAYQNGGNQLT  22
                             +++++++++ ++      + +
                             MIINHNLPA NA      G N
Bacillus sp. C-125:  1    1  MIINHNLPAMNAHRNMGINLNQ  22
(hag) gene
```

```
Alk36:  961  atgattatcaatcacaatttaccagcaatgaatgcgcatcgtaacatgggtatcaatctt 1020
             ||||||||||||||||||||||||||||||||||||||||||||||||||||||||||||
C-125:    1  atgattatcaatcacaatttaccagcaatgaatgcgcatcgtaacatgggtatcaatctt   60

Alk36: 1021  aaccaaggtcaagaagcgatggagaagctttcttcaggtcttcgcattaaccgtgcagga 1080
             |||||||||||| |||||||||||||||||||||||||||||||||||||||||||||||
C-125:   61  aaccaaggtcaaaaagcgatggagaagctttcttcaggtcttcgcattaaccgtgcagga  120

Alk36: 1081  gacgatgctgcaggtcttgccatctctgaaaaaatgcgtgcgcaaatccgtggtttggat 1140
             ||||||||||||||||||||||||||||||||||||||||||||||||||||||||||||
C-125:  121  gacgatgctgcaggtcttgccatctctgaaaaaatgcgtgcgcaaatccgtggtttggat  180

Alk36: 1141  caagcgtctcgtaactcacaagacggtatttcgttaattcaaacagctgaaggtgcgctt 1200
             ||||||||||||||||||||||||||||||||||||||||||||||||||||||||||||
C-125:  181  caagcgtctcgtaactcacaagacggtatttcgttaattcaaacagctgaaggtgcgctt  240

Alk36: 1201  gatgaagtacattctattcttcaacgtatgcgtgagctagcggttcaatcttcgaacgaa 1260
             ||||||||||||||||||||||||||||||||||||||||||||||||||||||||||||
C-125:  241  gatgaagtacattctattcttcaacgtatgcgtgagctagcggttcaatcttcgaacgaa  300

Alk36: 1261  acgaatgttgagcaagatcaagcagctcttaacgatgaattccaacaattagttgaggaa 1320
             ||||||||||||||||||||||||||||||||||||||||||||||||||||||||||||
C-125:  301  acgaatgttgagcaagatcaagcagctcttaacgatgaattccaacaattagttgaggaa  360

Alk36: 1321  attgaaagaatcaaagatacaactcaatttaatacgcaaaaattactcgatgatacagta 1380
             ||||||||||||||||||||||||||||||||||||||||||||||||||||||||||||
C-125:  361  attgaaagaatcaaagatacaactcaatttaatacgcaaaaattactcgatgatacagta  420

ALk36: 1381  gatactgtacaacttcaagttggtgctaattctggtgaattaattgaacttgatttaaca 1440
             ||||||||||||||||||||||||||||||||||||||||||||||||||||||||||||
C-125:  421  gatactgtacaacttcaagttggtgctaattctggtgaattaattgaacttgatttaaca  480

Alk36: 1441  aaagttgatttatcagctatccatacagctttggcggctgaggatattactgaccacact 1500
             ||||||||||||||||||||||||||||||||||||||||||||||||||||||||||||
C-125:  481  aaagttgatttatcagctatccatacagctttggcggctgaggatattactgaccacact  540

Alk36: 1501  aatgcacaatcagctattgacgctattgatgagcaattaaaagctgtttcagaaggtcgc 1560
             ||||||||||||||||||||||||||||||||||||||||||||||||||||||||||||
C-125:  541  aatgcacaatcagctattgacgctattgatgagcaattaaaagctgtttcagaaggtcgc  600

Alk36: 1561  tcttacctaggagctatgcaaaaccgcctagagcatacaatcaaaaaccttgataatgct 1620
             ||||||||||||||||||||||||||||||||||||||||||||||||||||||||||||
C-125:  601  tcttacctaggagctatgcaaaaccgcctagagcatacaatcaaaaaccttgataatgct  660

Alk36: 1621  tctgaaaaccttcaagctgctgagtctcgtatccgtgacgtagacatggcgaaagaaatg 1680
             ||||||||||||||||||||||||||||||||||||||||||||||||||||||||||||
C-125:  661  tctgaaaaccttcaagctgctgagtctcgtatccgtgacgtagacatggcgaaagaaatg  720

Alk36: 1681  atggagttcacaagaacaaacatcttaaaccaagcgtctcaagcgatgcttgctcaagca 1740
             ||||||||||||||||||||||||||||||||||||||||||||||||||||||||||||
C-125:  721  atggagttcacaagaacaaacatcttaaaccaagcgtctcaagcgatgcttgctcaagca  780

Alk36: 1741  aaccaacagccacaagctgtattacaattacttcgttaa 1779
             |||||||||||||||||||||||||||||||||||||||
C-125:  781  aaccaacagccacaagctgtattacaattacttcgttaa  819
```

FIGURE 3

```
GTAGACTTATTAAAGTGTGGTGACATTTGACATGAAAGTAATTGAAACCAAATACAACGGTAAAATTGGAAGTGGCTGGGGA
TAGGCTCATTGCTTTTGTTCAAGGAATTCCTGCGTTTGAAGATGAAAAGGAGTTTGTCCTTCTGCCATTTGAAGAGGGGACC
CATACTATACCCTTCAATCGACAAAAACAGTGGATTTAGCGTTTATCATCGTGAACCCATTTTCATTTTTTCCAGAGTATCGT
GTGAAATTGCCAGAGGCAACGATTGTTCAGCTCAACATAACGGATGAGAACGATGTGGCCATTTTTTCGTTGCTAACAGTTA
AGGAGCCTTTCTCGGAAACAACGGTAAATTTGCAAGCTCCGATCGTGATCAATGCGAATAAACAAATGGGAAAACAGCTAC
TGCTTGGGGATACAGCTTACGACCGGAAACAACCTCTTTTTCAAAAAGAGCTTGTGCTGGGCAAAGGAGGCGAAGTAAATG
CTTGTCCTCTCACGGAAGTCGAACGAGTCGATCCAAATCGGAGATAACATTGAAATCTCCATTATTTCGATCGACGGTGACC
AAGTAAAGCTAGGGATTAACGCCCCGCGTTGATATTGATATTCACCGAAAAGAAGTGTATTTGGCGATACAACCAAGAGAA
CAGCGAAGCGGCCAAAACCGTGCCATTAAGCCAATTAAAAGGTTTATCGAACCAACAAGGCTAGATCGACGGATCTGGTCT
TTTTTTGTTTACACTCGCGTTACGCTCTTTCTGTTGTTCGTATTGCTTCTTTTGGAGTCCCCCGGTTACGAGAAAAAATCATAA
AAAATTTTAAAAAGGACTAAACTCCTTGAAATCGTGTCGATATTATTAATGTACCGGAAAAGGAAAAGGCGGCCGACTT
TGTTCCTTTTCGCGGATTAAGTTTACACCAACCACAAGGATGTGGGCGGAAAACCATTTCAAGGAGGATTTTAATGAT
TATCAATCACAATTTACCAGCAATGAATGCGCATCGTAACATGGGTATCAATCTTAACCAAGGTCAAAAGCGATGG
AGAAGCTTTCTTCAGGTCTTCGCATTAACCGTGCAGGAGACGATGCTGCAGGTCTTGCCATCTCTGAAAAAATGCGT
GCGCAAATCCGTGGTTTGGATCAAGCGTCTCGTAACTCACAAGACGGTATTTCGTTAATTCAAACAGCTGAAGGTGC
GCTTGATGAAGTACATTCTATTCTTCAACGTATGCGTGAGCTAGCGGTTCAATCTTCGAACGAAACGAATGTTGAGC
AAGATCAAGCAGCTCTTAACGATGAATTCCAACAATTAGTTGAGGAAATTGAAAGAATCAAAGATACAACTCAATTT
AATACGCAAAAATTACTCGATGATACAGTAGATACTGTACAACTTCAAGTTGGTGCTAATTCTGGTGAATTAATTGAA
CTTGATTTAACAAAAGTTGATTTATCAGCTATCCATACAGCTTTGGCGGCTGAGGATATTACTGACCACACTAATGCA
CAATCAGCTATTGACGCTATTGATGAGCAATTAAAAGCTGTTTCAGAAGGTCGCTCTTACCTAGGAGCTATGCAAAA
CCGCCTAGAGCATACAATCAAAAACCTTGATAATGCTTCTGAAAACCTTCAAGCTGCTGAGTCTCGTATCCGTGACG
TAGACATGGCGAAAGAAATGATGGAGTTCACAAGAACAAACATCTTAAACCAAGCGTCTCAAGCGATGCTTGCTCAA
GCAAACCAACAGCCACAAGCTGTATTACAATTACTTCGTTAATTTGCTTCCATTTAAAGATCTGGATTTATTCCAGGTCTT
TTTTATTTTTCGCTCAACCGTTACTTTGTTGATAGGTTGTTAAAGTTTAGGAATGAGATACCGATATAATAGATATGAAAACT
TTTACGTGGAAGGGAGTTCTCCAATGGAAACAAATTTATCAAAAAGTCAGTATGCAGGACAAGTAGGAGTTCAAGTAGCTA
AAACAGTTGTTAAAGCACAGGAGACGGTTCAATTAGAAGAGTATGAGCCAAGTAAGCGTGACGTTCAACATAAAATTGATG
ACATCAATAAAGTCATCGAGACATTGAATACAGGGGTTCGATTTGCCTTGCATGAAGATTTGAATGAGTACTACGTAACCAT
TGTTGATAAAATAACCAATGAAGTGGTTAAGGAGATTCCCCCTAAGAAGTTATTGGATATTTATGCAGCGATGAAGGAAAC
GATTAGTGGCTTTTTTGATAAAAAAATTTAGCGAAAGGTGGGCTTAAGACATGAGAATCGGCGGCATTGCGAGTGGAATT
GATACGGAAAGCATGATTAAACAGTTAATGCAAGTTGAAAGAATCCCATTAAATAAATTTACGGAGAGGAAGATCACGTTA
GAATGGCAACGAGATGCCTATCGTGAAGTAAACCTATTATTAAAAAAGCTAGATGATGCAGCCGCTAATATTCGTTTACGTT
CCTCTTTAAATACGAAAGAAGCTT
```

FIGURE 6

```
           GTAGACTTATTAAAGTGTGGTGACATTTGACATGAAAGTAATTGAAACCAAATACAACGG
           TAAATTGGAAGTGGCTGGGGATAGGCTCATTGCTTTTGTTCAAGGAATTCCTGCGTTTGA
           AGATGAAAAGGAGTTTGTCCTTCTGCCATTTGAAGAGGGGACCCATACTATACCCTTCAA
           TCGACAAAAACAGTGGATTTAGCGTTTATCATCGTGAACCCATTTTCATTTTTTCCAGAG
5          TATCGTGTGAAATTGCCAGAGGCAACGATTGTTCAGCTCAACATAACGGATGAGAACGAT
           GTGGCCATTTTTTCGTTGCTAACAGTTAAGGAGCCTTTCTCGGAAACAACGGTAAATTTG
           CAAGCTCCGATCGTGATCAATGCGAATAAACAAATGGGAAAACAGCTAGTGCTTGGGGAT
           ACAGCTTACGACCGGAAACAACCTCTTTTTCAAAAAGAGCTTGTGCTGGGCAAAGGAGGC
           GAAGTAAATGCTTGTCCTCTCACGGAAGTCGAACGAGTCGATCCAAATCGGAGATAACAT
10         TGAAATCTCCATTATTTCGATCGACGGTGACCAAGTAAAGCTAGGGATTAACGCCCCGCG
           TTCATATTGATATTCACCGAAAAGAAGTGTATTTGGCGATACAACCAAGAGAACAGCGAA
           GCGGCCAAAACCGTGCCATTAAGCCAATTAAAAGGTTTATCGAACCAACAAGGCTAGATC
           GACGGATCTGGTCTTTTTTTGTTTACACTCGCGTTACGCTCTTTCTGTTGTTCGTATTGC
           TTCTTTTGGAGTCCCCCGGTTACGAGAAAAAATCATAAAAAATTTTAAAAAGGA CTAAA C
15         TCCTGTGAAATCGTG TCGATAT TATTAATGTACCGGAAAAGGAAAAGGCGGCCGACTTTG
                            ‾‾‾‾‾‾
           TTCCTTTTCGCGGATTAAGTTTACACCAACCACAAGGATGTGGCGGAAAACACATTTCA
      1    AGGAGGAAATTTTAATGATTATCAATCACAATTTACCAGCAATGAATGCGCATCGTAACA
           ‾‾‾‾‾‾‾
      1                    M  I  I  N  H  N  L  P  A  M  N  A  H  R  N 20    47   TGGGTATCAATCTTAACCAAGGTCAAGAAGCGATGGAGAAGCTTTCTTCAGGTCTTCGCA
      16    M  G  I  N  L  N  Q  G  Q  E  A  M  E  K  L  S  S  G  L  R

107  TTAACCGTGCAGGAGACGATGCTGCAGGTCTTGCCATCTCTGAAAAAATGCGTGCGCAAA
      36    I  N  R  A  G  D  D  A  A  G  L  A  I  S  E  K  M  R  A  Q
25
      167  TCCGTGGTTTGGATCAAGCGTCTCGTAACTCACAAGACGGTATTTCGTTAATTCAAACAG
      56    I  R  G  L  D  Q  A  S  R  N  S  Q  D  G  I  S  L  I  Q  T

227  CTGAAGGTGCGCTTGATGAAGTACATTCTATTCTTCAACGTATGCGTGAGCTAGCGGTTC
30    76    A  E  G  A  L  D  E  V  H  S  I  L  Q  R  M  R  E  L  A  V

287  AATCTTCGAACGAAACGAATGTTGAGCAAGATCAAGCAGCTCTTAACGATGAATTCCAAC
      96    Q  S  S  N  E  T  N  V  E  Q  D  Q  A  A  L  N  D  E  F  Q 35    347  AATTAGTTGAGGAAATTGAAAGAATCAAAGATACAACTCAATTTAATACGCAAAAATTAC
      116   Q  L  V  E  E  I  E  R  I  K  D  T  T  Q  F  N  T  Q  K  L

407  TCGATGATACAGTAGATACTGTACAACTTCAAGTTGGTGCTAATTCTGGTGAATTAATTG
      136   L  D  D  T  V  D  T  V  Q  L  Q  V  G  A  N  S  G  E  L  I
40
      467  AACTTGATTTAACAAAAGTTGATTTATCAGCTATCCATACAGCTTTGGCGGCTGAGGATA
      156   E  L  D  L  T  K  V  D  L  S  A  I  H  T  A  L  A  A  E  D

527  TTACTGACCACACTAATGCACAATCAGCTATTGACGCTATTGATGAGCAATTAAAAGCTG
45    176   I  T  D  H  T  N  A  Q  S  A  I  D  A  I  D  E  Q  L  K  A

587  TTTCAGAAGGTCGCTCTTACCTAGGAGCTATGCAAAACCGCCTAGAGCATACAATCAAAA
      196   V  S  E  G  R  S  Y  L  G  A  M  Q  N  R  L  E  H  T  I  K 50    647  ACCTTGATAATGCTTCTGAAAACCTTCAAGCTGCTGAGTCTCGTATCCGTGACGTAGACA
      216   N  L  D  N  A  S  E  N  L  Q  A  A  E  S  R  I  R  D  V  D

707  TGGCGAAAGAAATGATGGAGTTCACAAGAACAAACATCTTAAACCAAGCGTCTCAAGCGA
      236   M  A  K  E  M  M  E  F  T  R  T  N  I  L  N  Q  A  S  Q  A
55
      767  TGCTTGCTCAAGCAAACCAACAGCCACAAGCTGTATTACAATTACTTCGTTAATTTGCTT
      256   M  L  A  Q  A  N  Q  Q  P  Q  A  V  L  Q  L  L  R  *

CCATTTAAAGATCTGGATTTATTCCAGGTCTTTTTTATTTTTCGCTCAACCGTTACTTTG
60         TTGATAGGTTGTTAAAGTTTAGGAATGAGATACCGATATAATAGATATGAAAACTTTTAC
           GTGGAAGGGAGTTCTCCAATGGAAACAAATTTATCAAAAAGTCAGTATGCAGGACAAGTA
           GGAGTTCAAGTAGCTAAAACAGTTGTTAAAGCACAGGAGACGGTTCAATTAGAAGAGTAT
           GAGCCAAGTAAGCGTGACGTTCAACATAAAATTGATGACATCAATAAAGTCATCGAGACA
```

```
TTGAATACAGGGGTTCGATTTGCCTTGCATGAAGATTTGAATGAGTACTACGTAACCATT
GTTGATAAAATAACCAATGAAGTGGTTAAGGAGATTCCCCCTAAGAAGTTATTGGATATT
TATGCAGCGATGAAGGAAACGATTAGTGGCTTTTTTGATAAAAAAATTTAGCGAAAGGT
GGGCTTAAGACATGAGAATCGGCGGCATTGCGAGTGGAATTGATACGGAAAGCATGATTA
AACAGTTAATGCAAGTTGAAAGAATCCCATTAAATAAATTTACGCAGAGGAAGATCACGT
TAGAATGGCAACGAGATGCCTATCGTGAAGTAAACCTATTATTAAAAAAGCTAGATGATG
CAGCCGCTAATATTCGTTTACGTTCCTCTTTAAATACGAAAGAAGCTT
```

FIGURE 7

```
...............ATGAAAGTAATTGAAACCAAATACAACGGTAAATTGGAAGTGGCTGGGGAT
AGGCTCATTGCTTTTGTTCAAGGAATTCCTGCGTTTGAAGATGAAAAGGAGTTTGTCCTTCTGCCATTTGA
AGAGGGGACCCATACTATACCCTTCAATCGACAAAAACAGTGGATTTAGCGTTTATCATCGTGAACCCAT
TTTCATTTTTTCCAGAGTATCGTGTGAAATTGCCAGAGGCAACGATTGTTCAGCTCAACATAACGGATGAG
AACGATGTGGCCATTTTTTCGTTGCTAACAGTTAAGGAGCCTTTCTCGGAAACAACGGTAAATTTGCAAGC
TCCGATCGTGATCAATGCGAATAAACAAATGGGAAAACAGCTAGTGCTTGGGGATACAGCTTACGACCG
GAAACAACCTCTTTTTCAAAAAGAGCTTGTGCTGGGCAAAGGAGGCGAAGTAAATGCTTGTCCTCTCACG
GAAGTCGAACGAGTCGATCCAAATCGGAGATAACATTGAAATCTCCATTATTTCGATCGACGGTGACCAA
GTAAAGCTAGGGATTAACGCCCCGCGTTCATATTGATATTCACCGAAAAGAAGTGTATTTGGCGATACAA
CCAAGAGAACAGCGAAGCGGCCAAAACCGTGCCATTAAGCCAATTAAAAGGTTTATCGAACCAACAAGG
CTAGATCGACGGATCTGGTCTTTTTTTGTTTACACTCGCGTTACGCTCTTTCTGTTGTTCGTATTGCTTCTTT
TGGAGTCCCCCGGTTACGAGAAAAAATCATAAAAAATTTTAAAAAGGACTAAACTCCTGTGAAATCGTGT
CGATATTATTAATGTACCGGAAAAGGAAAAGGCGGCCGACTTTGTTCCTTTTCGCGGATTAAGTTTACACC
AACCACAAGGATGTGGGCCGGAAAAACACATTTCAAGGAGGAAATTTTAATGATTATCAATCACAATTTA...
...............TAACATGGGTATCAATCTTAACCAAGGTCAAGAAGCGATGGAGAAGCT
TTCTTCAGGTCTTCGCATTAACCGTGCAGGAGACGATGCTGCAGGTCTTGCCATCTCTGAAAAAAT
GCGTGCGCAAATCCGTGGTTTGGATCAAGCGTCTCGTAACTCACAAGACGGTATTTCGTTAATTCA
AACAGCTGAAGGTGCGCTTGATGAAGTACATTCTATTCTTCAACGTATGCGTGAGCTAGCGGTTCA
ATCTTCGAACGAAACGAATGTTGAGCAAGATCAAGCAGCTCTTAACGATGAATTCCAACAATTAGTT
GAGGAAATTGAAAGAATCAAAGATACAACTCAATTTAATACGCAAAAATTACTCGATGATACAGTAG
ATACTGTACAACTTCAAGTTGGTGCTAATTCTGGTGAATTAATTGAACTTGATTTAACAAAAGTTGA
TTTATCAGCTATCCATACAGCTTTGGCGGCTGAGGATATTACTGACCACACTAATGCACAATCAGCT
ATTGACGCTATTGATGAGCAATTAAAAGCTGTTTCAGAAGGTCGCTCTTACCTAGGAGCTATGCAAA
ACCGCCTAGAGCATACAATCAAAAACCTTGATAATGCTTCTGAAAACCTTCAAGCTGCT.........
.........ACGTAGACATGGCGAAAGAAATGATGGAGTTCACAAGAACAAACATCTTAAACCAAGCGTC
TCAAGCGATGCTTGCTCAAGCAAACCAACAGCCACAAGCTGTATTACAATTACTTCGTTAATTTGCTTCCA
TTTAAAGATCTGGATTTATTCCAGGTCTTTTTTATTTTTCGCTCAACGTTACTTTGTTGATAGGTTGTTAA
AGTTTAGGAATGAGATACCGATATAATAGATATGAAAACTTTTACGTGGAAGGGAGTTCTCCAATGGAAA
CAAATTTATCAAAAAGTCAGTATGCAGGACAAGTAGGAGTTCAAGTAGCTAAAACAGTTGTTAAAGCAC
AGGAGACGGTTCAATTAGAAGAGTATGAGCCAAGTAAGCGTGACGTTCAACATAAAAATTGATGACATCA
ATAAAGTCATCGAGACATTGAATACAGGGGTTCGATTTGCCTTGCATGAAGATTTGAATGAGTACTACGT
AACCATTGTTGATAAAATAACCAATGAAGTGGTTAAGGAGATTCCCCCTAAGAAGTTATTGGATATTTAT
GCAGCGATGAAGGAAACGATTAGTGGCTTTTTTGATAAAAAAATTTTAGCGAAAGGTGGGCTTAAGACAT
GAGAATCGGCGGCATTGCGAGTGGAATTGATACGGAAAGCATGATTAAACAGTTAATGCAAGTTGAAAG
AATCCCATTAAATAAATTTACGCAGAGGAAGATCACGTTAGAATGGCAACGAGATGCCTATCGTGAAGTA
AACCTATTATTAAAAAAGCTAGATGATGCAGCCGCTAATATT.................
```

FIGURE 9A

```
NC:   CEEEEHHHH  HHHHHHHHHH  HHHHHHHHHH  HCCCEECCCC  CCHHHHHHHH  HHHHHHHHHH
NC1:  CEEECCHHHH  HHHHHHHHHH  HHHHHHHHHH  HCCCEECCHH  HCHHHHHHHH  HHHHHHHHHH
NC2:  CEEECHHHH   HHHHHHHHHH  HHHHHHHHHH  HCCCEECCCC  CCHHHHHHHH  HHHHHHHHHH
NC3:  CEEECHHHH   HHHHHHHHHH  HHHHHHHHHH  HCCCEECCCC  CCHHHHHHHH  HHHHHHHHHH
NC5:  CEEECHHHH   HHHHHHHHHH  HHHHHHHHHH  HCCCEECCCC  CCHHHHHHHH  HHHHHHHHHH
NC6:  CEEEHHHHH   HHHHHHHHHH  HHHHHHHHHH  HCCCEECCCC  CCHHHHHHHH  HHHHHHHHHH
AA:   MIINHNLPAM  NAHRNMGINL  NQGQKAMEKL  SSGLRINRAG  DDAAGLAISE  KMRAQIRGLD
           10          20          30          40          50          60

NC:   ..HHHHHHHHHH  HHHHHHHHHH  HHHHHHHHHH  HHHHHHHHCC  CCCHHHHHHH  HHHHHHHHHH
NC1:  HHHHHHHHHH   HHHHHHHHHH  HHHHHHHHHH  HHHHHHHCCC  CCCHHHHHHH  HHHHH-----
NC2:  HHHHHHHHHH   HHHHHHHHHH  HHHHHHHHHH  HHHHHHHHCC  CCCHHHHHHH  HHHHHHHHHH
NC3:  HHHHHHHHHH   HHHHHHHHHH  HHHHHHHHHH  HHHHHHHHCC  CCCHHHHHHH  HHHHHHHHHH
NC5:  HHHHHHHHHH   HHHHHHHHHH  HHHHHHHHHH  HHHHHHHHCC  CCCHHHHHHH  HHHHHHHHHH
NC6:  HHHHHHHHHH   HHHHHHHHHH  HHHHHHHHHH  HHHHHHHHCC  CCCHHHHHHH  HHHHHHHHHH
AA:   QASRNSQDGI   SLIQTAEGAL  DEVHSILQRM  RELAVQSSNE  TNVEQDQAAL  NDEFQQLVEE
           70          80          90          100         110         120

┌──►NC1
NC:   HHHHHHCCE----------ECCE..EEECCCCCE..EEEEECCCC------------E.EEEEEEECH
NC1:  ----------------------------------------------------------------------
NC2:  HHHHHHCCE----------ECCE..EEECCCCCE..EEEEECCCC------------E.EEEEEEECC
NC3:  HHHHHHCCE----------ECCE..EEECCCCCE..EEEEECCCC EEEEEECCCC CHHCCEEECC
NC5:  HHHHHHHCE ..CCCCCCCCE..EEEECCCEE..EEEEECCCC-----------E.EEEEEEECH
NC6:  HHHHHHHCE----------ECCE.EEEECCCCCE..EEEEECCCCC-----------E.EEEEEEECCC
AA:   IERIKDTTQV  NSSPGSFNTQ  KLLDDTVDTV  QLQVGANSGE  QLPDSSPGSL  IELDLTKVDL
                  NC5                                  NC3
           130         140         150         160         170         180

NC1
                                                                  ◄┐
NC:   HHHCCEEEEE  EEEECC--------CCHHH  HHHHHHHHHH  HHHHH-------HHHCCCCHHH
NC1:  --------------------------------------------------------HHHHHHHCC
NC2:  CEEEEEEEEE  EECCCC--------CCCHH  HHHHHHHHEE  ECCEEEHHH  HHHHHHHHHH
NC3:  CCCEECCCCC  EEEEEC--------CCCCH  HHHHHHHHHH  HHHHH-------HHHHHHHHHH
NC5:  HHCCCEEEEE  EECCCC--------CHHH   HHHHHHHHHH  HCCEE-------CCCCCCCHHH
NC6:  HHCCCCCCCC  CCCCCCCCEE  EECCCCHHH  HHHHHHHHHH  HHHHH-------HHHHHHHHHH
AA:   SAIHTALAAE  DITDHTVDSS  PGWIQNAQSA  IDAIDEQLKA  VSEGRSSPGS  SYLGAMQNRL
                             NC6                                NC2
           190         200         210         220         230         240

NC:   .HHHHHHHH H  ..HHHHHHHHHH  HHEECCHHHH  HHHHHHHHHH  HHHHHHHHHH  HCCCHHHHHH  HCC
NC1:  EECCEEECCC  CEEEHEEEEE  EEEEECHHHH  HHHHHHHHHH  HHHHHHHHHH  HCCCHHHHHH  HCC
NC2:  HHHHHHHHHH  HHHHHHHHHH  HHEECCHHHH  HHHHHHHHHH  HHHHHHHHHH  HCCCHHHHHH  HCC
NC3:  HHHHHHHHHH  HHHHHHHHHH  CCCEECHHHH  HHHHHHHHHH  HHHHHHHHHH  HHCCCHHHHH  HCC
NC5:  HHHHHHHHHH  HHHHHHHHHH  HEECHHHHHH  HHHHHHHHHH  HHHHHHHHHH  CCCHHHHHHH  HCC
NC6:  HHHHHHHHHH  HHHHHHHHCC  CEECCHHHHH  HHHHHHHHHH  HHHHHHHHHH  HCCCHHHHHH  HCC
AA:   EHTIKNLDNA  SENLQAAESR  IRDVDMAKEM  MEFTRTNILN  QASQAMLAQA  NQQPQAVILQ  LLR
           250         260         270         280         290         300
```

FIGURE 11

TCG AGC CCG GGA TCC
Ser - Ser - Pro - Gly - Ser

FIGURE 12A

CAG CTG CCG GAC  TCG AGC CCG GGA TCC
Gln - Leu - Pro - Asp  - Ser - Ser - Pro - Gly  - Ser

FIGURE 12B

GTC GAC TCG AGC CCG GGA TCC
Val - Asp - Ser - Ser - Pro - Gly - Ser

FIGURE 12C

GTC GAC TCG AGC CCG GGA TGG ATC CAG
Val - Asp - Ser - Ser - Pro - Gly - Trp - Ile - Gln

FIGURE 12D

5' - GCC GAC TCG AGA CAT CAT CAT CAT CAT CAC AGG ATC CGA -3'
Ala - Asp - Ser - Arg - His - His - His - His - His - His - Arg - Ile - Arg

5'- GTC GAC TCG AGA CGT TCA TTA TCA TAT GGA CCA GGA CGT GCA TTT CGT ACG CGT TGG ATC CAG -3'
Val - Asp - Ser - Arg - Arg - Ser - Leu - Ser - Tyr - Gly - Pro - Gly - Arg - Ala - Phe - Arg - Thr - Arg - Trp - Ile - Gln
FIGURE 20
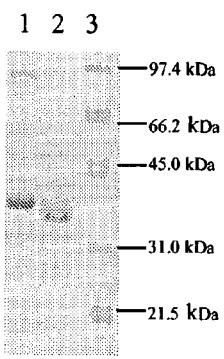
FIGURE 21
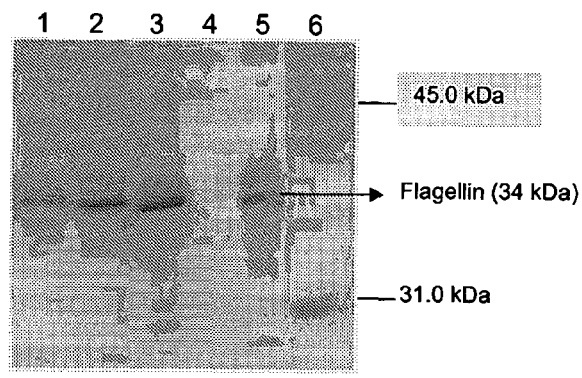
FIGURE 22

```
1    GCTTCACGCGCCAACGATGCGCCGATTGTACTTCTCCATGGCTTTACTGGCTGGGGAAGA
1    A  S  R  A  N  D  A  P  I  V  L  L  H  G  F  T  G  W  G  R

61   GAAGAAATGTTTGGGTTCAAGTACTGGGGCGGCGTGCGCGGCGATATCGAACAATGGCTG
21   E  E  M  F  G  F  K  Y  W  G  G  V  R  G  D  I  E  Q  W  L

121  AACGACAACGGTTATCGAACTTATACGCTGGCGGTCGGACCGCTCTCGAGCAACTGGGAC
41   N  D  N  G  Y  R  T  Y  T  L  A  V  G  P  L  S  S  N  W  D

181  CGGGCGTGTGAAGCGTATGCTCAACTTGTCGGCGGGACGGTCGATTATGGGGCAGCCCAT
61   R  A  C  E  A  Y  A  Q  L  V  G  G  T  V  D  Y  G  A  A  H

241  GCGGCAAAGCACGGCCATGCGCGGTTTGGCCGCACTTATCCCGGCCTGTTGCCGGAATTG
81   A  A  K  H  G  H  A  R  F  G  R  T  Y  P  G  L  L  P  E  L

301  AAAAGGGGTGGCCGCATCCATATCATCGCCCACAGCCAAGGGGGGCAGACGGCCCGCATG
101  K  R  G  G  R  I  H  I  I  A  H  S  Q  G  G  Q  T  A  R  M

361  CTTGTCTCGCTCCTAGAGAACGGAAGCCAAGAAGAGCGGGAGTACGCCAAGGCGCACAAC
121  L  V  S  L  L  E  N  G  S  Q  E  E  R  E  Y  A  K  A  H  N

421  GTGTCGTTGTCACCGTTGTTTGAAGGTGGACATCATTTTGTGTTGAGTGTGACGACCATC
141  V  S  L  S  P  L  F  E  G  G  H  H  F  V  L  S  V  T  T  I

481  GCCACTCCTCATGACGGGACGACGCTTGTCAACATGGTTGATTTCACCGATCGCTTTTTT
161  A  T  P  H  D  G  T  T  L  V  N  M  V  D  F  T  D  R  F  F

541  GACTTGCAAAAAGCGGTGTTGGAAGCGGCGGCTGTCGCCAGCAACGTGCCGTACACGAGT
181  D  L  Q  K  A  V  L  E  A  A  A  V  A  S  N  V  P  Y  T  S

601  CAAGTATACGATTTTAAGCTTGACCAATGGGGACTGCGCCGCCAGCCGGGTGAATCGTTC
201  Q  V  Y  D  F  K  L  D  Q  W  G  L  R  R  Q  P  G  E  S  F

661  GACCATTATTTTGAACGGCTCAAGCGCTCCCCTGTTTGGACGTCCACAGATACCGCCCGC
221  D  H  Y  F  E  R  L  K  R  S  P  V  W  T  S  T  D  T  A  R

721  TACGATTTATCCGTTTCCGGAGCTGAGAAGTTGAATCAATGGGTGCAAGCAAGCCCGAAT
241  Y  D  L  S  V  S  G  A  E  K  L  N  Q  W  V  Q  A  S  P  N

781  ACGTATTATTTGAGCTTTGCCACAGAACGGACGTATCGCGGAGCGCTCACAGGCAACTAT
261  T  Y  Y  L  S  F  A  T  E  R  T  Y  R  G  A  L  T  G  N  Y

841  TATCCCGAACTCGGAATGAATGCATTCAGCGCGGTCGTATGCGCTCCGTTTCTCGGTTCG
281  Y  P  E  L  G  M  N  A  F  S  A  V  V  C  A  P  F  L  G  S

901  TACCGCAATCCGACGCTCGGCATTGACGACCGCTGGCTTGAAAACGATGGCATTGTCAAT
301  Y  R  N  P  T  L  G  I  D  D  R  W  L  E  N  D  G  I  V  N

961  ACGGTTTCCATGAACGGTCCAAAGCGTGGATCAAGCGATCGGATCGTACCGTATGACGGG
321  T  V  S  M  N  G  P  K  R  G  S  S  D  R  I  V  P  Y  D  G

1021 GCGTTGAAAAAGGGGTTTGGAATGACATGGGAACGTACAATGTCGACCATTTGGAAATC
341  A  L  K  K  G  V  W  N  D  M  G  T  Y  N  V  D  H  L  E  I

1081 ATCGGCGTTGACCCGAATCCGTCATTTGATATTCGCGCCTTTTATTTGCGACTTGCCGAG
361  I  G  V  D  P  N  P  S  F  D  I  R  A  F  Y  L  R  L  A  E

1141 CAGTTGGCGAGTTTGCGGCCT
381  Q  L  A  S  L  R  P
```

FIGURE 23

```
AMKTKTGKKITALFLVFMLLCSVLQPFGAYANALGSIDTATPITKGQEYQLTFEEEEQVHW
YKIDSIEEDAKDDSHYQIQLTSENEMNISVYPSLDRAKSDDTYSSYKSYSMLGETGKINFP
LAWTGPYYIKVEYYGSDEEWEEEGEEESPTTADYTLSFEGIKLPPSTGMEEEDCPVELSA
SQKESGKELLKSLRTIRDQVFSQTEQGKEFTSLYYKAAPFIVSKIAFDQKLKDQVYQDLVT
LTPLFKELLDNGANSTYKITKKDQDAILRLYELGADSVPHSLRAEMEKINQQVNLQKIEGLR
LATVLDKAGMAPDTASTSNKVIVKLKEGKSVSALEAKAEDVNDEATISPFEDQDPLFEDM
YIVELGDEQEVSISSQELDMTVDQLENLPEVEYAEPVQEYVALSADIHYSDQWSLENEGG
NLGEAGADIKYAPLQELVKEKNLPNTLIAVIDTGVDSRLADLENQVRTDLGYNFIGRNTNAL
DDNGHGTHVAGIIAAESNNHYSMTGINHAAEIIPIKVLDGGGSGDTESIASGIKYAADQGAD
VINLSLGGSYSRVIEASLKYASEKGVTIVAASGNEYSPYLSYPASSRYVISVGATNRSDIVS
DYSNYGKGLDLVAPGTDIPSLLPNGNVTYFDGTSMAAPHVAAVAGLLLSQNAKLSSEDIQ
KILTETTDYIAFEELDNEEDYYFYYDDEEEPVLLPGYDEASGWGRLNAHSAVSAVDLNVK
VNRLLDNQNVVTGSAKKGTTIEVTNGSETLGSGPVDANGKFKVKIPVQPANQVLYVKASQ
 GAAKASIRIAVEEGKKPKAPKVNTVSNKDTHVTGTTEPNLTVNVKDKNKKVIATGKADKN
GAFKVKINKQKENTTLYVTAMDLGNKESKAVKIKVIDKIPPKAPKVNSISDRTTTVKGETEP
NATVTIKKNGKKLASGKADKNGKFSIKISKQKAGTKLSITAKDKAGNVSKATTKTVKDKTPP
KKPTVNKVTSRDTKVTGKTEANATVTIKRDGKTLASGKADKNGKFSIKISKQKKGTKLSVT
                    AKDKAGNTSKATKVTVQ
```

FIGURE 26

SEQUENCE LISTING

<160> NUMBER OF SEQ ID NOS: 63

<210> SEQ ID NO 1
<211> LENGTH: 819
<212> TYPE: DNA
<213> ORGANISM: Bacillus halodurans

<400> SEQUENCE: 1

```
atgattatca atcacaattt accagcaatg aatgcgcatc gtaacatggg tatcaatctt      60
aaccaaggtc aagaagcgat ggagaagctt tcttcaggtc ttcgcattaa ccgtgcagga     120
gacgatgctg caggtcttgc catctctgaa aaaatgcgtg cgcaaatccg tggtttggat     180
caagcgtctc gtaactcaca agacggtatt tcgttaattc aaacagctga aggtgcgctt     240
gatgaagtac attctattct tcaacgtatg cgtgagctag cggttcaatc ttcgaacgaa     300
acgaatgttg agcaagatca agcagctctt aacgatgaat ccaacaatt agttgaggaa      360
attgaaagaa tcaaagatac aactcaattt aatacgcaaa aattactcga tgatacagta     420
gatactgtac aacttcaagt tggtgctaat tctggtgaat taattgaact tgatttaaca     480
aaagttgatt tatcagctat ccatacagct ttggcggctg aggatattac tgaccacact     540
aatgcacaat cagctattga cgctattgat gagcaattaa aagctgtttc agaaggtcgc     600
tcttacctag agctatgca aaccgccta gagcatacaa tcaaaaacct tgataatgct       660
tctgaaaacc ttcaagctgc tgagtctcgt atccgtgacg tagacatggc gaaagaaatg     720
atggagttca agaacaaa catcttaaac caagcgtctc aagcgatgct tgctcaagca      780
aaccaacagc cacaagctgt attacaatta cttcgttaa                           819
```

```
<210> SEQ ID NO 2
<211> LENGTH: 272
<212> TYPE: PRT
<213> ORGANISM: Bacillus halodurans
```

<400> SEQUENCE: 2

```
Met Ile Ile Asn His Asn Leu Pro Ala Met Asn Ala His Arg Asn Met
1               5                   10                  15

Gly Ile Asn Leu Asn Gln Gly Gln Glu Ala Met Glu Lys Leu Ser Ser
            20                  25                  30

Gly Leu Arg Ile Asn Arg Ala Gly Asp Asp Ala Ala Gly Leu Ala Ile
        35                  40                  45

Ser Glu Lys Met Arg Ala Gln Ile Arg Gly Leu Asp Gln Ala Ser Arg
    50                  55                  60

Asn Ser Gln Asp Gly Ile Ser Leu Ile Gln Thr Ala Glu Gly Ala Leu
65                  70                  75                  80

Asp Glu Val His Ser Ile Leu Gln Arg Met Arg Glu Leu Ala Val Gln
                85                  90                  95

Ser Ser Asn Glu Thr Asn Val Glu Gln Asp Gln Ala Ala Leu Asn Asp
            100                 105                 110

Glu Phe Gln Gln Leu Val Glu Glu Ile Glu Arg Ile Lys Asp Thr Thr
        115                 120                 125

Gln Phe Asn Thr Gln Lys Leu Leu Asp Asp Thr Val Asp Thr Val Gln
    130                 135                 140

Leu Gln Val Gly Ala Asn Ser Gly Glu Leu Ile Glu Leu Asp Leu Thr
145                 150                 155                 160

Lys Val Asp Leu Ser Ala Ile His Thr Ala Leu Ala Ala Glu Asp Ile
                165                 170                 175

Thr Asp His Thr Asn Ala Gln Ser Ala Ile Asp Ala Ile Asp Glu Gln
            180                 185                 190

Leu Lys Ala Val Ser Glu Gly Arg Ser Tyr Leu Gly Ala Met Gln Asn
        195                 200                 205

Arg Leu Glu His Thr Ile Lys Asn Leu Asp Asn Ala Ser Glu Asn Leu
```

```
            210                 215                 220
Gln Ala Ala Glu Ser Arg Ile Arg Asp Val Asp Met Ala Lys Glu Met
225                 230                 235                 240

Met Glu Phe Thr Arg Thr Asn Ile Leu Asn Gln Ala Ser Gln Ala Met
                245                 250                 255

Leu Ala Gln Ala Asn Gln Gln Pro Gln Ala Val Leu Gln Leu Leu Arg
            260                 265                 270

<210> SEQ ID NO 3
<211> LENGTH: 22
<212> TYPE: PRT
<213> ORGANISM: unknown
<220> FEATURE:
<223> OTHER INFORMATION: The unknown organism is Bacillus ALK36 bacteria
      deposited under accesssion number NCIMB 41348.

<400> SEQUENCE: 3

Met Ile Ile Asn His Asn Leu Pro Ala Ala Asn Ala Ala Tyr Gln Asn
1               5                   10                  15

Gly Gly Asn Gln Leu Thr
            20

<210> SEQ ID NO 4
<211> LENGTH: 22
<212> TYPE: PRT
<213> ORGANISM: Bacillus

<400> SEQUENCE: 4

Met Ile Ile Asn His Asn Leu Pro Ala Met Asn Ala His Arg Asn Met
1               5                   10                  15

Gly Ile Asn Leu Asn Gln
            20

<210> SEQ ID NO 5
<211> LENGTH: 2503
<212> TYPE: DNA
<213> ORGANISM: unknown
<220> FEATURE:
<223> OTHER INFORMATION: The unknown organism is Bacillus ALK36 bacteria
      deposited under accesssion number NCIMB 41348.

<400> SEQUENCE: 5
gtagacttat taaagtgtgg tgacatttga catgaaagta attgaaacca atacaacgg      60 taaattggaa gtggctgggg ataggctcat tgcttttgtt caaggaattc ctgcgtttga    120
agatgaaaag gagtttgtcc ttctgccatt tgaagagggg acccatacta tacccttcaa    180
tcgacaaaaa cagtggattt agcgtttatc atcgtgaacc cattttcatt ttttccagag    240
tatcgtgtga aattgccaga ggcaacgatt gttcagctca acataacgga tgagaacgat    300
gtggccattt tttcgttgct aacagttaag gagccttttct cggaaacaac ggtaaatttg    360
caagctccga tcgtgatcaa tgcgaataaa caaatgggaa acagctagt gcttggggat    420 acagcttacg accggaaaca acctcttttt caaaaagagc ttgtgctggg caaggaggc    480 gaagtaaatg cttgtcctct cacggaagtc gaacgagtcg atccaaatcg agataacat    540 tgaaatctcc attatttcga tcgacggtga ccaagtaaag ctaggatta acgccccgcg    600 ttcatattga tattcaccga aaagaagtgt atttggcgat acaaccaaga gaacagcgaa    660
gcggccaaaa ccgtgccatt aagccaatta aaaggtttat cgaaccaaca aggctagatc    720
gacggatctg gtcttttttt gtttacactc gcgttacgct ctttctgttg ttcgtattgc    780
```

```
ttcttttgga gtccccoggt tacgagaaaa aatcataaaa aatttttaaaa aggactaaac    840 tccttgaaat cgtgtcgata ttattaatgt accggaaaag gaaaaggcgg ccgactttgt    900 tcctttttcgc ggattaagtt tacaccaacc acaaggatgt gggcggaaaa ccatttcaag   960
gaggatttta atgattatca atcacaattt accagcaatg aatgcgcatc gtaacatggg   1020
tatcaatctt aaccaaggtc aaaagcgatg gagaagcttt cttcaggtct tcgcattaac   1080
cgtgcaggag acgatgctgc aggtcttgcc atctctgaaa aaatgcgtgc gcaaatccgt   1140
ggtttggatc aagcgtctcg taactcacaa gacggtattt cgttaattca aacagctgaa   1200
ggtgcgcttg atgaagtaca ttctattctt caacgtatgc gtgagctagc ggttcaatct   1260
tcgaacgaaa cgaatgttga gcaagatcaa gcagctctta acgatgaatt ccaacaatta   1320
gttgaggaaa ttgaaagaat caagatcaa actcaattta atacgcaaaa attactcgat    1380
gatacagtag atactgtaca acttcaagtt ggtgctaatt ctggtgaatt aattgaactt   1440
gatttaacaa aagttgattt atcagctatc catacagctt tggcggctga ggatattact   1500
gaccacacta atgcacaatc agctattgac gctattgatg agcaattaaa agctgtttca   1560
gaaggtcgct cttacctagg agctatgcaa aaccgcctag agcatacaat caaaaacctt   1620
gataatgctt ctgaaaacct tcaagctgct gagtctcgta tccgtgacgt agacatggcg   1680
aaagaaatga tggagttcac aagaacaaac atcttaaaacc aagcgtctca agcgatgctt   1740
gctcaagcaa accaacagcc acaagctgta ttacaattac ttcgttaatt tgcttccatt   1800
taaagatctg gatttattcc aggtcttttt tattttttcgc tcaaccgtta ctttgttgat   1860
aggttgttaa agtttaggaa tgagataccg atataataga tatgaaaact tttacgtgga   1920
agggagttct ccaatggaaa caaatttatc aaaaagtcag tatgcaggac aagtaggagt   1980
tcaagtagct aaaacagttg ttaaagcaca ggagacggtt caattagaag agtatgagcc   2040
aagtaagcgt gacgttcaac ataaaaattga tgacatcaat aaagtcatcg agacattgaa   2100 tacagggggtt cgatttgcct tgcatgaaga tttgaatgag tactacgtaa ccattgttga   2160
taaaataacc aatgaagtgg ttaaggagat tcccctaag aagttattgg atattttatgc    2220 agcgatgaag gaaacgatta gtggcttttt tgataaaaaa aatttagcga aaggtgggct   2280
taagacatga gaatcggcgg cattgcgagt ggaattgata cggaaagcat gattaaacag   2340
ttaatgcaag ttgaaagaat cccattaaat aaatttacgc agaggaagat cacgttagaa   2400
tggcaacgag atgcctatcg tgaagtaaac ctattattaa aaaagctaga tgatgcagcc   2460
gctaatattc gtttacgttc ctctttaaat acgaaagaag ctt                     2503
```

<210> SEQ ID NO 6
<211> LENGTH: 2476
<212> TYPE: DNA
<213> ORGANISM: unknown
<220> FEATURE:
<223> OTHER INFORMATION: The unknown organism is Bacillus ALK36 bacteria deposited under accesssion number NCIMB 41348.

<400> SEQUENCE: 6

```
gtgtggtgac atttgacatg aaagtaattg aaaccaaata caacggtaaa ttggaagtgg     60
ctggggatag gctcattgct tttgttcaag gaattcctgc gtttgaagat gaaaaggagt    120
ttgtccttct gccatttgaa gaggggaccc atactatacc cttcaatcga caaaaacagt    180
ggatttagcg tttatcatcg tgaacccatt tcattttttt ccagagtatc gtgtgaaatt    240
gccagaggca acgattgttc agctcaacat aacggatgag aacgatgtgg ccattttttc    300
```

-continued

```
gttgctaaca gttaaggagc ctttctcgga acaacggta aatttgcaag ctccgatcgt      360
gatcaatgcg aataaacaaa tgggaaaaca gctagtgctt ggggatacag cttacgaccg      420
gaaacaacct cttttcaaa aagagcttgt gctgggcaaa ggaggcgaag taaatgcttg      480
tcctctcacg gaagtcgaac gagtcgatcc aaatcggaga taacattgaa atctccatta      540
tttcgatcga cggtgaccaa gtaaagctag ggattaacgc cccgcgttca tattgatatt      600
caccgaaaag aagtgtattt ggcgatacaa ccaagagaac agcgaagcgg ccaaaaccgt      660
gccattaagc caattaaaag gtttatcgaa ccaacaaggc tagatcgacg gatctggtct      720
tttttgttt acactcgcgt tacgctcttt ctgttgttcg tattgcttct tttggagtcc      780
cccggttacg agaaaaaatc ataaaaaatt ttaaaaagga ctaaactcct gtgaaatcgt      840
gtcgatatta ttaatgtacc ggaaaaggaa aaggcggccg actttgttcc ttttcgcgga      900
ttaagtttac accaaccaca aggatgtggg cggaaaacac atttcaagga ggaaatttta      960
atgattatca atcacaattt accagcaatg aatgcgcatc gtaacatggg tatcaatctt     1020
aaccaaggtc aagaagcgat ggagaagctt tcttcaggtc ttcgcattaa ccgtgcagga     1080
gacgatgctg caggtcttgc catctctgaa aaaatgcgtg cgcaaatccg tggtttggat     1140
caagcgtctc gtaactcaca agacggtatt tcgttaattc aaacagctga aggtgcgctt     1200
gatgaagtac attctattct tcaacgtatg cgtgagctag cggttcaatc ttcgaacgaa     1260
acgaatgttg agcaagatca agcagctctt aacgatgaat ccaacaatt agttgaggaa     1320
attgaaagaa tcaaagatac aactcaattt aatacgcaaa aattactcga tgatacagta     1380
gatactgtac aacttcaagt tggtgctaat tctggtgaat taattgaact tgatttaaca     1440
aaagttgatt tatcagctat ccatacagct ttggcggctg aggatattac tgaccacact     1500
aatgcacaat cagctattga cgctattgat gagcaattaa aagctgtttc agaaggtcgc     1560
tcttacctag gagctatgca aaaccgccta gagcatacaa tcaaaaacct tgataatgct     1620
tctgaaaacc ttcaagctgc tgagtctcgt atccgtgacg tagacatggc gaaagaaatg     1680
atggagttca caagaacaaa catcttaaac caagcgtctc aagcgatgct tgctcaagca     1740
aaccaacagc cacaagctgt attacaatta cttcgttaat ttgcttccat ttaaagatct     1800
ggatttattc caggtctttt ttattttcg ctcaaccgtt actttgttga taggttgtta     1860
aagtttagga atgagatacc gatataatag atatgaaaac ttttacgtgg aagggagttc     1920
tccaatggaa acaaatttat caaaaagtca gtatgcagga caagtaggag ttcaagtagc     1980
taaaacagtt gttaaagcac aggagacggt tcaattagaa gagtatgagc caagtaagcg     2040
tgacgttcaa cataaaattg atgacatcaa taaagtcatc gagacattga atacagggt      2100
tcgatttgcc ttgcatgaag atttgaatga gtactacgta accattgttg ataaaataac     2160
caatgaagtg gttaaggaga ttccccctaa gaagttattg gatatttatg cagcgatgaa     2220
ggaaacgatt agtggctttt tgataaaaa aatttagcg aaaggtgggc ttaagacatg      2280
agaatcggcg gcattgcgag tggaattgat acggaaagca tgattaaaca gttaatgcaa     2340
gttgaaagaa tcccattaaa taatttacg cagaggaaga tcacgttaga atggcaacga      2400
gatgcctatc gtgaagtaaa cctattatta aaaaagctag atgatgcagc cgctaatatt     2460
cgtttacgtt cctctt                                                     2476
```

<210> SEQ ID NO 7
<211> LENGTH: 5
<212> TYPE: PRT
<213> ORGANISM: artificial sequence

```
<220> FEATURE:
<223> OTHER INFORMATION: NC2 peptides

<400> SEQUENCE: 7

Ser Ser Pro Gly Ser
1               5

<210> SEQ ID NO 8
<211> LENGTH: 15
<212> TYPE: DNA
<213> ORGANISM: artificial sequence
<220> FEATURE:
<223> OTHER INFORMATION: NC2 nucleotide sequence

<400> SEQUENCE: 8
tcgagcccgg gatcc                                                        15

<210> SEQ ID NO 9
<211> LENGTH: 9
<212> TYPE: PRT
<213> ORGANISM: artificial sequence
<220> FEATURE:
<223> OTHER INFORMATION: NC3 peptides

<400> SEQUENCE: 9

Gln Leu Pro Asp Ser Ser Pro Gly Ser
1               5

<210> SEQ ID NO 10
<211> LENGTH: 27
<212> TYPE: DNA
<213> ORGANISM: artificial sequence
<220> FEATURE:
<223> OTHER INFORMATION: NC3 nucleotide sequence

<400> SEQUENCE: 10
cagctgccgg actcgagccc gggatcc                                           27

<210> SEQ ID NO 11
<211> LENGTH: 7
<212> TYPE: PRT
<213> ORGANISM: artificial sequence
<220> FEATURE:
<223> OTHER INFORMATION: NC5 peptides

<400> SEQUENCE: 11

Val Asp Ser Ser Pro Gly Ser
1               5

<210> SEQ ID NO 12
<211> LENGTH: 21
<212> TYPE: DNA
<213> ORGANISM: artificial sequence
<220> FEATURE:
<223> OTHER INFORMATION: NC5 nucleotide sequence

<400> SEQUENCE: 12
gtcgactcga gcccgggatc c                                                 21

<210> SEQ ID NO 13
<211> LENGTH: 9
<212> TYPE: PRT
<213> ORGANISM: artificial sequence
<220> FEATURE:
<223> OTHER INFORMATION: NC6 peptides

<400> SEQUENCE: 13
```

Val Asp Ser Ser Pro Gly Trp Ile Gln
1               5

<210> SEQ ID NO 14
<211> LENGTH: 27
<212> TYPE: DNA
<213> ORGANISM: artificial sequence
<220> FEATURE:
<223> OTHER INFORMATION: NC6 nucleotide sequence

<400> SEQUENCE: 14
gtcgactcga gcccgggatg gatccag                                        27

<210> SEQ ID NO 15
<211> LENGTH: 21
<212> TYPE: PRT
<213> ORGANISM: HIV

<400> SEQUENCE: 15

Val Asp Ser Arg Arg Ser Leu Ser Tyr Gly Pro Gly Arg Ala Phe Arg
1               5                   10                  15

Thr Arg Trp Ile Gln
            20

<210> SEQ ID NO 16
<211> LENGTH: 63
<212> TYPE: DNA
<213> ORGANISM: HIV

<400> SEQUENCE: 16
gtcgactcga gacgttcatt atcatatgga ccaggacgtg catttcgtac gcgttggatc    60
cag                                                                  63

<210> SEQ ID NO 17
<211> LENGTH: 1164
<212> TYPE: DNA
<213> ORGANISM: Geobacillus thermoleovorans

<400> SEQUENCE: 17
gcttcacgcg ccaacgatgc gccgattgta cttctccatg gctttactgg ctggggaaga    60
gaagaaatgt ttgggttcaa gtactggggc ggcgtgcgcg cgatatcga acaatggctg    120 aacgacaacg gttatcgaac ttatacgctg gcggtcggac cgctctcgag caactgggac    180
cgggcgtgtg aagcgtatgc tcaacttgtc ggcgggacgg tcgattatgg ggcagcccat    240
gcggcaaagc acggccatgc gcggtttggc cgcacttatc ccggcctgtt gccggaattg    300
aaaaggggtg gccgcatcca tatcatcgcc cacagccaag gggggcagac ggcccgcatg    360
cttgtctcgc tcctagagaa cggaagccaa gaagagcggg agtacgccaa ggcgcacaac    420
gtgtcgttgt caccgttgtt tgaaggtgga catcattttg tgttgagtgt gacgaccatc    480
gccactcctc atgacgggac gacgcttgtc aacatggttg atttcaccga tcgcttttt    540 gacttgcaaa aagcggtgtt ggaagcgcg gctgtcgcca gcaacgtgcc gtacacgagt    600
caagtatacg attttaagct tgaccaatgg ggactgcgcc gccagccggg tgaatcgttc    660
gaccattatt ttgaacggct caagcgctcc cctgtttgga cgtccacaga taccgcccgc    720
tacgatttat ccgtttccgg agctgagaag ttgaatcaat gggtgcaagc aagcccgaat    780
acgtattatt tgagctttgc cacagaacgg acgtatcgcg gagcgctcac aggcaactat    840
tatcccgaac tcggaatgaa tgcattcagc gcggtcgtat gcgctccgtt tctcggttcg    900

```
taccgcaatc cgacgctcgg cattgacgac cgctggcttg aaaacgatgg cattgtcaat    960
acggtttcca tgaacggtcc aaagcgtgga tcaagcgatc ggatcgtacc gtatgacggg   1020
gcgttgaaaa aagggtttg gaatgacatg ggaacgtaca atgtcgacca tttggaaatc   1080
atcggcgttg acccgaatcc gtcatttgat attcgcgcct tttatttgcg acttgccgag   1140
cagttggcga gtttgcggcc ttaa                                          1164
```

<210> SEQ ID NO 18
<211> LENGTH: 387
<212> TYPE: PRT
<213> ORGANISM: Geobacillus thermoleovorans

<400> SEQUENCE: 18

```
Ala Ser Arg Ala Asn Asp Ala Pro Ile Val Leu Leu His Gly Phe Thr
1               5                   10                  15

Gly Trp Gly Arg Glu Glu Met Phe Gly Phe Lys Tyr Trp Gly Gly Val
            20                  25                  30

Arg Gly Asp Ile Glu Gln Trp Leu Asn Asp Asn Gly Tyr Arg Thr Tyr
        35                  40                  45

Thr Leu Ala Val Gly Pro Leu Ser Ser Asn Trp Asp Arg Ala Cys Glu
    50                  55                  60

Ala Tyr Ala Gln Leu Val Gly Gly Thr Val Asp Tyr Gly Ala Ala His
65                  70                  75                  80

Ala Ala Lys His Gly His Ala Arg Phe Gly Arg Thr Tyr Pro Gly Leu
                85                  90                  95

Leu Pro Glu Leu Lys Arg Gly Gly Arg Ile His Ile Ile Ala His Ser
            100                 105                 110

Gln Gly Gly Gln Thr Ala Arg Met Leu Val Ser Leu Leu Glu Asn Gly
        115                 120                 125

Ser Gln Glu Glu Arg Glu Tyr Ala Lys Ala His Asn Val Ser Leu Ser
    130                 135                 140

Pro Leu Phe Glu Gly Gly His His Phe Val Leu Ser Val Thr Thr Ile
145                 150                 155                 160

Ala Thr Pro His Asp Gly Thr Thr Leu Val Asn Met Val Asp Phe Thr
                165                 170                 175

Asp Arg Phe Phe Asp Leu Gln Lys Ala Val Leu Glu Ala Ala Val
            180                 185                 190

Ala Ser Asn Val Pro Tyr Thr Ser Gln Val Tyr Asp Phe Lys Leu Asp
        195                 200                 205

Gln Trp Gly Leu Arg Arg Gln Pro Gly Glu Ser Phe Asp His Tyr Phe
    210                 215                 220

Glu Arg Leu Lys Arg Ser Pro Val Trp Thr Ser Thr Asp Thr Ala Arg
225                 230                 235                 240

Tyr Asp Leu Ser Val Ser Gly Ala Glu Lys Leu Asn Gln Trp Val Gln
                245                 250                 255

Ala Ser Pro Asn Thr Tyr Tyr Leu Ser Phe Ala Thr Glu Arg Thr Tyr
            260                 265                 270

Arg Gly Ala Leu Thr Gly Asn Tyr Tyr Pro Glu Leu Gly Met Asn Ala
        275                 280                 285

Phe Ser Ala Val Val Cys Ala Pro Phe Leu Gly Ser Tyr Arg Asn Pro
    290                 295                 300

Thr Leu Gly Ile Asp Asp Arg Trp Leu Glu Asn Asp Gly Ile Val Asn
305                 310                 315                 320
```

```
Thr Val Ser Met Asn Gly Pro Lys Arg Gly Ser Ser Asp Arg Ile Val
                325                 330                 335

Pro Tyr Asp Gly Ala Leu Lys Lys Gly Val Trp Asn Asp Met Gly Thr
                340                 345                 350

Tyr Asn Val Asp His Leu Glu Ile Ile Gly Val Asp Pro Asn Pro Ser
                355                 360                 365

Phe Asp Ile Arg Ala Phe Tyr Leu Arg Leu Ala Glu Gln Leu Ala Ser
                370                 375                 380

Leu Arg Pro
385

<210> SEQ ID NO 19
<211> LENGTH: 1052
<212> TYPE: PRT
<213> ORGANISM: Bacillus halodurans

<400> SEQUENCE: 19

Ala Met Lys Thr Lys Thr Gly Lys Lys Ile Thr Ala Leu Phe Leu Val
1               5                   10                  15

Phe Met Leu Leu Cys Ser Val Leu Gln Pro Phe Gly Ala Tyr Ala Asn
                20                  25                  30

Ala Leu Gly Ser Ile Asp Thr Ala Thr Pro Ile Thr Lys Gly Gln Glu
                35                  40                  45

Tyr Gln Leu Thr Phe Glu Glu Glu Gln Val His Trp Tyr Lys Ile
                50                  55                  60

Asp Ser Ile Glu Glu Asp Ala Lys Asp Ser His Tyr Gln Ile Gln
65                  70                  75                  80

Leu Thr Ser Glu Asn Glu Met Asn Ile Ser Val Tyr Pro Ser Leu Asp
                85                  90                  95

Arg Ala Lys Ser Asp Asp Thr Tyr Ser Ser Tyr Lys Ser Tyr Ser Met
                100                 105                 110

Leu Gly Glu Thr Gly Lys Ile Asn Phe Pro Leu Ala Trp Thr Gly Pro
                115                 120                 125

Tyr Tyr Ile Lys Val Glu Tyr Tyr Gly Ser Asp Glu Glu Trp Glu Glu
                130                 135                 140

Glu Gly Glu Glu Glu Ser Pro Thr Thr Ala Asp Tyr Thr Leu Ser Phe
145                 150                 155                 160

Glu Gly Ile Lys Leu Pro Pro Ser Thr Gly Met Glu Glu Asp Cys
                165                 170                 175

Pro Val Glu Leu Ser Ala Ser Gln Lys Glu Ser Gly Lys Glu Leu Leu
                180                 185                 190

Lys Ser Leu Arg Thr Ile Arg Asp Gln Val Phe Ser Gln Thr Glu Gln
                195                 200                 205

Gly Lys Glu Phe Thr Ser Leu Tyr Tyr Lys Ala Ala Pro Phe Ile Val
                210                 215                 220

Ser Lys Ile Ala Phe Asp Gln Lys Leu Lys Asp Gln Val Tyr Gln Asp
225                 230                 235                 240

Leu Val Thr Leu Thr Pro Leu Phe Lys Glu Leu Leu Asp Asn Gly Ala
                245                 250                 255

Asn Ser Thr Tyr Lys Ile Thr Lys Lys Asp Gln Asp Ala Ile Leu Arg
                260                 265                 270

Leu Tyr Glu Leu Gly Ala Asp Ser Val Pro His Ser Leu Arg Ala Glu
                275                 280                 285

Met Glu Lys Ile Asn Gln Gln Val Asn Leu Gln Lys Ile Glu Gly Leu
                290                 295                 300
```

```
Arg Leu Ala Thr Val Leu Asp Lys Ala Gly Met Ala Pro Asp Thr Ala
305                 310                 315                 320

Ser Thr Ser Asn Lys Val Ile Val Lys Leu Lys Glu Gly Lys Ser Val
                325                 330                 335

Ser Ala Leu Glu Ala Lys Ala Glu Asp Val Asn Asp Glu Ala Thr Ile
            340                 345                 350

Ser Pro Phe Glu Gln Asp Pro Leu Phe Glu Asp Met Tyr Ile Val
        355                 360                 365

Glu Leu Gly Asp Glu Gln Glu Val Ser Ile Ser Ser Gln Glu Leu Asp
370                 375                 380

Met Thr Val Asp Gln Leu Glu Asn Leu Pro Glu Val Glu Tyr Ala Glu
385                 390                 395                 400

Pro Val Gln Glu Tyr Val Ala Leu Ser Ala Asp Ile His Tyr Ser Asp
                405                 410                 415

Gln Trp Ser Leu Glu Asn Glu Gly Gly Asn Leu Gly Glu Ala Gly Ala
            420                 425                 430

Asp Ile Lys Tyr Ala Pro Leu Gln Glu Leu Val Lys Glu Lys Asn Leu
        435                 440                 445

Pro Asn Thr Leu Ile Ala Val Ile Asp Thr Gly Val Asp Ser Arg Leu
450                 455                 460

Ala Asp Leu Glu Asn Gln Val Arg Thr Asp Leu Gly Tyr Asn Phe Ile
465                 470                 475                 480

Gly Arg Asn Thr Asn Ala Leu Asp Asp Asn Gly His Gly Thr His Val
                485                 490                 495

Ala Gly Ile Ile Ala Ala Glu Ser Asn Asn His Tyr Ser Met Thr Gly
            500                 505                 510

Ile Asn His Ala Ala Glu Ile Pro Ile Lys Val Leu Asp Gly Gly
        515                 520                 525

Gly Ser Gly Asp Thr Glu Ser Ile Ala Ser Gly Ile Lys Tyr Ala Ala
530                 535                 540

Asp Gln Gly Ala Asp Val Ile Asn Leu Ser Leu Gly Gly Ser Tyr Ser
545                 550                 555                 560

Arg Val Ile Glu Ala Ser Leu Lys Tyr Ala Ser Glu Lys Gly Val Thr
                565                 570                 575

Ile Val Ala Ala Ser Gly Asn Glu Tyr Ser Pro Tyr Leu Ser Tyr Pro
            580                 585                 590

Ala Ser Ser Arg Tyr Val Ile Ser Val Gly Ala Thr Asn Arg Ser Asp
        595                 600                 605

Ile Val Ser Asp Tyr Ser Asn Tyr Gly Lys Gly Leu Asp Leu Val Ala
610                 615                 620

Pro Gly Thr Asp Ile Pro Ser Leu Leu Pro Asn Gly Asn Val Thr Tyr
625                 630                 635                 640

Phe Asp Gly Thr Ser Met Ala Ala Pro His Val Ala Val Ala Gly
                645                 650                 655

Leu Leu Leu Ser Gln Asn Ala Lys Leu Ser Ser Glu Asp Ile Gln Lys
            660                 665                 670

Ile Leu Thr Glu Thr Thr Asp Tyr Ile Ala Phe Glu Glu Leu Asp Asn
        675                 680                 685

Glu Glu Asp Tyr Tyr Phe Tyr Tyr Asp Asp Glu Glu Pro Val Leu
690                 695                 700

Leu Pro Gly Tyr Asp Glu Ala Ser Gly Trp Gly Arg Leu Asn Ala His
705                 710                 715                 720
```

```
Ser Ala Val Ser Ala Val Asp Leu Asn Val Lys Val Asn Arg Leu Leu
            725                 730                 735

Asp Asn Gln Asn Val Val Thr Gly Ser Ala Lys Lys Gly Thr Thr Ile
        740                 745                 750

Glu Val Thr Asn Gly Ser Glu Thr Leu Gly Ser Gly Pro Val Asp Ala
            755                 760                 765

Asn Gly Lys Phe Lys Val Lys Ile Pro Val Gln Pro Ala Asn Gln Val
    770                 775                 780

Leu Tyr Val Lys Ala Ser Gln Gly Ala Ala Lys Ala Ser Ile Arg Ile
785                 790                 795                 800

Ala Val Glu Glu Gly Lys Lys Pro Lys Ala Pro Lys Val Asn Thr Val
                805                 810                 815

Ser Asn Lys Asp Thr His Val Thr Gly Thr Thr Glu Pro Asn Leu Thr
            820                 825                 830

Val Asn Val Lys Asp Lys Asn Lys Lys Val Ile Ala Thr Gly Lys Ala
        835                 840                 845

Asp Lys Asn Gly Ala Phe Lys Val Lys Ile Asn Lys Gln Lys Glu Asn
    850                 855                 860

Thr Thr Leu Tyr Val Thr Ala Met Asp Leu Gly Asn Lys Glu Ser Lys
865                 870                 875                 880

Ala Val Lys Ile Lys Val Ile Asp Lys Ile Pro Pro Lys Ala Pro Lys
                885                 890                 895

Val Asn Ser Ile Ser Asp Arg Thr Thr Thr Val Lys Gly Glu Thr Glu
            900                 905                 910

Pro Asn Ala Thr Val Thr Ile Lys Lys Asn Gly Lys Lys Leu Ala Ser
        915                 920                 925

Gly Lys Ala Asp Lys Asn Gly Lys Phe Ser Ile Lys Ile Ser Lys Gln
    930                 935                 940

Lys Ala Gly Thr Lys Leu Ser Ile Thr Ala Lys Asp Lys Ala Gly Asn
945                 950                 955                 960

Val Ser Lys Ala Thr Thr Lys Thr Val Lys Asp Lys Thr Pro Pro Lys
                965                 970                 975

Lys Pro Thr Val Asn Lys Val Thr Ser Arg Asp Lys Val Thr Gly Lys
            980                 985                 990

Thr Glu Ala Asn Ala Thr Val Thr Ile Lys Arg Asp Gly Lys Thr Leu
        995                 1000                1005

Ala Ser  Gly Lys Ala Asp  Lys Asn Gly Lys Phe Ser  Ile Lys Ile
    1010                 1015                1020

Ser Lys  Gln Lys Lys Gly Thr  Lys Leu Ser Val Thr  Ala Lys Asp
    1025                 1030                1035

Lys Ala  Gly Asn Thr Ser Lys  Ala Thr Lys Val Thr  Val Gln
    1040                 1045                1050

<210> SEQ ID NO 20
<211> LENGTH: 12
<212> TYPE: PRT
<213> ORGANISM: artificial sequence
<220> FEATURE:
<223> OTHER INFORMATION: Ag binding polypeptide

<400> SEQUENCE: 20

Asn Pro Ser Ser Leu Phe Thr Tyr Leu Pro Ser Asp
1               5                   10

<210> SEQ ID NO 21
<211> LENGTH: 9
```

```
<212> TYPE: PRT
<213> ORGANISM: artificial sequence
<220> FEATURE:
<223> OTHER INFORMATION: Pb binding polypeptide

<400> SEQUENCE: 21

Cys Ser Val Thr Gln Asn Lys Tyr Cys
1               5

<210> SEQ ID NO 22
<211> LENGTH: 9
<212> TYPE: PRT
<213> ORGANISM: artificial sequence
<220> FEATURE:
<223> OTHER INFORMATION: PB binding polypeptide

<400> SEQUENCE: 22

Cys Ser Pro His Pro Gly Pro Tyr Cys
1               5

<210> SEQ ID NO 23
<211> LENGTH: 9
<212> TYPE: PRT
<213> ORGANISM: artificial sequence
<220> FEATURE:
<223> OTHER INFORMATION: PB binding polypeptide

<400> SEQUENCE: 23

Cys His Ala Pro Thr Pro Met Leu Cys
1               5

<210> SEQ ID NO 24
<211> LENGTH: 9
<212> TYPE: PRT
<213> ORGANISM: artificial sequence
<220> FEATURE:
<223> OTHER INFORMATION: Pt binding polypeptide

<400> SEQUENCE: 24

Cys Asp Arg Thr Ser Thr Trp Arg Cys
1               5

<210> SEQ ID NO 25
<211> LENGTH: 9
<212> TYPE: PRT
<213> ORGANISM: artificial sequence
<220> FEATURE:
<223> OTHER INFORMATION: Pt binding polypetide

<400> SEQUENCE: 25

Cys Gln Ser Val Thr Ser Thr Lys Cys
1               5

<210> SEQ ID NO 26
<211> LENGTH: 9
<212> TYPE: PRT
<213> ORGANISM: artificial sequence
<220> FEATURE:
<223> OTHER INFORMATION: Pt binding sequence

<400> SEQUENCE: 26

Cys Ser Ser Ser His Leu Asn Lys Cys
1               5

<210> SEQ ID NO 27
<211> LENGTH: 12
<212> TYPE: PRT
```

```
<213> ORGANISM: artificial sequence
<220> FEATURE:
<223> OTHER INFORMATION: Ti binding polypeptide

<400> SEQUENCE: 27

Arg Lys Leu Pro Asp Ala Pro Gly Met His Thr Trp
1               5                   10

<210> SEQ ID NO 28
<211> LENGTH: 39
<212> TYPE: DNA
<213> ORGANISM: artificial sequence
<220> FEATURE:
<223> OTHER INFORMATION: His nucleotide sequence

<400> SEQUENCE: 28
gccgactcga gacatcatca tcatcatcac aggatccga                               39

<210> SEQ ID NO 29
<211> LENGTH: 13
<212> TYPE: PRT
<213> ORGANISM: artificial sequence
<220> FEATURE:
<223> OTHER INFORMATION: His polypetide

<400> SEQUENCE: 29

Ala Asp Ser Arg His His His His His His Arg Ile Arg
1               5                   10

<210> SEQ ID NO 30
<211> LENGTH: 21
<212> TYPE: DNA
<213> ORGANISM: artificial sequence
<220> FEATURE:
<223> OTHER INFORMATION: Primer IF

<400> SEQUENCE: 30
gctgagtctc gtatccgtga c                                                 21

<210> SEQ ID NO 31
<211> LENGTH: 21
<212> TYPE: DNA
<213> ORGANISM: artificial sequence
<220> FEATURE:
<223> OTHER INFORMATION: Primer IR

<400> SEQUENCE: 31
cctgcagcat cgtctcctgc a                                                 21

<210> SEQ ID NO 32
<211> LENGTH: 25
<212> TYPE: DNA
<213> ORGANISM: artificial sequence
<220> FEATURE:
<223> OTHER INFORMATION: Primer UPFor (BamHI)

<400> SEQUENCE: 32
gcggatccgt gtggtgacat ttgac                                             25

<210> SEQ ID NO 33
<211> LENGTH: 28
<212> TYPE: DNA
<213> ORGANISM: artificial sequence
<220> FEATURE:
<223> OTHER INFORMATION: Primer UPrev (XbaI)

<400> SEQUENCE: 33
```

```
gctctagacg atgcgcattc attgctgg                                           28

<210> SEQ ID NO 34
<211> LENGTH: 24
<212> TYPE: DNA
<213> ORGANISM: artificial sequence
<220> FEATURE:
<223> OTHER INFORMATION: Primer DownFor (XbaI)

<400> SEQUENCE: 34
gctctagaga gtctcgtatc cgtg                                               24

<210> SEQ ID NO 35
<211> LENGTH: 24
<212> TYPE: DNA
<213> ORGANISM: artificial sequence
<220> FEATURE:
<223> OTHER INFORMATION: Primer DownRev (PstI)

<400> SEQUENCE: 35
cgctgcagaa gaggaacgta aacg                                               24

<210> SEQ ID NO 36
<211> LENGTH: 21
<212> TYPE: DNA
<213> ORGANISM: artificial sequence
<220> FEATURE:
<223> OTHER INFORMATION: Primer FliCR

<400> SEQUENCE: 36
caacaaagta acggttgagc g                                                  21

<210> SEQ ID NO 37
<211> LENGTH: 21
<212> TYPE: DNA
<213> ORGANISM: artificial sequence
<220> FEATURE:
<223> OTHER INFORMATION: Primer InvR

<400> SEQUENCE: 37
cctgcagcat cgtctcctgc a                                                  21

<210> SEQ ID NO 38
<211> LENGTH: 30
<212> TYPE: DNA
<213> ORGANISM: artificial sequence
<220> FEATURE:
<223> OTHER INFORMATION: Primer SigDF

<400> SEQUENCE: 38
ctcggtaccc tcgcgttacg ctctttctgt                                         30

<210> SEQ ID NO 39
<211> LENGTH: 19
<212> TYPE: DNA
<213> ORGANISM: artificial sequence
<220> FEATURE:
<223> OTHER INFORMATION: Primer M13R

<400> SEQUENCE: 39
ggaaacagct atgaccatg                                                     19

<210> SEQ ID NO 40
<211> LENGTH: 28
<212> TYPE: DNA
```

<213> ORGANISM: artificial sequence
<220> FEATURE:
<223> OTHER INFORMATION: Primer CterF

<400> SEQUENCE: 40
cgcgaattcc taggagctat gcaaaacc                                              28

<210> SEQ ID NO 41
<211> LENGTH: 26
<212> TYPE: DNA
<213> ORGANISM: artificial sequence
<220> FEATURE:
<223> OTHER INFORMATION: Primer FliN-terRev

<400> SEQUENCE: 41
ctcctcgagc gaccttctga aacagc                                                26

<210> SEQ ID NO 42
<211> LENGTH: 30
<212> TYPE: DNA
<213> ORGANISM: artificial sequence
<220> FEATURE:
<223> OTHER INFORMATION: Primer SigDKpn

<400> SEQUENCE: 42
ctcggtaccc tcgcgttacg ctctttctgt                                            30

<210> SEQ ID NO 43
<211> LENGTH: 48
<212> TYPE: DNA
<213> ORGANISM: artificial sequence
<220> FEATURE:
<223> OTHER INFORMATION: Primer CterF2

<400> SEQUENCE: 43
cacgaattct cgagcccggg atcctcttca ctaggagcta tgcaaaac                        48

<210> SEQ ID NO 44
<211> LENGTH: 30
<212> TYPE: DNA
<213> ORGANISM: artificial sequence
<220> FEATURE:
<223> OTHER INFORMATION: Primer VNR2

<400> SEQUENCE: 44
cggcagctgt tcaccagaat tagcaccaac                                            30

<210> SEQ ID NO 45
<211> LENGTH: 49
<212> TYPE: DNA
<213> ORGANISM: artificial sequence
<220> FEATURE:
<223> OTHER INFORMATION: Primer VCF

<400> SEQUENCE: 45
cacgtcgact cgagcccggg atccttaatt gaacttgatt taacaaaag                       49

<210> SEQ ID NO 46
<211> LENGTH: 45
<212> TYPE: DNA
<213> ORGANISM: artificial sequence
<220> FEATURE:
<223> OTHER INFORMATION: Primer NC5F

<400> SEQUENCE: 46
cacgtcgact cgagcccggg atcctttaat acgcaaaaat tactc                           45

<210> SEQ ID NO 47
<211> LENGTH: 28
<212> TYPE: DNA
<213> ORGANISM: artificial sequence
<220> FEATURE:
<223> OTHER INFORMATION: Primer NC5R

<400> SEQUENCE: 47
cacctcgagt gagttgtatc tttgattc                                28

<210> SEQ ID NO 48
<211> LENGTH: 30
<212> TYPE: DNA
<213> ORGANISM: artificial sequence
<220> FEATURE:
<223> OTHER INFORMATION: Primer VNR6

<400> SEQUENCE: 48
gacgtcgaca gtgtggtcag taatatcctc                              30

<210> SEQ ID NO 49
<211> LENGTH: 51
<212> TYPE: DNA
<213> ORGANISM: artificial sequnce
<220> FEATURE:
<223> OTHER INFORMATION: Primer VCF6

<400> SEQUENCE: 49
cacgtcgact cgagcccggg atggatccag aatgcacaat cagctattga c      51

<210> SEQ ID NO 50
<211> LENGTH: 26
<212> TYPE: DNA
<213> ORGANISM: artificial sequence
<220> FEATURE:
<223> OTHER INFORMATION: Primer N-For

<400> SEQUENCE: 50
gcgagctctg cagcgtacta caacca                                  26

<210> SEQ ID NO 51
<211> LENGTH: 26
<212> TYPE: DNA
<213> ORGANISM: artificial sequence
<220> FEATURE:
<223> OTHER INFORMATION: Primer N-Rev

<400> SEQUENCE: 51
gcggatccag ctgataacgc tacgta                                  26

<210> SEQ ID NO 52
<211> LENGTH: 28
<212> TYPE: DNA
<213> ORGANISM: artificial sequnce
<220> FEATURE:
<223> OTHER INFORMATION: Primer C-For

<400> SEQUENCE: 52
gcggatccta gcggacctgt agatgcta                                28

<210> SEQ ID NO 53
<211> LENGTH: 27
<212> TYPE: DNA
<213> ORGANISM: artificial sequence
<220> FEATURE:

<223> OTHER INFORMATION: Primer C-Rev

<400> SEQUENCE: 53
ggtctagatg ccttgtcctt cgctgta                                27

<210> SEQ ID NO 54
<211> LENGTH: 26
<212> TYPE: DNA
<213> ORGANISM: artificial sequence
<220> FEATURE:
<223> OTHER INFORMATION: Oligonucleotide HisF3

<400> SEQUENCE: 54
tcgagacatc atcatcatca tcacag                                 26

<210> SEQ ID NO 55
<211> LENGTH: 26
<212> TYPE: DNA
<213> ORGANISM: artificial sequence
<220> FEATURE:
<223> OTHER INFORMATION: Oligonucleotide HisR3

<400> SEQUENCE: 55
gatcctgtga tgatgatgat gatgtc                                 26

<210> SEQ ID NO 56
<211> LENGTH: 26
<212> TYPE: DNA
<213> ORGANISM: artificial sequence
<220> FEATURE:
<223> OTHER INFORMATION: Annealed oligonucleotide [Bam HI]

<400> SEQUENCE: 56
tcgagacatc atcatcatca tcacag                                 26

<210> SEQ ID NO 57
<211> LENGTH: 26
<212> TYPE: DNA
<213> ORGANISM: artificial sequence
<220> FEATURE:
<223> OTHER INFORMATION: Annealed oligonucleotide [XhoI]

<400> SEQUENCE: 57
ctgtagtagt agtagtagtg tcctag                                 26

<210> SEQ ID NO 58
<211> LENGTH: 63
<212> TYPE: DNA
<213> ORGANISM: artificial sequence
<220> FEATURE:
<223> OTHER INFORMATION: Oligonucleotide HivF3B

<400> SEQUENCE: 58
cacctcgaga cgttcattat catatggacc aggacgtgca tttcgtacgc gttggatcca    60
cag                                                                 63

<210> SEQ ID NO 59
<211> LENGTH: 63
<212> TYPE: DNA
<213> ORGANISM: artificial sequence
<220> FEATURE:
<223> OTHER INFORMATION: Oligonucleotide HivR3B

<400> SEQUENCE: 59
ctgtggatcc aacgcgtacg aaatgcacgt cctggtccat atgataatga acgtctcgag    60

```
gtg                                                             63

<210> SEQ ID NO 60
<211> LENGTH: 50
<212> TYPE: DNA
<213> ORGANISM: artificial sequence
<220> FEATURE:
<223> OTHER INFORMATION: Annealed oligonucleotide [BamHI]

<400> SEQUENCE: 60
tcgagacgtt cattatcata tggaccagga cgtgcatttc gtacgcgttg          50

<210> SEQ ID NO 61
<211> LENGTH: 50
<212> TYPE: DNA
<213> ORGANISM: artificial sequence
<220> FEATURE:
<223> OTHER INFORMATION: Annealed oligonucleotide [Xho I]

<400> SEQUENCE: 61
ctgcaagtaa tagtatacct ggtcctgcac gtaaagcatg cgcaaccatg          50

<210> SEQ ID NO 62
<211> LENGTH: 28
<212> TYPE: DNA
<213> ORGANISM: artificial sequence
<220> FEATURE:
<223> OTHER INFORMATION: Primer LipFSD

<400> SEQUENCE: 62
gtcctcgagg cttcgcgagc caacgatg                                  28

<210> SEQ ID NO 63
<211> LENGTH: 26
<212> TYPE: DNA
<213> ORGANISM: artificial sequence
<220> FEATURE:
<223> OTHER INFORMATION: Primer LipR

<400> SEQUENCE: 63
gtcggatcca ggcccgaagc tcgcca                                    26
```

GRAM POSITIVE BACTERIAL CELLS COMPRISING A DISRUPTED FLAGELLIN GENE, FLAGELLIN-BASED FUSION PROTEINS AND USE IN REMOVAL OF METAL IONS FROM A LIQUID

RELATED APPLICATIONS

This is a U.S. national phase application of International Application no. PCT/IB2005/054022 filed 2 Dec. 2005, claiming priority from South Africa Application No. 2004/9786 filed 2 Dec. 2004, the contents of each are hereby incorporated by reference in their entirety.

REFERENCE TO SEQUENCE LISTING

Reference is hereby made to the Sequence Listing submitted in triplicate on three identical compact discs (COPY 1, COPY 2, and CRF) in connection with this patent application. Each compact disc contains one file named "F19735 KWM.ST25.txt," 35,662 bytes in size, with a created date of Jan. 12, 2007. The material of each of these submitted compact discs is hereby incorporated by reference in its entirety.

TECHNICAL FIELD

This invention relates to recombinant proteins, and more particularly to recombinant proteins produced by gram positive bacteria.

BACKGROUND

Bacterial recombinant protein production is most commonly performed in gram negative bacteria and, in particular, *Escherichia coli* bacteria. There is a need to develop methods of producing recombinant proteins and peptides in Gram positive bacteria.

SUMMARY

The inventors have developed strains of gram positive *Bacillus halodurans* ALK36 bacteria deposited under accession number NCIMB41348 transformed to produce and express on their surfaces fusion proteins composed of flagellin and, within the flagellin amino acid sequence, any of a variety of heterologous polypeptides. These recombinant bacteria produce high levels of stable and soluble recombinant protein on the surface of the recombinant bacterial cells. They have also developed genetic constructs containing flagellin-encoding nucleotide sequences and sites within the flagellin-encoding nucleotide sequences into which nucleotide sequences encoding heterologous polypeptides can be inserted. The invention features modified bacterial lines suitable for producing the flagellin-based fusion proteins (FBFP) of the invention, constructs useful for making the fusion proteins, FBFP, nucleic acids encoding FBFP, vectors containing the nucleic acids, cells containing the vectors, transformed bacterial lines expressing FBFP, and methods of making and using the FBFP.

More specifically, the invention features a substantially pure culture of bacterial cells, a substantial number of which comprise a disrupted flagellin gene, the disruption preventing expression of functional flagellin. The invention also includes an isolated bacterial cell that contains a disrupted flagellin gene, the disruption preventing expression of functional flagellin. In both cases, the disruption can be by replacement of the endogenous gene in the substantial number of the bacterial cells with a DNA sequence encoding no polypeptide or a non-functional flagellin polypeptide. The bacterial cells can be gram positive bacterial cells, e.g., *Bacillus* cells such as *B. halodurans* cells. The cell may be of the strain BhFC01 (hag). The non-functional flagellin polypeptide can lack amino acids 14 to 226 of SEQ ID NO:2.

In addition to comprising a disrupted flagellin gene, at least one cell wall protease gene of a substantial number of the bacterial cells or the isolated bacterial cell can be disrupted and the disruption can be by replacement of the endogenous gene in the substantial number of bacterial cells with a DNA sequence encoding either no polypeptide or a non-functional cell wall protease polypeptide. The bacterial cell(s) can be those listed above. The at least one cell wall protease gene can be a wrpA gene and the disruption can include deletion of the entire coding sequence of cell wall protease gene. The cells can be BhFC04 (hag, wprA) cells deposited under Accession Number 41357 at the NCIMB on 28 Nov. 2005.

Another aspect of the invention is a method of genetically engineering a bacterium of the genus *Bacillus*. The method includes disrupting the hag gene in the chromosome of the bacterium, the disruption preventing expression of functional flagellin by the gene. The *Bacillus* bacterium can be a *Bacillus halodurans* bacterium.

The method may further comprise disrupting one or more genes encoding one or more cell wall proteases, the disruption preventing expression of the one or more functional cell wall proteases by the one or more genes. The one or more cell wall protease genes can include the wrpA gene.

Also embraced by the invention is a fusion protein that contains: all or part of bacterial flagellin protein, the part of the flagellin protein including the N-terminal and C-terminal conserved regions of the flagellin protein; and a heterologous polypeptide within, or replacing, the variable region of the flagellin protein. The fusion protein has the ability, if made by a bacterial cell, to be expressed on the surface of the bacterial cell. The heterologous polypeptide can a polypeptide having the ability to bind to a metal ion. The metal ion may be nickel, copper, cadmium, platinum, palladium, titanium, silver, or gold, and the heterologous polypeptide may be a polyhistidine sequence. The polyhistidine sequence may contain six histidine residues.

In addition, the heterologous polypeptide may be an enzyme or a functional fragment of an enzyme. The enzyme may be a lipase enzyme, e.g., *G. thermoleovorans* lipase A. The enzyme may be a hydrolytic enzyme, e.g., an amylase, a protease, an esterase, or a cellulase. Moreover, the heterologous polypeptide may be an immunogen.

The fusion protein may further include one to fifteen linker residues N-terminal of the N-terminus of the heterologous polypeptide and/or one to fifteen linker residues C-terminal of the C-terminus of the heterologous polypeptide. It may also include cleavable sites N-terminal of the N-terminus of the heterologous polypeptide and C-terminal of the C-terminus of the heterologous polypeptide.

The invention also provides: a nucleic acid encoding the above-described fusion protein; a vector including the nucleic acid sequence, e.g., a vector in which nucleic acid sequence is operably linked to a transcriptional regulatory element (TRE); and an isolated cell containing the vector. The cell may be a prokaryotic cell, e.g., a bacterial cell. The bacterial cell may be a gram positive bacterial cell such as a cell of the *Bacillus* genus, e.g., a cell of the *B. halodurans* species. The cell may be of the strain BhFC04 (hag, wprA) deposited under Accession Number 41357 at the NCIMB on 28 Nov. 2005.

In another aspect the invention embraces a method of making a fusion protein. The method may include culturing a cell containing a vector that includes a nucleic acid encoding the above-described fusion protein, the nucleic acid being operably linked to a TRE, and obtaining the fusion protein from the culture.

Also featured by the invention is a DNA construct that contains: all or part of the coding sequence for a bacterial flagellin polypeptide, the part of the coding sequence including nucleotides encoding the N-terminal and C-terminal conserved regions of the flagellin protein; and, inserted into, or replacing, the sequence encoding the variable region of the flagellin polypeptide, a nucleotide sequence that includes at least one restriction enzyme site. The bacterial flagellin polypeptide may be a *Bacillus* flagellin polypeptide, e.g., *B. halodurans* flagellin (SEQ ID NO:1). In the construct, the nucleotide sequence may be inserted immediately after any nucleotide between nucleotide 162 and nucleotide 606 of SEQ ID NO:1; immediately after any nucleotide between nucleotide 441 and nucleotide 570 of SEQ ID NO:1; or immediately after any nucleotide between nucleotide 459 and nucleotide 540 of SEQ ID NO:1.

Also provided by the invention is a method of removing one or more metal ions from a liquid. The method may involve: contacting a liquid containing one or more metal ions with a fusion protein of the invention, the heterologous polypeptide in the fusion protein being a polypeptide that binds to one or more of said metal ions. The liquid may be contacted with a bacterial cell expressing the fusion protein. Alternatively, the fusion protein may be a cell-free polypeptide.

Another method of the invention is one for isolating one or more metal ions from a liquid containing the one or more metal ions. The method may include: contacting a liquid containing one or more metal ions with a fusion protein of the invention, the heterologous polypeptide in the fusion protein being a polypeptide that binds to the one or more metal ions, the contacting resulting in binding of the one more metal ions to the fusion protein; and separating the one or more metal ions from the fusion protein.

Another aspect of the invention is method of converting a substrate to a product, which method includes: contacting an enzyme substrate with a fusion protein of the invention, the heterologous polypeptide in the fusion protein being an enzyme or a functional fragment of the enzyme for the enzyme substrate thereby converting said substrate into said product.

The invention also extends to use of a fusion protein of the invention in the manufacture of a preparation for generating an immune response in a mammalian subject.

The invention extends further to a substance or composition for use in a method of generating an immune response in a mammalian subject, said substance or composition comprising a fusion protein of the invention, and said method comprising administering an effective amount of said substance or composition to said mammalian subject.

Also embraced by the invention is a method of generating an immune response. The method may include administering the fusion protein of the invention to a mammalian subject, the heterologous polypeptide in the fusion protein being an immunogen. The mammalian subject may be, for example, a human.

The invention also provides a kit that contains an expression vector that contains a DNA construct of the invention. The kit may further include: at least one restriction enzyme; a host cell, the host cell being a cell in which the vector is capable of replicating; and/or instructions for inserting a nucleic acid sequence encoding a heterologous polypeptide into the DNA construct.

"Polypeptide" and "protein" are used interchangeably and mean any peptide-linked chain of amino acids, regardless of length or post-translational modification.

As used herein, the term "isolated" as applied to a polypeptide refers to a polypeptide which either has no naturally-occurring counterpart or has been separated or purified from components which naturally accompany it, e.g., microorganism cellular components such as bacterial cell cellular components. Typically, the polypeptide is considered "isolated" when it is at least 70%, by dry weight, free from the proteins and other naturally-occurring organic molecules with which it is naturally associated. Preferably, a preparation of a polypeptide (or peptide fragment thereof) of the invention is at least 80%, more preferably at least 90%, and most preferably at least 99%, by dry weight, the polypeptide (or the peptide fragment thereof), respectively, of the invention. Thus, for example, a preparation of polypeptide x is at least 80%, more preferably at least 90%, and most preferably at least 99%, by dry weight, polypeptide x. Since a polypeptide that is chemically synthesized is, by its nature, separated from the components that naturally accompany it, the synthetic polypeptide is "isolated." Moreover, since fusion proteins such as the FBFP of the invention do not exist in nature, they are always "isolated."

An isolated polypeptide of the invention may be obtained, for example, by expression of a recombinant nucleic acid encoding the polypeptide or by chemical synthesis. A polypeptide that is produced in a cellular system different from the source from which it naturally originates is "isolated," because it will necessarily be free of components which naturally accompany it. The degree of isolation or purity can be measured by any appropriate method, e.g., column chromatography, polyacrylamide gel electrophoresis, or HPLC analysis.

An "isolated nucleic acid", such as an isolated DNA, is either (1) a nucleic acid that contains sequence not identical to that of any naturally occurring sequence, or (2), in the context of a nucleic acid with a naturally-occurring sequence (e.g., a cDNA or genomic DNA), a nucleic acid free of at least one of the genes that flank the gene containing the nucleic acid of interest in the genome of the organism in which the gene containing the nucleic acid of interest naturally occurs. The term therefore includes a recombinant nucleic incorporated into a vector, into an autonomously replicating plasmid or virus, or into the genomic DNA of a prokaryote or eukaryote. The term also includes a separate molecule such as: a cDNA where the corresponding genomic DNA may include introns and therefore can have a different sequence; a genomic fragment that lacks at least one of the flanking genes; a fragment of cDNA or genomic DNA produced by polymerase chain reaction (PCR) and that lacks at least one of the flanking genes; a restriction fragment that lacks at least one of the flanking genes; a nucleic acid encoding a non-naturally occurring protein such as a fusion protein, mutein, or fragment of a given protein; and a nucleic acid which is a degenerate variant of a cDNA or a naturally occurring nucleic acid. In addition, it includes a recombinant nucleotide sequence that is part of a hybrid gene, i.e., a gene encoding a non-naturally occurring fusion protein. It will be apparent from the foregoing that isolated DNA does not mean a DNA present among hundreds to millions of other DNA molecules within, for example, cDNA or genomic DNA libraries or genomic DNA restriction digests in, for example, a restriction digest reaction mixture or an electrophoretic gel slice.

As used herein, "operably linked" means incorporated into a genetic construct so that an expression control sequence (transcriptional or translational regulatory element) effectively controls expression of a coding sequence of interest.

The term "endogenous" as used herein with reference to nucleic acids or genes and a particular cell refers to any nucleic acid or gene that does occur in (and can be obtained from) that particular cell as found in nature.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. All publications, patent applications, patents and other references mentioned herein are incorporated by reference in their entirety. The materials, methods, and examples disclosed herein are illustrative only and not intended to be limiting.

Other features and advantages of the invention, e.g., FBFP useful for bioremediation or biomining, and as immunogens, will be apparent from the following description, from the drawings and from the claims.

DESCRIPTION OF DRAWINGS

FIG. 3 is a depiction of a nucleotide sequence alignment of the putative hag coding region cloned from B. halodurans Alk36 (SEQ ID NO:1) with the corresponding coding region of the hag gene from Bacillus sp. C-125 (SEQ ID NO:1).

FIG. 6 is a depiction of the complete nucleotide sequence of the B. halodurans Alk36 hag gene including the regions flanking the coding sequence (SEQ ID NO:5). The boxed nucleotides represent the putative promoter regions and potential ribosome binding site. The white nucleotides are different to those of the hag gene from Bacillus halodurans C125. The shaded nucleotides show all the new sequence obtained from the iPCR. The coding region of the gene (SEQ ID NO:1) is shown in bold.

FIG. 7 is a depiction of the nucleotide sequence of the B. halodurans Alk36 hag gene including up- and downstream regions (SEQ ID NO:5). The boxed nucleotides represent the putative promoter regions. The underlined nucleotides represent a potential ribosome binding (Shine-Dalgarno) site. Also shown is the complete amino acid sequence (SEQ ID NO:2) of B. halodurans Alk36 flagellin.

The sequence indicates the deleted region of the hag open reading frame and sequence the remainder of the open reading frame in the construction of pSECFlg-. Primers used are underlined.

Figure 9B:
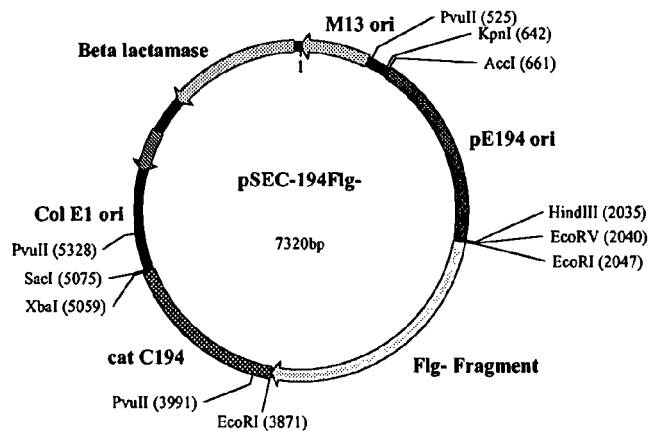
FIG. 9A is a depiction of the nucleotide sequence of the B. halodurans Alk36 hag gene with its up- and down-stream regions (SEQ ID NO:6) indicating how the defective hag gene was constructed. The black sequence indicates the deleted region of the hag open reading frame and the grey shaded sequences indicate the two fragments, N-terminal and C-terminal (containing bits of coding region as well as up- and downstream sequence) which were obtained from PCR reactions and ligated together to create the defective hag gene used in the construction of pSECFlg-. Sequences corresponding to PCR primers are white.

FIG. 9B is a depiction of the pSEC194Flg- plasmid map.

Figure 10:
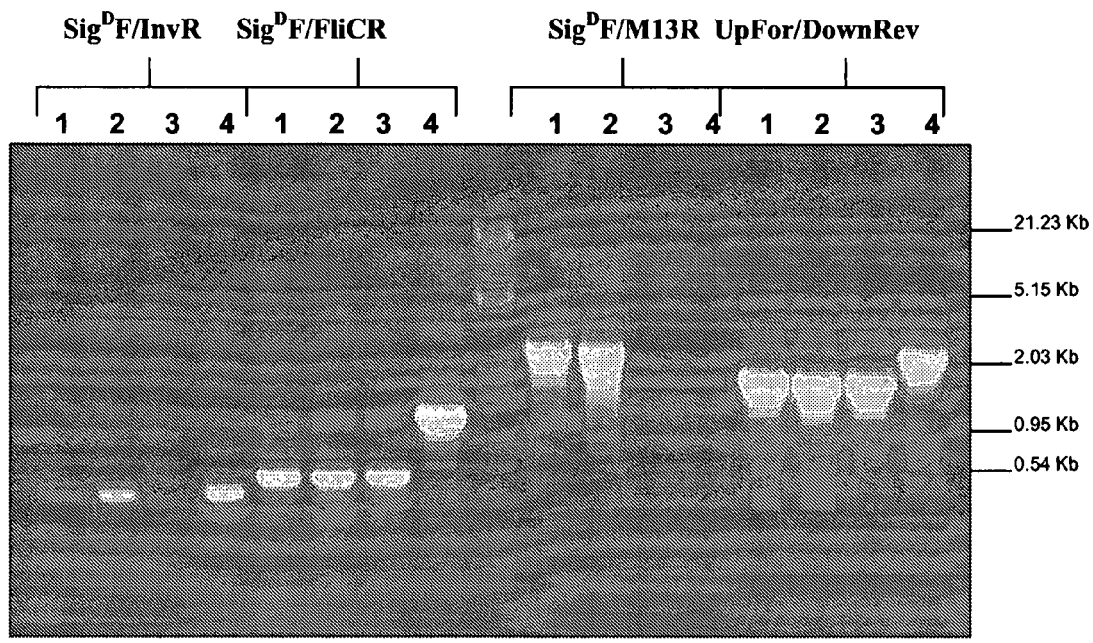

FIG. 10 is a photograph of an ethidium bromide-stained agarose (0.8%) electrophoretic gel showing the PCR-determined results of integration events of pSEC194Flg- in the B. halodurans Alk36 chromosome. Different primer sets (A, B, C and D) were used to test the different integration events. Lane 1, sco, mutant 49; lane 2, sco, mutant 50; lane 3, dco, non-motile mutant −BhFC01 (derived from 49); and lane 4, B. halodurans Alk36 chromosomal DNA. The lane between primer sets B and C contains size markers. The positions of size (in Kb) markers are indicated on the right side of the photograph.

FIG. 11 is a depiction of a comparison of the secondary structure of the proteins encoded by NC1, NC2, NC3, NC5, and NC6 as predicted by PSI-Pred software. This program was used to generate a 3-state prediction for each protein. The secondary structures α-helix (H), extended β-strand (E) and coil (C) are indicated. Amino acid insertions are indicated in bold and grey blocks.

FIG. 12A is a depiction of the amino acid sequence (SEQ ID NO:7) of the NC2 peptide and the nucleotide sequence (SEQ ID NO:8) encoding it.

FIG. 12B is a depiction of the amino acid sequence (SEQ ID NO:9) of the NC3 peptide and the nucleotide sequence (SEQ ID NO:10) encoding it FIG. 12C is a depiction of the amino acid sequence (SEQ ID NO:11) of the NC5 peptide and the nucleotide sequence (SEQ ID NO:12) encoding it.

FIG. 12D is a depiction of the amino acid sequence (SEQ ID NO:13) of the NC6 peptide and the nucleotide sequence (SEQ ID NO:14) encoding it.

Figure 13A:
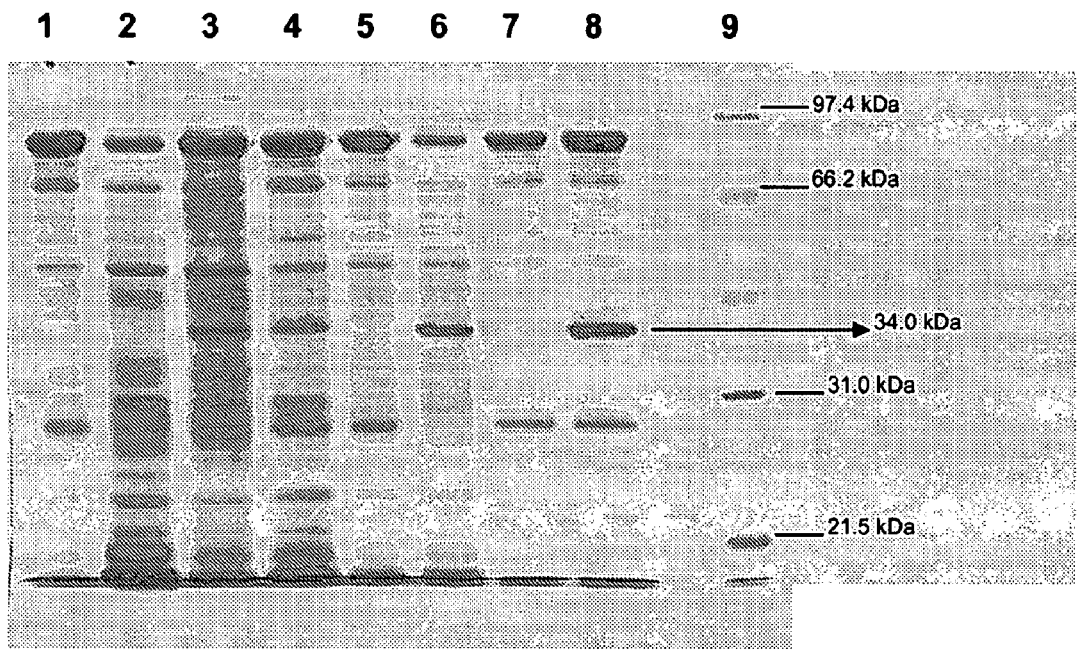

FIG. 13A is photograph of a Coomassie blue-stained SDS-PAGE gel containing cell-surface protein fractions. Lanes 1-7, *B. halodurans* strain BhFC01 transformed with various genetic constructs. Lane 1, NC1; lane 2, NC2; lane 3, NC3; lane 4, NC3sco; lane 5, NC5; lane 6, FliC; lane 7, BhFC01; lane 8, *B. halodurans* Alk3 WT (wild-type); lane 9, molecular weight markers. The positions of various molecular weight (in kDa) markers are indicated on the right of the photograph. The arrow on the right of the photograph indicates the position of an over-expressed 34 kDa protein.

Figure 13B:
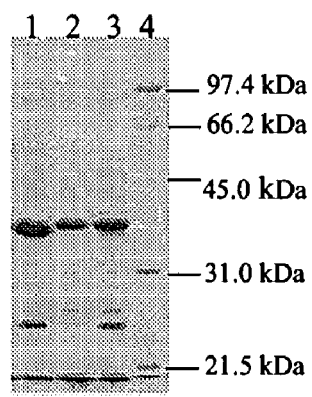

FIG. 13B is photograph of a Coomassie blue-stained SDS-PAGE gel containing CS proteins extracted from: lane 1, *B. halodurans* Alk36; lane 2, strain BhFC01 pSEC194NC3; lane 3, strain BhFC01 pSEC194NC6; and lane 4, molecular weight markers. The positions of various molecular weight (in kDa) markers are indicated on the right of the photograph.

Figure 13C:
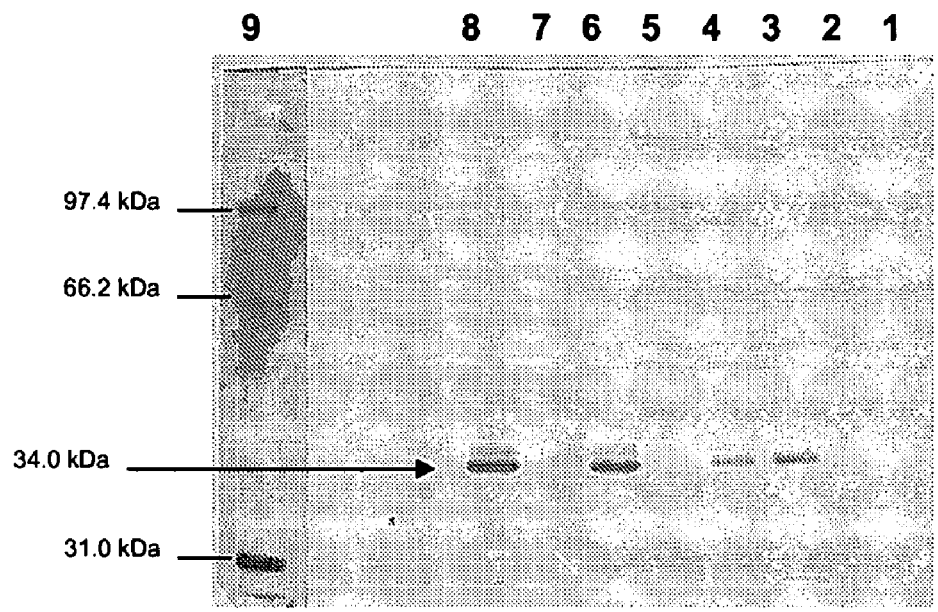

FIG. 13C is a photograph of a Western blot of an SDS-PAGE gel of protein fractions as described to FIG. 13A. The Western blot was stained with a polyclonal flagellin-specific antibody. The positions of various molecular weight (in kDa) markers are indicated on the left of the photograph. The arrow on the left of the photograph indicates the position of an over-expressed 34 kDa protein.

Figure 14:
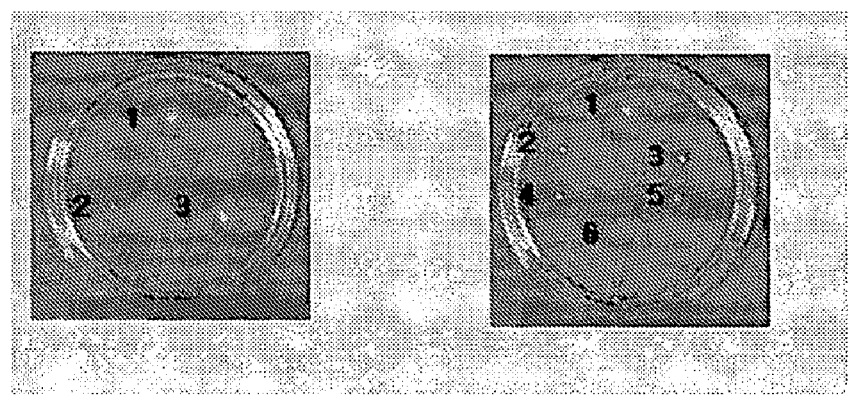

FIG. 14 is photographs of motility plates of various *B. halodurans* Alk36 strains. A: colony (1), *B. halodurans* Alk36 WT; colony (2) BhFC01 (hag); colony (3), BhFC01 (hag)+pSEC194FliC. B: colony (1), *B. halodurans* Alk36 WT; colonies 2-6 BhFC01 transformed with: (2) pSECNC1, (3) pSECNC2, (4) pSECNC3, (5) pSECNC5, (6) pSECNC6.

Figure 15A:
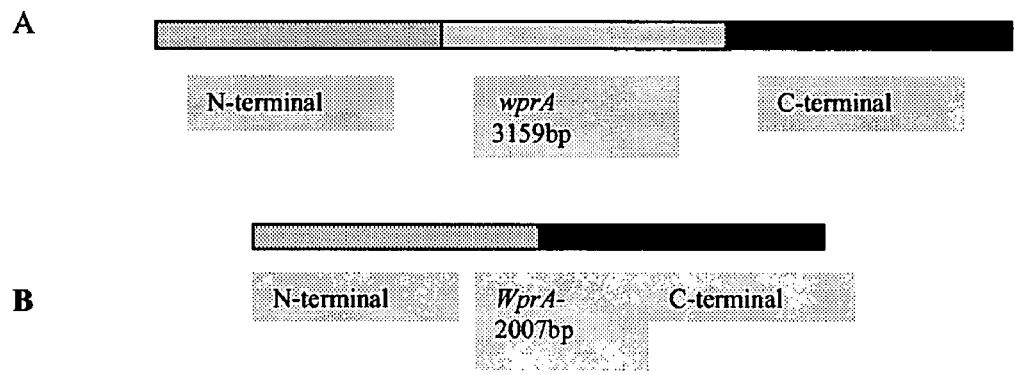

FIG. 15A is a schematic depiction of the complete wprA-coding region. The white region in A shows the area of the coding region which has been deleted in construction of pSECwprA- depicted in B. This construct was then used for the knockout of the wprA gene on the chromosome of *B. halodurans* BhFC01

Figure 15B:
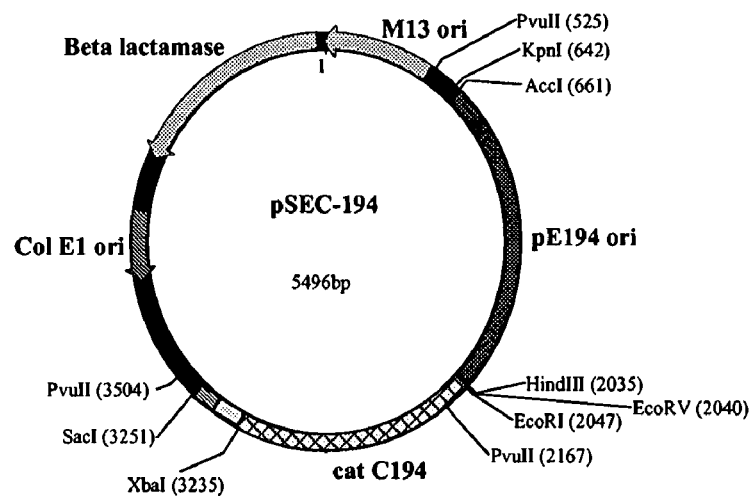

FIG. 15B is a depiction of the pSEC194wprA- plasmid map.

Figures 16, 17:
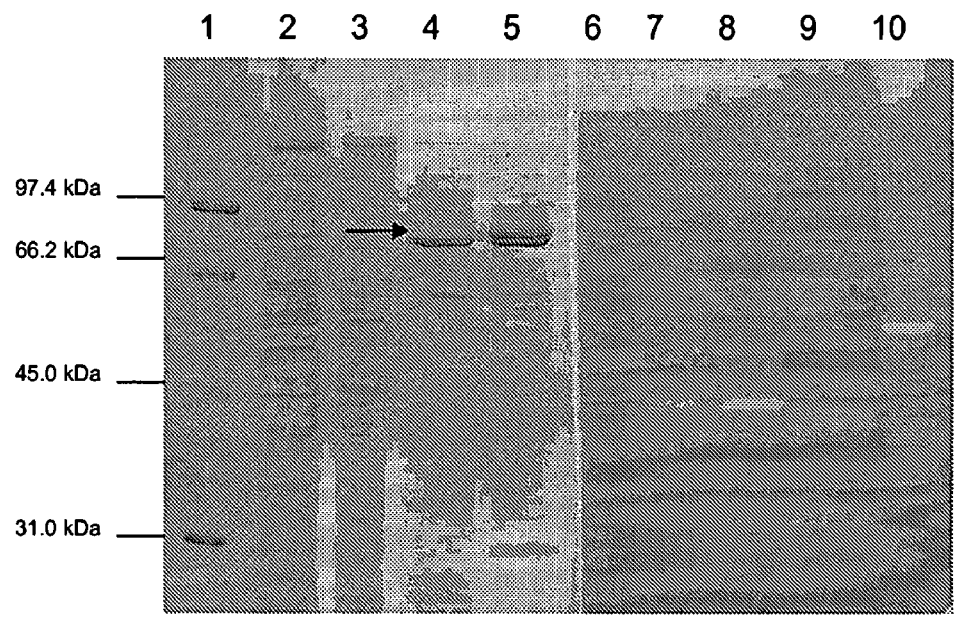

FIG. 16 is a photograph of Coomassie-blue-stained SDS-PAGE gels analyzing proteases in the extracellular (EX) and cell surface (CS) fractions of the strains BhFC01 and BhFC04. Aliquots of the EX and CS fractions were separated by SDS-PAGE gel electrophoresis and stained with Coomassie blue to visualize the protein bands (lanes 2-5) or for protease activity after renaturation treatment (lanes 7-10). Lanes 1 and 6, molecular weight markers; lanes 2 and 7, BhFC04 extracellular fraction; lanes 3 and 8, BhFC01 extracellular fraction; lanes 4 and 9, BhFC04 cell surface fraction; lanes 5 and 10, BhFC01 cell surface fraction. The positions of various molecular weight (in kDa) markers are indicated on the left of the photograph. The arrow indicates the deleted WprA protein band in the cell wall fraction of BhFC04 (lane 4). Successful elimination of protease activity in the same fraction is shown in lane 9.

FIG. 17 is a depiction of the amino acid sequence of the poly-His peptide and the nucleotide sequence encoding it. The nucleotide sequence includes the part of the MCS remaining in the pSEC194NHisC6 construct to give the full size of the incorporated peptide. The total size of the inserted peptide was 13 amino acids.

Figure 18:
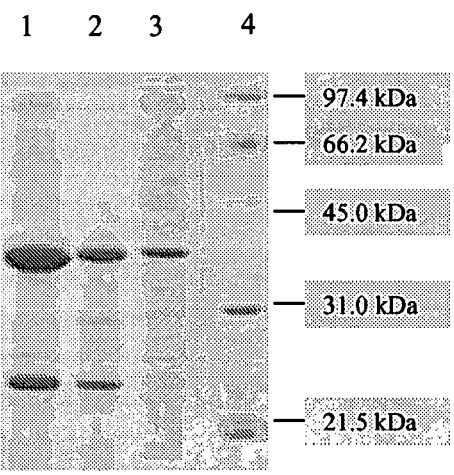

FIG. 18 is a photograph of a Coomassie blue-stained SDS-PAGE gel of CS fractions of the following strains: Lane 1, *B. halodurans* Alk36 WT; lane 2, BhFC04 containing pSEC194NC6; lane 3, BhFC04 containing pSEC194NHisC6; and lane 4, molecular weight markers. The positions of various molecular weight markers (in kDa) are indicated on the right of the photograph.

Figure 19:
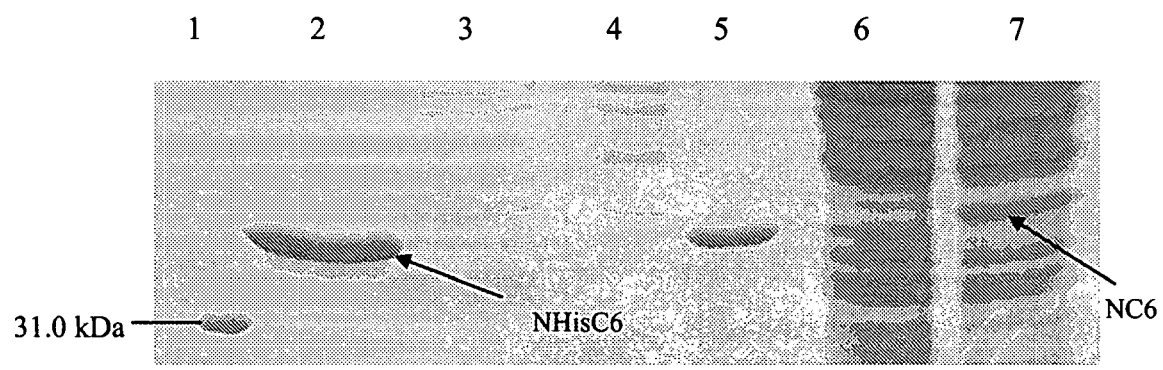

FIG. 19 is a photograph of a Coomassie blue-stained SDS-PAGE gel showing metal binding of the displayed poly-His tag on the CS fraction of strain BhFC04 containing pSEC194NhisC6. Lane 1, molecular weight markers; lane 2, pSEC194NHisC6 (eluted); lane 3, pSEC194NC6 (eluted); lane 4, pSEC194NC6 (beads); lane 5, pSEC194NHisC6 (beads); lane 6, pSEC194NHisC6 (flow through); lane 7, pSEC194NC6 (flow through). The position of a molecular weight marker (in kDa) is indicated on the left of the photograph. The arrows indicate the positions of the flagellin fusion proteins. Note the successful binding of the pSEC194NHisC6 fusion protein (lane 2) due to the presence of the poly-His tag.

FIG. 20 is a depiction of the amino acid sequence (SEQ ID NO:15) of the HIV gp120 peptide and the nucleotide sequence (SEQ ID NO:16) encoding it. The nucleotide sequence includes the part of the MCS remaining in the pSEC194NHivC6 construct.

FIG. 21 is photograph of a Coomassie blue-stained 10% SDS-PAGE gel of CS fractions of various strains and showing the flagellin fusion protein carrying the HIV gp120 antigenic peptide. Lane 1, BhFC04 containing pSEC194HivNC6; lane 2, WT (wild-type) *B. halodurans* Alk36; and lane 3, molecular weight markers. The positions of various molecular weight markers (in kDa) are indicated on the right of the photograph.

FIG. 22 is a photograph of a Western blot stained with a flagellin-specific polyclonal antibody. Lane 1, BhFC04+pSECNHivC6; lane 2, BhFC04+pSECNHisC6; lane 3, BhFC04+pSECNC6; lane 4, BhFC04; lane 5, *B haloduran* Alk36; lane 6, molecular weight marker. The position of a molecular weight (in kDa) marker is indicated on the right of the photograph. The arrow on the right of the photograph indicates the position of over-expressed flagellin (34 kDa) protein.

FIG. 23 is a depiction of the nucleotide sequence (SEQ ID NO:17) of the region of the lipA gene of *Geobacillus thermoleovorans* encoding mature lipase and the amino acid sequence (SEQ ID NO:18) of the mature lipase.

FIG. 24 is a photograph of a zymogram of lipase activity in the various protein fractions isolated from BhFC04 carrying the pSEC194NLipC3 construct. The EX (lane 1), CS (lane 2 & 3), CW (lane 4) and IC (lane 5) fractions are shown. Note that the EX fraction shows no lipase activity. Lane 6, molecular weight markers. The position of various molecular weight (in kDa) markers are indicated on the right of the photograph. The arrow on the left of the photograph indicates the positions of the flagellin (FliC):lipase (Lip) fusion protein having a molecular weight of approximately 76 kDa.

FIG. 25 is a bar graph showing extracellular and whole cell lipase activity (in terms of Units (U) per mg of protein) of BhFC04 cells containing pSEC194NC6 (lipase negative control) or pSEC194NLipC after 8, 24 and 48 hours of growth.

FIG. 26 is a depiction of the amino acid sequence of the *B. halodurans* wprA cell wall protease (SEQ ID NO:19).

DETAILED DESCRIPTION

Various aspects of the invention are described below.

Flagellin-Based Fusion Proteins (FBFP)

The invention features FBFP useful for a wide range or purposes. The FBFP contain all or part of a bacterial flagellin protein and a heterologous polypeptide sequence replacing, or within, the variable region of the flagellin protein. The FBFP has the ability to be transported to, and expressed on, the surface of a bacterial cell that makes it. As used herein, a protein that is "expressed on the surface of a bacterial cell" is a protein that is attached directly or indirectly to the bacterial cell wall (e.g., a protein that is a component of bacterial flagellum) or is lodged in the cell wall. In either case, all or part of the protein is exposed to the exterior of the bacterial cell and can interact with appropriate substances outside the bacterial cell, e.g., metal ions, enzyme substrates, or receptors on cells of the immune system (e.g., B lymphocytes, T lymphocytes (CD4+ and/or CD8+), natural killer (NK) cells, or antigen presenting cells (APC) such as macrophages, monocytes, interdigitating dendritic cells (referred to herein as dendritic cells), and B lymphocytes.

The flagellin portion of the FBFP can be any bacterial flagellin but is preferably a Gram positive bacterial flagellin. Gram positive bacterial genera of interest include, without limitation, *Clostridium, Staphylococcus, Lactococcus, Lactobacillus, Streptococcus* and *Streptomyces*. Of particular interest are bacteria of the genus *Bacillus*. Useful species include *Bacillus subtilis, Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus* or *Bacillus thuringiensis*; or a *Streptomyces* strain, e.g. *Streptomyces lividans* or a *Lactococcus* strain e.g. *Lactococcus lactis*

A particularly useful species is *B. halodurans* and the flagellin can be that with an amino acid sequence (SEQ ID NO:2) shown in FIG. 7 and a coding sequence (SEQ ID NO:1) shown in FIG. 7. The flagellin portion of the FBFP can include the whole flagellin molecule or part of the flagellin molecule. As described in Example 2, flagellin molecules from different bacteria have regions of relatively high homology which include N-terminal and C-terminal conserved regions and an internal variable region. By aligning the amino acid sequence of any bacterial flagellin of interest with one or more of those referred to in Example 2 or to SEQ ID NO:2, one skilled in the art can determine where in the flagellin of interest these three regions are located.

The FBFP can, for example, lack all or part of the variable region of the protein. In *B. halodurans* flagellin (SEQ ID NO:2), a polypeptide of 272 amino acids, the variable region is located from amino acid 54 to amino acid 202, corresponding to nucleotides 162 to 606 of its coding sequence (SEQ ID NO:1) and the conserved N and C terminal regions are on either side of the variable region (i.e., amino acids 1 to 53 and amino acids 203 to 272 of SEQ ID NO:2, respectively, corresponding to nucleotides 1 to 161 and 607 to 816 of SEQ ID NO:1. In making these modifications to the flagellin sequence, all that is required is that the FBFP have the ability, if made in a bacterial cell, to be transported to and expressed on the surface of the bacterial cell.

The heterologous polypeptide useful in the FBFP of the invention can be any polypeptide other than: (a) the particular flagellin from which the flagellin-derived part of the FBFP was obtained; or (b) a part of the particular flagellin. It can replace all or a part of the variable region of flagellin protein of interest or it can be inserted into an intact variable region. When replacing part of the variable region, up to 148 (e.g., up to: 145, 140, 135, 130, 125, 120, 115, 110, 105, 100, 95, 90, 85; 80; 75; 65; 60; 55; 50; 45; 40; 35; 30; 25; 20; 15; 12; 10; 9; 8; 7; 6; 5; 4; 3; or 2) of the variable region amino acids can be deleted. The heterologous polypeptide can be any length and is preferably from 5-450 (e.g., 5-450, 5-200, 5-150, 5-100, 5-50, 5-40, 5-30, 5-20, 5-15, 5-10, 10-450, 10-200, 10-150, 10-100, 10-50, 10-40, 10-30, 10-20, 10-15, 20-450, 20-200, 20-150, 20-100, 20-50, 20-40, or 20-30) amino acids in length.

In addition, at either the N-terminal, C-terminal, or both ends of the heterologous polypeptide there can be "linker" amino acids separating the heterologous polypeptide from the flagellin-derived sequence. These amino acids can be inserted either as cleavable sites (see below), as moieties that allow the heterologous polypeptide to assume an appropriate three-dimensional structure, and/or they reflect the inclusion of appropriate restriction sites in a genetic construct used to make the FBFP recombinantly (see below). Such linkers can be 1-20 (e.g., 1-15, 1-12, 1-10, 1-9, 1-8, 1-7, 1-6, 1-5, 1-4, 1-3, or 1-2) amino acids long.

Cleavable sites on either end of the heterologous polypeptide in the FBFP would allow the heterologous polypeptide, optionally including residues from the linkers, to be excised from the FBFP and used in its excised form. Where the FBFP is made chemically, any number of cleavable cross-linkers (e.g., bifunctional cleavable cross-linkers) are known in the art and could be included. Alternatively, where the FBFP is made recombinantly, other cleavable sites can be "engineered" into the FBFP. An example of a chemical cleavage method makes use of a single methionine residue insertion at either end of the heterologous polypeptide (either immediately N and C terminal or separated by one or more linker residues from the termini). The heterologous polypeptide can then be easily cleaved using cyanogen bromide. A second example is the use of a single cysteine residue at either end of the heterologous polypeptide (located as described for the methionine residues) and subsequent cleavage using NTCB (2-nitro-5-thiocyanobenzoate). Enzymatic cleavage makes use of enzymatically active endoproteases able to recognise a specific amino acid sequence. An example is the Endo Arg C cysteine protease which recognises the amino acid sequence Arg-X where X can be any amino acid. This method would thus require the addition of two amino acids on either side of the heterologous polypeptide. Another example is the Endo Lys C serine protease which recognizes the sequence Lys-X where X can be any amino acid. Again two amino acids would need to be added at either end of the heterologous polypeptide. Different combinations of different enzymatic and chemical cleavage methodologies can be used to ensure all undesired amino acids are removed.

The heterologous polypeptide, or where one or two linkers are used the heterologous polypeptide and the linker(s), can be inserted immediately after any amino acid between amino acids 54-202 of SEQ ID NO:2, immediately after any amino acid between amino acids 147-190 of SEQ ID NO:2, immediately after any amino acid between amino acids 150-184 of SEQ ID NO:2, or immediately after any amino acid between amino acids 153-180 of SEQ ID NO:2. For example, the heterologous polypeptide can be inserted immediately after amino acids 153 or 180 of SEQ ID NO:2. Where a flagellin of interest has an amino acid sequence different from SEQ ID NO:2 (the amino acid sequence of *B. halodurans*), one of skill in the art, by aligning the relevant amino acid sequence with SEQ ID NO:2, would be able to predict amino acids in that flagellin corresponding to those listed above for SEQ ID NO: 2 and thus appropriate positions into which to insert a heterologous polypeptide, or where one or two linkers are used the heterologous polypeptide and the linker(s), of interest. Moreover, if less than the whole flagellin coding sequence is included in the construct, positions corresponding to those recited above for SEQ ID NO:2 can readily be ascertained by one of ordinary skill in the art.

The invention also features FBFP with conservative substitutions in either the flagellin portion of the FBFP or in the heterologous polypeptide portion. Conservative substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine. Each portion contains no more than 30 (e.g., no more than: 25; 20; 15; 10; 9; 8; 7; 6; 5; 4; 3; 2; or 1) conservative substitution(s).

As indicated above, in making any of the above modifications of sequence, all that is required that the FBFP have the ability, if made in a bacterial cell, to be transported to and expressed at the surface of the bacterial cell.

Heterologous polypeptides of interest include those useful in, without limitation, bioremediation, biomining, enzyme-mediated substrate conversions, as immunogens for activating immune responses in any of a variety of mammals, for use in preparing immunogen preparations, as a substance or composition for use in methods of treatment or prevention and therapeutic applications.

Bioremediation is a process whereby toxic substances (e.g., heavy metal ions or atoms) are removed from liquids (e.g., a potable water) by binding of the toxic substances to a solid substrate over which the liquid is passed so that the liquid is safe for animal (e.g., human) consumption. Biomining involves binding to a solid substrate of useful and/or precious metal ions or atoms in a liquid and the subsequent recovery of the metal atoms or ions from the solid substrate. For either purpose, certain metal-binding polypeptides can be used. These methods are described in greater detail below. Relevant polypeptides, which can be incorporated as heterologous polypeptides into the FBFP of the invention, include those known to bind to a variety of heavy, useful, precious, and/or toxic metal ions. Relevant metals include, without limitation, nickel (Ni), cadmium (Cd), gold (Au), platinum (Pt), palladium (Pd), titanium (Ti), copper (Cu), and silver (Ag). Thus, for example, poly-histidine (poly-His; e.g., hexahistidine) polypeptides have been shown to bind Cd, Ni, and Cu. In addition, Ag has been shown to bind to a polypeptide with the amino acid sequence: NPSSLFTYLPSD (SEQ ID NO:20). Pd has been shown to bind to polypeptides with the amino sequences: CSVTQNKYC (SEQ ID NO:21); CSPHPGPYC (SEQ ID NO:22); and CHAPTPMLC (SEQ ID NO:23). Pt has been shown to bind polypeptides with the amino acid sequences: CDRTSTWRC (SEQ ID NO:24); CQSVTSTKC (SEQ ID NO:25); and CSSSHLNKC (SEQ ID NO:26). Ti has been shown to bind to a polypeptide with the amino acid sequence: RKLPDAPGMHTW (SEQ ID NO:27) (Kriplani and Kay (2005), Curr Opinion Biotechnol, 16:470-475). Thus, all these polypeptides can be used as heterologous polypeptides in the FBFP of the invention.

A wide range of enzymes (or functional fragments of such enzymes) useful for high-volume conversion of certain substrates (in, for example, fermenters) to desired products can also be inserted as heterologous polypeptides into the FBFP of the invention. Relevant enzymes include, without limitation, hydrolytic enzymes such as amylases, proteases, esterases, and cellulases. Of particular interest are lipase enzymes such as described in Example 8. A "functional fragment" of an enzyme is a fragment of the enzyme that is shorter than the full-length mature enzyme and has at least 20% (e.g., at least: 30%; 40%; 50%; 60%; 70%; 80%; 90%; 95%; 98%; 99%; 100%; or more) of the ability of the full-length, wild-type enzyme to convert its substrate to its relevant product.

Immunogenic polypeptides useful for inducing immune responses in mammals (see below) can also be used as heterologous polypeptides. Such polypeptides can be full-length mature polypeptides or peptide fragments of such polypeptides. Immunogenic polypeptides can be derived from, for example, any of a wide variety of infectious (e.g., bacterial, fungal (including yeast), viral, or parasite (such as protozoan parasite)) microorganisms or cancer cells. Examples of relevant microorganisms include, without limitation, *Mycobacteria tuberculosis, Salmonella enteriditis, Listeria monocytogenes, M. leprae, Staphylococcus aureus, Escherichia coli, Streptococcus pneumoniae, Borrelia burgdorferi, Actinobacillus pleuropneumoniae, Helicobacter pylon, Neisseria meningitidis, Yersinia enterocolitica, Bordetella pertussis, Porphyromonas gingivalis*, mycoplasma, *Histoplasma capsulatum, Cryptococcus neoformans, Chlamydia trachomatis, Candida albicans, Plasmodium falciparum, Entamoeba histolytica, Toxoplasma brucei, Toxoplasma gondii, Leishmania major*, human immunodeficiency virus 1 and 2, influenza virus, measles virus, rabies virus, hepatitis virus A, B, and C, rotaviruses, papilloma virus, respiratory syncytial virus, feline immunodeficiency virus, feline leukemia virus, and simian immunodeficiency virus. Examples of relevant microbial proteins include, without limitation, the B subunit of heat labile enterotoxin of *E. coli* [Konieczny et al. (2000) FEMS Immunol. Med. Microbiol. 27(4):321-332], heat-shock proteins, e.g., the *Y. enterocolitica* heat shock protein 60 [Konieczny et al. (2000) supra; Mertz et al. (2000) J. Immunol. 164(3):1529-1537] and *M. tuberculosis* heat-shock proteins hsp60 and hsp70, the *Chlamydia trachomatis* outer membrane protein [Ortiz et al. (2000) Infect. Immun. 68(3):1719-1723], the *B. burgdorferi* outer surface protein [Chen et al. (1999) Arthritis Rheum. 42(9):1813-1823], the *L. major* GP63 [White et al. (1999) Vaccine 17(17):2150-2161 (and published erratum in Vaccine 17(20-21):2755)], the *N. meningitidis* meningococcal serotype 15 PorB protein [Delvig et al. (1997) Clin. Immunol. Immunopathol. 85(2); 134-142], the *P. gingivalis* 381 fimbrial protein [Ogawa, (1994) J. Med. Microbiol. 41(5):349-358], the *E. coli* outer membrane protein F [Williams et al. (2000) Infect. Immun. 68(5):2535-2545], influenza virus hemagglutinins and neuramindases, retroviral (e.g., HIV) surface glycoproteins (e.g., HIV gp160/120/41), or retroviral tat or gag proteins.

Furthermore, tumor-associated antigens (TAA) or peptide fragments of TAA can be used as heterologous polypeptides. As used herein, a "TAA" is a molecule (e.g., a protein molecule) that is expressed by a tumor cell and either (a) differs qualitatively from its counterpart expressed in normal cells, or (b) is expressed at a higher level in tumor cells than in normal cells. Thus, a tumor antigen can differ (e.g., by one or more amino acid residues where the molecule is a protein) from, or it can be identical to, its counterpart expressed in normal cells. It is preferably not expressed by normal cells. Alternatively, it is expressed at a level at least two-fold higher (e.g., a two-fold, three-fold, five-fold, ten-fold, 20-fold, 40-fold, 100-fold, 500-fold, 1,000-fold, 5,000-fold, or 15,000-fold higher) in a tumor cell than in the tumor cell's normal counterpart. Examples of relevant cancers include, without limitation, hematological cancers such as leukemias and lymphomas, neurological tumors such as astrocytomas or glioblastomas, melanoma, breast cancer, lung cancer, head and neck cancer, gastrointestinal tumors such as gastric or colon cancer, liver cancer, pancreatic cancer, genitourinary tumors such ovarian cancer, vaginal cancer, bladder cancer, testicular cancer, prostate cancer or penile cancer, bone tumors, and vascular tumors. Relevant TAA include, without limitation, carcinoembryonic antigen (CEA), prostate specific antigen (PSA), MAGE (melanoma antigen) 1-4, 6 and 12, MUC (mucin) (e.g., MUC-1, MUC-2, etc.), tyrosinase, MART (melanoma antigen), Pmel 17(gp100), GnT-V intron V sequence (N-acetylglucoaminyltransferase V intron V sequence), Prostate Ca psm, PRAME (melanoma antigen), β-catenin, MUM-1-B (melanoma ubiquitous mutated gene product), GAGE (melanoma antigen) 1, BAGE (melanoma antigen) 2-10, c-ERB2 (Her2/neu), EBNA (Epstein-Barr Virus nuclear antigen) 1-6, gp75, human papilloma virus (HPV) E6 and E7, p53, lung resistance protein (LRP), Bc1-2, and Ki-67.

Therapeutic polypeptides that can be incorporated as heterologous polypeptides into the FBFP of the invention include, without limitation, human growth hormone (HGH), anti-retroviral agents (e.g., FUZEON, NEUPOGEN), anti-microbial peptides (e.g., indolicidin, buforin, nisin and trichogin), polypeptides useful for treating cardiovascular disease (e.g., nesiritide), and polypeptides useful for treating diabetes (e.g., liraglutide and insulinotropin). Generally, but not necessarily, these heterologous polypeptides would be excised from the FBFP, and in certain circumstances formulated into a preparation, prior to administration to appropriate mammalian subjects (e.g., a human subjects or patients).

The FBFP of the invention can be synthesized by standard chemical means known to those in the art. In addition, the FBFP can be produced by standard in vitro recombinant DNA techniques and in vivo transgenesis, using nucleotide sequences encoding the appropriate FBFP (e.g., those techniques described in the Examples below). Methods well-known to those skilled in the art can be used to construct expression vectors containing relevant coding sequences and appropriate transcriptional/translational control signals. See, for example, the techniques described in Sambrook et al., *Molecular Cloning: A Laboratory Manual* (2nd Ed.) [Cold Spring Harbor Laboratory, N.Y., 1989], and Ausubel et al., *Current Protocols in Molecular Biology* [Green Publishing Associates and Wiley Interscience, N.Y., 1989].

FBFP of the invention also include those described above, but modified by the addition, at the amino- and/or carboxyl-terminal ends, of a blocking agent to facilitate survival of the relevant FBFP. This can be useful in those situations in which the peptide termini tend to be degraded by proteases (e.g. in a mammalian subject). Such blocking agents can include, without limitation, additional related or unrelated peptide sequences that can be attached to the amino and/or carboxyl terminal residues of the peptide to be administered. This can be done either chemically during the synthesis of the peptide or by recombinant DNA technology by methods familiar to artisans of average skill.

Alternatively, blocking agents such as pyroglutamic acid or other molecules known in the art can be attached to the amino and/or carboxyl terminal residues, or the amino group at the amino terminus or carboxyl group at the carboxyl terminus can be replaced with a different moiety. Likewise, the peptides can be covalently or non-covalently coupled to pharmaceutically acceptable "carrier" proteins prior to administration.

Also of interest are peptidomimetic compounds that are designed based upon the amino acid sequences of the FBFP. Peptidomimetic compounds are synthetic compounds having a three-dimensional conformation (i.e., a "peptide motif") that is substantially the same as the three-dimensional conformation of a selected polypeptide. The polypeptide motif provides the peptidomimetic compound with the ability to function as required. Peptidomimetic compounds can have additional characteristics that enhance their therapeutic utility, such as increased cell permeability and prolonged biological half-life.

The peptidomimetics typically have a backbone that is partially or completely non-peptide, but with side groups that are identical to the side groups of the amino acid residues that occur in the peptide on which the peptidomimetic is based. Several types of chemical bonds, e.g., ester, thioester, thioamide, retroamide, reduced carbonyl, dimethylene and ketomethylene bonds, are known in the art to be generally useful substitutes for peptide bonds in the construction of protease-resistant peptidomimetics.

Nucleic Acid Molecules

The invention also features nucleic molecules encoding the above-described FBFP of the invention. In these nucleic acid molecules, the sequences encoding the flagellin-derived portions of the FBFP, the sequences encoding the heterologous polypeptide portion, and those encoding optional linkers are assembled such that all the portions are in the appropriate reading frame such that, in the FBFP encoded by the nucleic acid molecule, each portion has an amino acid sequence corresponding to the section of the protein from which it was derived or such sequence but with any modifications deliberately included. One of skill in the art will know how to construct appropriate "in frame" nucleic acid molecules.

The nucleic acid molecules of the invention also include genetic (DNA) constructs useful for making FBFP with any heterologous polypeptide of interest. The genetic construct contains all or part of the coding sequences of any of the flagellin described above and, inserted into the region of the coding sequence encoding the flagellin variable region (also referred to herein as the variable region of the flagellin coding sequence), a linker nucleic acid sequence. Particularly useful as linker nucleic acid linker sequences are multiple cloning sites (MCS) containing at least one (e.g., 2, 3, 4, 5, 6, 7, 8, 9, 10, 11, 12, 15, 17, 20, or even 30) consecutive and/or overlapping restriction enzyme recognition/cutting sites. Restriction enzymes and their recognition/cutting sequences are known in the art and include those described in the Examples below. Such MCS are used for inserting heterologous polypeptide-encoding nucleotide sequences. It is understood that an MCS can be inserted such that a nucleotide sequence "downstream" of it is read in the appropriate frame or not. All that is required is that, after the insertion of the heterologous polypeptide-encoding sequence, the entire FBFP coding sequence is in the correct reading frame.

Where the flagellin (or part of the flagellin) is *B. halodurans* flagellin, the linker nucleic acid sequences (including MCS) can be inserted immediately after any nucleotide between nucleotide 162 and nucleotide 606 of SEQ ID NO:1, e.g., immediately after any nucleotide between nucleotide 441 and nucleotide 570 of SEQ ID NO:1, immediately after any nucleotide between nucleotide 450 and nucleotide 552 of SEQ ID NO:1, or immediately after any nucleotide between nucleotide 459 and nucleotide 540 of SEQ ID NO:1. The linker nucleic acid sequences (including MCS) can be inserted, for example, immediately after nucleotide 459 or nucleotide 540 of SEQ ID NO:1. Where a flagellin of interest has an amino acid sequence different from SEQ ID NO:2 (the amino acid sequence of *B. halodurans*), one of skill in the art, by aligning the relevant amino acid sequence with SEQ ID NO:2, would be able to predict nucleotides in the coding sequence of that flagellin corresponding to those listed above for SEQ ID NO: 1 and thus appropriate positions into which to insert linker nucleic acid sequences of interest. Moreover, if less than the whole flagellin coding sequence is included in the construct, positions corresponding to those recited above for SEQ ID NO:1 can readily be ascertained by one of ordinary skill in the art.

The invention also provides kits containing one or more (e.g., 2, 3, 4, 5, 6, 7, 8, 9, 10, or more) of the genetic (DNA) constructs of the invention. The constructs are generally supplied as components incorporated into expression vectors. The kits can further contain one or more restriction enzymes useful for digesting the constructs in order to insert a heterologous polypeptide-encoding nucleotide sequence into the construct. The kit can also contain ancillary reagents such as buffers, salt solutions, and/or any other reagents for relevant restriction enzyme digest reactions. Moreover, the kit can contain a ligase enzyme (and the above-listed ancillary agents) for ligating a heterologous polypeptide-encoding nucleotide sequence into the construct. In addition, the kit can contain host (any of those recited herein) useful for expressing the genetic constructs. The kit can also include written instructions (on, for example, packaging material or a package insert) on how to digest the constructs with one or two appropriate restriction enzymes, how to ligate a heterologous polypeptide-encoding nucleotide sequence into the construct, and/or how to transform host cells with the genetic constructs after such ligation.

The FBFP-encoding nucleic acid molecules of the invention can be cDNA, genomic DNA, synthetic DNA, or RNA, and can be double-stranded or single-stranded (i.e., either a sense or an antisense strand). Segments of these molecules are also considered within the scope of the invention, and can be produced by, for example, the polymerase chain reaction (PCR) or generated by treatment with one or more restriction endonucleases. A ribonucleic acid (RNA) molecule can be produced by in vitro transcription. Preferably, the nucleic acid molecules encode polypeptides that, regardless of length, are soluble under normal physiological conditions.

The nucleic acid molecules of the invention can contain naturally occurring sequences, or sequences that differ from those that occur naturally, but, due to the degeneracy of the genetic code, encode the same polypeptide. In addition, these nucleic acid molecules are not limited to coding sequences, e.g., they can include some or all of the non-coding sequences that lie upstream or downstream from a coding sequence.

The nucleic acid molecules of the invention can be synthesized (for example, by phosphoramidite-based synthesis) or obtained from a biological cell, such as the cell of a a prokaryote (e.g., a bacterium such as a *Bacillus* bacterium or *Escherichia coli*). Combinations or modifications of the nucleotides within these types of nucleic acids are also encompassed.

The isolated nucleic acid molecules of the invention encompass segments that are not found as such in the natural state. Thus, the invention encompasses recombinant nucleic acid molecules incorporated into a vector (for example, a plasmid or viral vector) or into the genome of a heterologous cell (or the genome of a homologous cell, at a position other than the natural chromosomal location). Recombinant nucleic acid molecules and uses therefore are discussed further below.

The invention also encompasses: (a) vectors (see below) that contain any of the foregoing sequences (including coding sequence segments) and/or their complements (that is, "antisense" sequences); (b) expression vectors that contain any of the foregoing sequences (including coding sequence segments) operably linked to one or more transcriptional and/or translational regulatory elements (TRE; examples of which are given below) necessary to direct expression of the coding sequences; (c) expression vectors encoding, in addition to a FBFP, a sequence unrelated to the FBFP, such as a reporter, a marker, or a signal peptide fused to FBFP; and (d) genetically engineered host cells (see below) that contain any of the foregoing expression vectors and thereby express the nucleic acid molecules of the invention.

The TRE referred to above and further described below include but are not limited to inducible and non-inducible promoters, enhancers, operators and other elements that are known to those skilled in the art and that drive or otherwise regulate gene expression in prokaryotes. Such regulatory elements include but are not limited to a promoter fragment cloned from the *Bacillus* temperature phage SPO2 (Schoner et al., (1983) Gene 22: 47-57), sucrose inducible sacB promoter (Lee et al., (2000), Appl Environ Microbiol 66: 476-480), vegI promoter from *B. subtilis* (Lam et al., (1998), J Biotechnol 63: 167-177), aprE promoter (Olmos Soto and Contreras-Flores, (2003) Appl Microbiol Biotechnol 62: 369-373), AmyQ promoter from *Bacillus amyloliquefaciens* (Widner et al., (2000), J Industrial Microbiol Biotechnol 25:204-212) and the temperature-sensitive C1 regulated promoter system (Scofield et al., (2003), Appl. Environ. Microbiol. 69:3385-3392. Of particular interest is the $\sigma^D$ promoter that is the natural promoter of the *B. halodurans* flagellin (hag) gene [Sakamoto et al. (1992) J. Gen. Microbiol. 138: 2159-2166].

Host bacterial cells can be of the same species or genus as the species or genus from which the flagellin-derived sequence of the FBFP expressed, or to be expressed, by the host cell was obtained, or not. The host cells and the flagellin-derived sequence will preferably be of the same genus, more preferably of the same species.

Moreover the invention provides a substantially pure culture of a microorganism (e.g., a microbial cell such as a bacterial cell). As used herein, a "substantially pure culture" of a microorganism is a culture of that microorganism in which less than about 40% (i.e., less than about: 35%; 30%; 25%; 20%; 15%; 10%; 5%; 2%; 1%; 0.5%; 0.25%; 0.1%; 0.01%; 0.001%; 0.0001%; or even less) of the total number of viable microbial (e.g., bacterial cells) in the culture are viable microbial cells other than the microorganism. The term "about" in this context means that the relevant percentage can be 15% percent of the specified percentage above or below the specified percentage. Thus, for example, about 20% can be 17% to 23%. Such a culture of microorganisms includes the microorganisms and a growth, storage, or transport medium. Media can be liquid, semi-solid (e.g., gelatinous media), or frozen. The culture includes the cells growing in the liquid or in/on the semi-solid medium or being stored or transported in a storage or transport medium, including a frozen storage or transport medium. The cultures are in a culture vessel or storage vessel or substrate (e.g., a culture dish, flask, or tube or a storage vial or tube).

The microbial cells of the invention can be stored, for example, as frozen cell suspensions, e.g., in buffer containing a cryoprotectant such as glycerol or sucrose, as lyophilized cells. Alternatively, they can be stored, for example, as dried cell preparations obtained, e.g., by fluidised bed drying or spray drying, or any other suitable drying method. Similarly the enzyme preparations can be frozen, lyophilised, or immobilized and stored under appropriate conditions to retain activity.

The invention also provides methods of making a FBFP of the invention. In such methods, a cell (any of those described herein) expressing an expression vector with which the cell is transformed, and in which the nucleotide sequence encoding is operably linked to one or more transcriptional and/or a translational regulatory elements, is cultured. The FBFP is then obtained (e.g., recovered from the culture). Obtaining or recovery from the culture can involve isolation of the FBFP from the cells or from the culture medium. The FBFP of the invention are actively secreted through flagellin channels from cells recombinantly expressing them and remain attached to the cell surface in chains up to 20 000 monomers where they may actively be separated from the cell surface into the culture medium, e.g. by mechanical shearing Gene-Disrupted Cells In a substantial number of certain substantially pure cultures of cells of the invention, and in certain isolated cells, the endogenous flagellin gene has been disrupted such that it either encodes no flagellin protein or it encodes a non-functional flagellin. As used herein, a "substantial number of cells in a culture" is at least 60% (e.g., at least: 70%; 80%; 85%; 90%; 95%; 98%; 99%; 99.5%; 99.8%; or even 100%) of the cells in the culture. As used herein, a "non-functional flagellin" is a flagellin that cannot be transported to the surface of the cell making it and/or cannot be expressed on the surface of a cell making it. An example of a non-functional flagellin polypeptide is a *B. halodurans* flagellin lacking amino acids 14 to 226 (see Example 4). Such cells are useful as host cells for producing and expressing on their surfaces an FBFP of the invention after transformation with an expression vector encoding the FBFP. Methods of disrupting endogenous genes are known in the art and generally involve homologous recombination. A particularly useful method is the forced integration method described in Example 4 or a variant of it.

In addition to lacking a functional flagellin gene, a substantial number (see above) of the cells of the above-described cultures, and the isolated cells, can have one or more genes encoding cell wall proteases disrupted by the methods referred to above. Disruption of a cell wall protease gene results in the production of none of the relevant cell wall protease or in the production of non-functional cell wall protease. As used herein, a "non-functional cell wall protease" is one having less than 20% (e.g., less than: 10%; 5%; 2%; 1%; 0.5%; 0.2%; 0.1%; 0.01%; or none) of the proteolytic activity of the relevant wild-type cell wall protease. By disrupting one or more cell wall protease genes, the level of expression on the surface of the relevant disrupted cell of an FBFP encoded by an expression vector with which the cell is transformed can be increased. One such gene is the wrpA gene (see Example 7). Other protease genes include apr, alp, vpr, apr X among others. The cells can be bacterial cells of any of the genera, species, and strains recited herein. An example of bacterial cells lacking a functional flagellin gene and lacking the coding sequence of the cell wall protease gene is the BhFC04 strain of *B. halodurans* (see Example 7).

Methods of Using FBFP

As pointed out above, the FBFP can be useful in, without limitation, bioremediation, biomining, enzyme-mediated substrate conversions, and as immunogens for activating immune responses in any of a variety of mammals. Thus, the invention features methods of performing bioremediation, biomining, enzyme-mediated substrate conversions, use in preparing immunogen preparations, as a substance or composition for use in a method of treatment or prevention and activating immune responses in mammalian subjects.

Bioremediation and Biomining

As indicated above, both bioremediation and biomining involve exposing a fluid e.g. water or industrial toxic waste streams or run-off from mines such as gold and platinum mines to a solid substrate that has been adapted to bind to appropriate metal ions or atoms in the fluid. In the case of bioremediation, the solid substrate with metal atoms or ions bound to it is either discarded or processed for reuse by eluting off and discarding the metal atoms or ions. In the case of the biomining, the metal atoms or ions are separated from the solid substrate and further processed as appropriate.

In the bioremediation and biomining processes of the invention, the fluid can be exposed to bacteria (any of those listed herein) expressing on their surfaces FBFP containing a metal-binding heterologous polypeptide. The bacteria can be live or dead (e.g., heat killed) and can be contained, for example, an appropriate filtering apparatus. Alternatively, the FBFP can be isolated from the appropriate recombinant bacteria and bound (e.g., covalently) to a solid substrate (e.g., metal, plastic, cellulose, agarose, or synthetic polymer such as nylon). The solid substrate can be in the form of, for example, a sheet, beads, particles, fibers, or threads. As yet another alternative, the heterologous polypeptide can be cleaved out of the FBFP, isolated, and bound to one of the above-listed solid substrates. The fluid is passed over or through, for example, a column or bed of the bacteria or substrate with FBFP (or heterologous polypeptide) bound to it, with the flow rate adjusted so that optimal binding of the metal atoms or ions to the FBFP occurs. The fluid can be contacted with the FBFP (or heterologous polypeptide) once or a plurality of times as required for optimal binding of the metal atoms or ions to the FBFP.

In bioremediation, the fluid is then used for whatever purpose it is intended, e.g., as drinking water or for an industrial process of interest. The FBFP source will generally be discarded or it can be regenerated by removal of the metal atoms or ions and reused.

In the case of biomining, the metal atoms or ions are recovered from the FBFP source. This can be achieved by exposing bacteria expressing the FBFP or the isolated FBFP to hydrolysing conditions e.g., acidic or alkaline conditions or high concentrations of positively charged ions as EDTA such that the metals are dissociated from the peptides and can be re-isolated.

Enzyme-Mediated Substrate Conversions

In these processes of the invention a substrate of interest could be esters or constituent carboxylic acids and alcohols. The constituent molecules may be aliphatic, aromatic in combinations thereof, and may comprise other functional groups. The constituent molecules may be larger or small and may be found in foodstuffs (e.g. fatty acids, menthol) 'or in pharmaceutical compounds or intermediates (e.g. naproxen, ibuprofen). The lipases and esterases may be used in food and beverage processing, bioremediation or synthesis of fine chemicals and pharmaceuticals. In the latter the enzymes may be used for chemo- regio- or stero-selectivity. In particular the lipases and esterases are often applied to the stero-selective synthesis or hydrolysis of esters thereby allowing for resolution desired chiral compounds from racemic mixtures.

In this case, after a sufficient amount of product has been generated, the reaction can be stopped and the product extracted or isolated from the reaction mixture.

In this case, after the reaction, the composition or mixture is processed as desired including, for example, inactivating the enzyme and/or separating the mixture or composition from the FBFP source.

The reactions can be carried out in, for example, high volume fermenters. The FBFP (or the heterologous polypeptide enzyme (or fucleaved from the FBFP) can be used in the same forms as described above for bioremediation and biomining. Thus, live or dead bacteria expressing on their surfaces the appropriate FBFP, isolated FBFP, or heterologous polypeptide enzyme cleaved from the FBFP can be added directly to the reaction mixture containing the enzyme substrate. Alternatively, the isolated FBFP or the heterologous polypeptide enzyme cleaved from the FBFP, can be bound to one of the above-described solid substrates (e.g., agarose beads). Optionally and preferably, the reaction mixture is agitated or stirred. This is done, for example, where recombinant bacteria expressing the FBFP on their surfaces or solid substrate-bound agents are used as a source of the FBFP, in order to keep the bacteria or solid substrates suspended. At a time predetermined to be useful for product generation and/or substrate depletion, the product and/or composition or mixture depleted of substrate is separated from the FBFP source and processed as desired. Alternatively, the reaction can be monitored and once a desired level of product and/or substrate depletion is observed, the product and/or composition or mixture depleted of substrate is separated from the FBFP source and processed as desired. Prior to separation of the product and/or composition or mixture from the FBDP source, the enzyme reaction can optionally be stopped (e.g., by heat).

Methods of Activating an Immune Response

The invention features methods of activating mammalian immune responses in which cells of the immune system are exposed to one or more FBFP of the invention in which the heterologous polypeptide is an immunogenic polypeptide (see above) or to immunogenic heterologous polypeptides cleaved from FBFP. In the case of FBFP, the cells of the immune system can be contacted with isolated FBFP or recombinant bacteria expressing the FBFP on their surfaces. Such bacteria can be alive, dead, or attenuated. Immune responses that can be activated by these agents can be, for example, antibody-producing (B lymphocyte) responses. The FBFP (either isolated or on the surfaces of bacteria) are also useful for introducing peptide epitopes into antigen presenting cells (APC) in order to generate MHC (major histocompatibility complex) class I- or class II-restricted T cell responses. Such responses are typically only generated by recognition of peptide epitopes produced by processing of polypeptides synthesized within an appropriate APC. In addition, the FBFP of the invention can also be useful for sensitizing target cells for lysis by cytotoxic T lymphocytes (CTL) with specificity for a peptide epitope (as heterologous polypeptide) that the FBFP contains.

The methods of the invention can be performed in vitro, in vivo, or ex vivo. In vitro application of the FBFP or cleaved immunogenic heterologous polypeptides can be useful, for example, in basic scientific studies of immune mechanisms or for production of activated T cells for use in either studies on T cell function or, for example, passive immunotherapy.

In the in vitro methods of the invention, T cells (CD4+ and/or CD8+) obtained from a mammalian subject are cultured with a FBFP (isolated or expressed on the surface of bacteria, preferably dead bacteria) and APC, preferably, but not necessarily, obtained from the same individual as the T cells. Where the APC are obtained from a different individual, the donor of the T cells and the donor of the APC will preferably express at least one major histocompatibility complex (MHC) molecule (e.g., a MHC class I molecule) in common. APC can be essentially any MHC molecule-expressing cell. Where it is desired to elicit a MHC class I restricted immune response, the APC will express MHC class I molecules (and optionally MHC class II molecules) and where it is desired to elicit an MHC class II restricted immune response, the APC will express MHC class II molecules (and optionally MHC class I molecules). The APC will optimally also express one or more co-stimulatory molecules, e.g., the B7 family of molecules. Thus APC can be, for example, dendritic cells (DC), macrophages, monocytes, B cells, or cell lines (clonal or non-clonal) derived from any of these cells. They can also be any cell type (e.g., fibroblasts) transfected or transduced with and expressing a polynucleotide encoding an appropriate MHC molecule. Such cultures can also be supplemented with one or more cytokines or growth factors such as, without limitation, IL-1, IL-2, IL-3, IL-4, IL-6, IL-7, IL-12, IL-13, IL-15, IFN-, tumor necrosis factor- (TNF-), granulocyte macrophage colony-stimulating factor (GM-CSF), or granulocyte-colony stimulating factor (G-CSF). The cultures can be "restimulated" as often as necessary with either the FBFP or cleaved immunogenic heterologous polypeptide. The cultures can also be monitored at various times to ascertain whether the desired level of immune reactivity (e.g., CTL activity) has been attained.

The FBFP (and immunogenic heterologous polypeptides cleaved from FBFP) are generally useful for generating immune responses, as prophylactic vaccines or immune response-stimulating therapeutics, as a substance or composition for us in methods of treatment or prevention, and for preparing immunogenic preparations for use in methods of treatment or prevention. Thus, they can be used, for example, as immunogenic preparations, vaccines or therapeutic agents against infectious diseases due to any of the pathogens listed herein. It is also possible to administer the immunogenic peptide as a fusion with the flagellin protein. This will enhance the immunogenic response of the target organism since the flagellin has the same effect as an adjuvant (An ingredient—as in a prescription or solution—that facilitates or modifies the action of the principal ingredient). Adjuvants have the ability to stimulate innate immunity and in turn activate the adaptive immune response. It has already been established that flagellin induces an inflammatory response through the activation of APC's (see above). An example is the successful creation and presentation of a flagellin enhanced green fluorescent protein (EGFP) fusion protein. The flagellin-EGFP fusion was capable of stimulating APC's and also specific anti EGFP T-cell responses. EGFP alone was unable to stimulate neither APC's nor specific T-cell responses (Cuadros et al., 2004, Inf. Immun. Vol 72, 2810-2816, McSorley et al., 2002, J. Immunol. Vol 169, 3914-3919). Other peptides inserted into the flagellin which induced an immune response include Cholera toxin subunit B, Hepatitus B epitopes, *Streptococcus pyogenes* M protein epitope, HIV epitopes (gp 41, gp120), influenza A hemagglutinin epitope and various cell surface antigens from *Plasmodium* sp., Rotavirus, *Corynebacterium diphtheriae* and Meningococcal outer membrane protein (Stocker and Newton, 1994, Intern. Rev. Immunol. Vol 2, 167-178).

In addition, the FBFP (and immunogenic heterologous polypeptides cleaved from FBFP) can be useful therapeutics for cancer (e.g., any of those recited above); in cases where a subject is at relatively high risk for a cancer (e.g., lung cancer in a tobacco smoker or melanoma in a subject with multiple nevi), appropriate fusion agents can be used as vaccines.

As used herein, "prophylaxis" means complete prevention of the symptoms of a disease, a delay in onset of the symptoms of a disease, or a lessening in the severity of subsequently developed disease symptoms. As used herein, "therapy" means a complete abolishment of the symptoms of a disease or a decrease in the severity of the symptoms of the disease.

It is understood that, while the immune responses generated by the FBFP (and immunogenic heterologous polypeptides cleaved from FBFP) are preferably prophylactic and/or therapeutic, it is not required that they be. For example, the FBFP (and immunogenic heterologous polypeptides cleaved from FBFP) can be used in basic scientific studies on immune responses that are neither prophylactic nor therapeutic, for generating antibodies useful, for example, in detecting or purifying any of a variety of antigens, e.g., microbial antigens or TAA such as those recited herein.

The methods of the invention can be applied to a wide range of species, e.g., humans, non-human primates (e.g., monkeys), horses, cattle, pigs, sheep, goats, dogs, cats, rabbits, guinea pigs, hamsters, rats, and mice.

In Vivo Approaches

In one in vivo approach, the FBFP itself, bacteria (e.g., commensal bacteria) expressing the FBFP on their surfaces, or immunogenic heterologous polypeptides cleaved from FBFP are administered to the subject. Generally, the fusion agents of the invention will be suspended in a pharmaceutically-acceptable carrier (e.g., physiological saline) and administered orally or transdermally or injected (or infused) intravenously, subcutaneously, intramuscularly, intraperitoneally, intrarectally, intravaginally, intranasally, intragastrically, intratracheally, or intrapulmonarily. They can be delivered directly to an appropriate lymphoid tissue (e.g. spleen, lymph node, or mucosal-associated lymphoid tissue (MALT)). The dosage required depends on the route of administration, the nature of the formulation, the nature of the patient's illness, the subject's size, weight, surface area, age, and sex, other drugs being administered, and the judgment of the attending physician. Suitable dosages of isolated FBFP or immunogenic heterologous polypeptides cleaved from FBFP are in the range of 0.001-10.0 mg/kg. Wide variations in the needed dosage are to be expected in view of the variety of FBFP (and immunogenic heterologous polypeptides cleaved from FBFP) available and the differing efficiencies of various routes of administration. For example, oral administration would be expected to require higher dosages than administration by i.v. injection. Variations in these dosage levels can be adjusted using standard empirical routines for optimization as is well understood in the art. Administrations can be single or multiple (e.g., 2- or 3-, 4-, 6-, 8-, 10-, 20-, 50-, 100-, 150-, or more fold). Encapsulation of the polypeptide in a suitable delivery vehicle (e.g., polymeric microparticles or implantable devices) may increase the efficiency of delivery, particularly for oral delivery.

Alternatively, a polynucleotide containing a nucleic acid sequence encoding a FBFP of interest can be delivered to an appropriate cell of the animal. Expression of the coding sequence will preferably be directed to lymphoid tissue of the subject by, for example, delivery of the polynucleotide to the lymphoid tissue. This can be achieved by, for example, the use of a polymeric, biodegradable microparticle or microcapsule delivery vehicle, sized to optimize phagocytosis by phagocytic cells such as macrophages. For example, PLGA (polylacto-co-glycolide) microparticles approximately 1-10 m in diameter can be used. The polynucleotide is encapsulated in these microparticles, which are taken up by macrophages and gradually biodegraded within the cell, thereby releasing the polynucleotide. Once released, the DNA is expressed within the cell. A second type of microparticle is intended not to be taken up directly by cells, but rather to serve primarily as a slow-release reservoir of nucleic acid that is taken up by cells only upon release from the micro-particle through biodegradation. These polymeric particles should therefore be large enough to preclude phagocytosis (i.e., larger than 5 m and preferably larger than 20 m).

Another way to achieve uptake of the nucleic acid is using liposomes, prepared by standard methods. The vectors can be incorporated alone into these delivery vehicles or co-incorporated with tissue-specific antibodies. Alternatively, one can prepare a molecular conjugate composed of a plasmid or other vector attached to poly-L-lysine by electrostatic or covalent forces. Poly-L-lysine binds to a ligand that can bind to a receptor on target cells [Cristiano et al. (1995), *J. Mol. Med.* 73, 479]. Alternatively, lymphoid tissue specific targeting can be achieved by the use of lymphoid tissue-specific transcriptional regulatory elements (TRE) such as a B lymphocyte, T lymphocyte, or dendritic cell specific TRE. Lymphoid tissue specific TRE are known [Thompson et al. (1992), *Mol. Cell. Biol.* 12, 1043-1053; Todd et al. (1993), *J. Exp. Med.* 177, 1663-1674; Penix et al. (1993), *J. Exp. Med.* 178, 1483-1496]. Delivery of "naked DNA" (i.e., without a delivery vehicle) to an intramuscular, intradermal, or subcutaneous site, is another means to achieve in vivo expression.

In the relevant polynucleotides (e.g., expression vectors) the nucleic acid sequence encoding the FBFP of interest with an initiator methionine and optionally a targeting sequence is operatively linked to a promoter or enhancer-promoter combination.

Polynucleotides can be administered in a pharmaceutically acceptable carrier. Pharmaceutically acceptable carriers are biologically compatible vehicles which are suitable for administration to a human or other mammalian subject, e.g., physiological saline. A therapeutically effective amount is an amount of the polynucleotide which is capable of producing a medically desirable result (e.g., a T cell response) in a treated animal. As is well known in the medical arts, the dosage for any one patient depends upon many factors, including the patient's size, body surface area, age, the particular compound to be administered, sex, time and route of administration, general health, and other drugs being administered concurrently. Dosages will vary, but a preferred dosage for administration of polynucleotide is from approximately $10^6$ to $10^{12}$ copies of the polynucleotide molecule. This dose can be repeatedly administered, as needed. Routes of administration can be any of those listed above.

Ex Vivo Approaches

In one ex vivo approach, lymphoid cells, including T cells (CD4+ and/or CD8+ T cells), are isolated from the subject and exposed to the FBFP in vitro (see above). The lymphoid cells can be exposed once or multiply (e.g., 2, 3, 4, 6, 8, or 10 times). The level of immune activity (e.g., CTL activity) in the lymphoid cells can be tested after one or more exposures. Once the desired activity and level of that activity is attained, the cells are reintroduced into the subject via any of the routes listed herein. The therapeutic or prophylactic efficacy of this ex vivo approach is dependent on the ability of the ex vivo activated lymphocytes to exert, directly or indirectly, a neutralizing or cytotoxic effect on, for example, infectious microorganisms, host cells infected with microorganisms, or tumor cells.

An alternative ex vivo strategy can involve transfecting or transducing cells obtained from the subject with a polynucleotide containing a FBFP-encoding nucleotide sequence. The transfected or transduced cells are then returned to the subject. While such cells would preferably be lymphoid cells, they could also be any of a wide range of types including, without limitation, fibroblasts, bone marrow cells, macrophages, monocytes, dendritic cells, epithelial cells, endothelial cells, keratinocytes, or muscle cells in which they act as a source of the fusion protein for as long as they survive in the subject. In subjects with cancer, the cells can be cancer cells, e.g., their own cancer cells or cells of the same cancer type but from another individual, preferably an individual having one or more (e.g., one, two, three, four, five, or six) MHC molecules in common with the subject. The use of lymphoid cells would be particularly advantageous in that such cells would be expected to home to lymphoid tissue (e.g., lymph nodes or spleen) and thus the FBFP would be produced in high concentration at the site where they exert their effect, i.e., activation of an immune response. By using this approach, as in the above-described in vivo approach using fusion agent-encoding polynucleotides, active in vivo immunization with the FBFP is achieved. The same genetic constructs and signal sequences described for the in vivo approach can be used for this ex vivo strategy.

The ex vivo methods include the steps of harvesting cells from a subject, culturing the cells, transducing them with an expression vector, and maintaining the cells under conditions suitable for expression of the FBFP. These methods are known in the art of molecular biology. The transduction step is accomplished by any standard means used for ex vivo gene therapy, including calcium phosphate, lipofection, electroporation, viral infection, and biolistic gene transfer. Alternatively, liposomes or polymeric microparticles can be used. Cells that have been successfully transduced are then selected, for example, for expression of the FBFP or of a drug resistance gene. If desired, the cells can be treated with an agent (e.g., x- or -irradiation or mitomycin C) that inhibits cell proliferation; generally where the cells are cancer cells (particularly cancer cells from the subject or from an individual that is MHC identical to the subject) will be so treated. The cells are then injected or implanted into the patient.

These methods of the invention can be applied to any of the diseases and species listed here. Methods to test whether a FBFP or immunogenic heterologous polypeptide cleaved from a FBFP is therapeutic for or prophylactic against a particular disease are known in the art. Where a therapeutic effect is being tested, a test population displaying symptoms of the disease (e.g., cancer patients) is treated with a test FBFP or an immunogenic heterologous polypeptide cleaved from a FBFP, using any of the above described strategies. A control population, also displaying symptoms of the disease, is treated, using the same methodology, with a placebo. Disappearance or a decrease of the disease symptoms in the test subjects would indicate that the FBFP or immunogenic heterologous polypeptide cleaved from a FBFP was an effective therapeutic agent.

By applying the same strategies to subjects prior to onset of disease symptoms, FBFP or immunogenic heterologous polypeptides cleaved from FBFP can be tested for efficacy as prophylactic agents, i.e., vaccines. In this situation, prevention of onset of disease symptoms is tested. Analogous strategies can be used to test for the efficacy of FBFP and immunogenic heterologous polypeptides cleaved from FBFP in the prophylaxis of a wide variety of infectious diseases, e.g., those involving any of the microorganisms listed above.

The following examples serve to illustrate, not limit, the invention.

EXAMPLES

Example 1

Isolation and Sequencing of B. halodurans Alk36 Flagellin

Aliquots of B. halodurans Alk36 bacteria deposited at the NCIMB Culture Collection (NCIMB Ltd, Ferguson Building, Craibstone Estate, Bucksburn, Aberdeen, AB21 9YA) under accession number NCIMB41348 were grown in Luria broth (Tryptone 10 g/l, Yeast extract 5 g/l, NaCl 10 g/l), pH8.5 at 42° C. for various times up to 72 hours. The cell-surface protein fractions of all samples were prepared by pelleting the cells (30 ml) by centrifugation at 7,000 rpm (revolutions per minute) in SS34 tubes for 10 min. Six ml of supernatant (extra cellular fraction) was mixed with 10% (w/v) trichloroacetic acid (TCA; 6 ml) and stirred for 1 hr. Proteins were pelleted by centrifugation at 7,000 rpm in glass Corex tubes for 20 min, resuspended in 100 µl sample buffer (1×) boiled for 2 min, and loaded onto a 10% SDS-PAGE (sodium dodecyl sulfate polyacrylamide gel electrophoresis) gel.

The cell pellets were resuspended in distilled $H_2O$ (3 ml) and 0.2 N NaOH (3 ml) and stirred for 30 min at room temperature. Cells were pelleted by centrifugation at 7,000 rpm for 10 min, and the supernatant (6 ml) was mixed with 10% (w/v) trichloroacetic acid (TCA; 6 ml) and stirred for 1 hr. Precipitated cell surface proteins were pelleted by centrifugation at 7,000 rpm in glass Corex tubes for 20 min, resuspended in 100 µl sample buffer (1×), boiled for 2 min, and loaded onto a 10% SDS-PAGE (sodium dodecyl sulfate polyacrylamide gel electrophoresis) gel (50 g of protein per well) and resolved using a standard procedure.

Figures 1, 2:
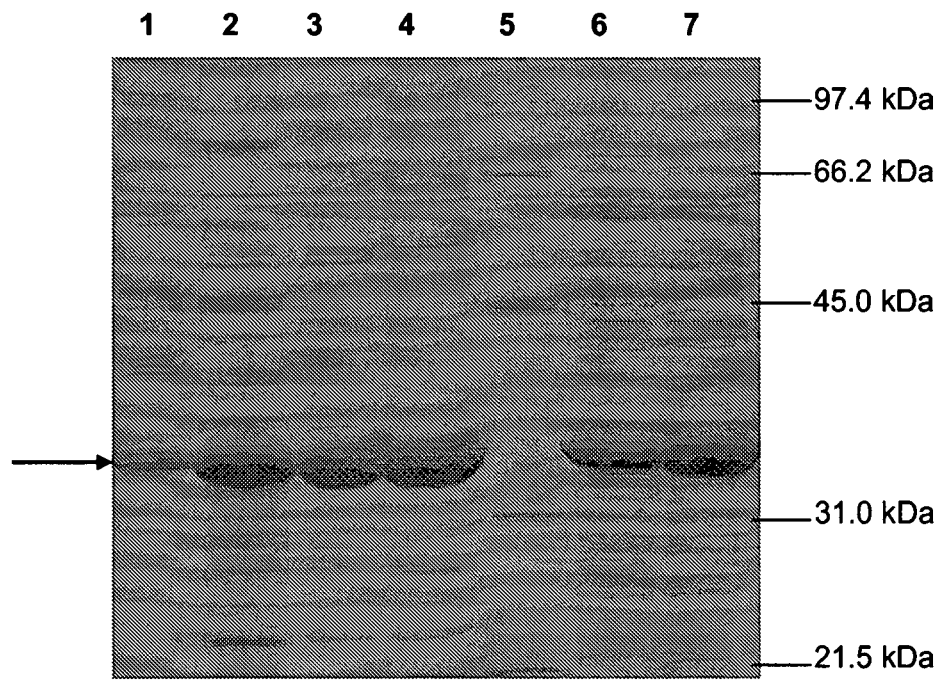
FIG. 1 is a photograph of a Coomassie blue-stained SDS-PAGE (sodium dodecyl sulfate polyacrylamide electrophoresis) gel showing protein profiles of extracellular (EX) and cell bound (CB) proteins produced by B. halodurans Alk 36 sampled during different stages of growth. Lane 1, CB (6 hours); lane 2, CB (24 h); lane 3, CB (48 h); lane 4, (72 h); lane 5, molecular weight markers; lane 6, EX (24 h); lane 7, EX (72 h). The positions of various molecular weight markers (in kDa) are indicated on the right of the photograph. The arrow on the left of the photograph indicates the position of an over-expressed 34 kDa protein.
FIG. 2 is a depiction of the first 22 N-terminal amino acids of the ~34 kDa B. halodurans Alk36 protein (SEQ ID NO:3) aligned with the corresponding first 22 amino acids of the flagellin protein from the alkalophilic Bacillus sp. C-125 (SEQ ID NO:4). Positions of identity are indicated by + signs as well as letters corresponding to the relevant amino acids.

A highly expressed protein resolved to a band corresponding to ~34 kDa. This protein was present and stable for at least 72 hours (FIG. 1). The resolved protein fraction was subsequently blotted onto an Immobilon-P membrane (Millipore Corporation, Billerica, Mass.), stained for 2 min with Coomassie blue [0.1% R250 in 50% (v/v) methanol], and destained for 5 min in destain solution (50% (v/v) methanol; 10% (v/v) ascetic acid). The ~34 kDa protein band from FIG. 1 lane 4 was cut out and the amino acid sequence of the blotted protein determined by N-terminal sequencing using a Perkin Elmer Applied Biosystems (Foster City, Calif., U.S.A) Procise® 491 Sequencer, according to manufacturer's instructions. The sequence of the first 22 amino acids was obtained (FIG. 2).

Example 2

Bioinformatic Analysis of B. halodurans Alk36 Flagellin

The 22 amino acid peptide sequence obtained from the N-terminus of B. halodurans Alk36 flagellin was used to screen the Swiss-Protein database for homologous proteins. This peptide sequence demonstrated significant homology to the N-terminus of the hag product flagellin protein from the alkalophilic Bacillus sp. C-125 [Sakamoto et al. (1992), J. Gen. Microbiol. 138: 2159-2166], now renamed B. halodurans C-125 [Takami et al. (1999), Biosci. Biotechnol. Biochem. 5:943-945] (FIG. 3). The first 12 amino acids of the N-terminus of B. halodurans Alk36 flagellin demonstrated 92% identity with the N-terminus of B. halodurans C-125 flagellin [Sakamoto et al., supra]. Since further comparison of the amino acid sequences of flagellin proteins from Escherichia coli, Salmonella typhimurium and Bacillus subtilis 168 [LaVallie et al. (1989) J. Bacteriol. 171:3085-3094] indicated that the N- and C-terminal regions of this family of flagellin proteins demonstrate significant conservation of sequence, the ~34 kDa B. halodurans Alk36 protein was concluded to be a flagellin protein and therefore a product of the hag gene.

Example 3

PCR Amplification and Cloning of the B. halodurans Alk36 Gene

Cloning of the hag Gene Open Reading Frame (ORF)

The ORF of the hag gene was amplified by a polymerase chain reaction (PCR) from chromosomal DNA using a forward primer (F-flag; 5' CTC CTG CAG MT CAC AAT TTA CCA GCA 3' Tm=58.1° C.) and a reverse primer (R-flag; 5'

Figure 4:
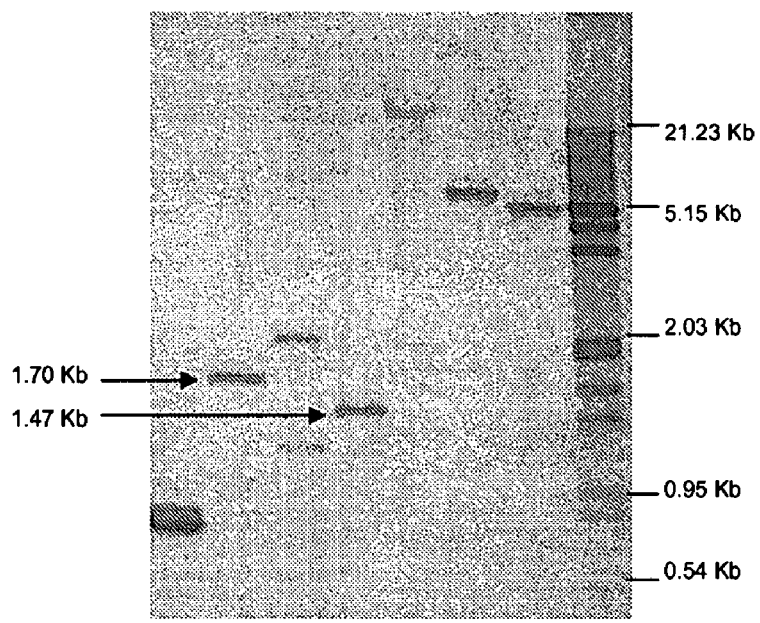
FIG. 4 is photograph of DIG-labeled Southern blot of B. halodurans Alk36 chromosomal DNA digested with various restriction enzymes. The blot was probed with the 800 bp B. halodurans Alk36 hag coding fragment labeled with DIG. Lane 1, 800 bp B. halodurans Alk36 hag gene fragment digested with XbaI/BamHI; Lanes 2-7, B. halodurans Alk36 chromosomal DNA digested with different restriction endonucleases: lane 2, AccI; lane 3, EcoRI; lane 4, HindIII; lane 5, PstI; lane 6, ClaI; lane 7, PvuI. Lane 8, molecular weight markers. The positions of size markers (in Kb) are indicated on the right of the photograph and the positions on the blot of fragments of 1.70 Kb and 1.47 Kb are indicated by arrows on the left of the photograph.

GGT TCG AAC ATC GCT TGA GAC GCT TC 3' Tm=61° C.) based on the conserved sequences of the N- and C-terminal regions of the hag gene of *B. halodurans* C-125 (Sakamoto et al., 1992). The PCR reaction included final concentrations of the template chromosomal DNA (100 µg/µl), F-flag (0.5 µm/10 µl), R-flag (0.5 µl/10 µl), dNTPs (deoxyribonucleotide triphosphates; 0.8 µl/10 µl) and 1 µl Pwo DNA polymerase (5 u/µl, Roche) in 1× PCR Buffer with MgCl$_2$ (2.0 mM) to a final volume of 100 µl. The PCR reaction was incubated according to standard procedures with appropriate optimization. The PCR product was resolved by standard agarose (1.0%) electrophoresis using low-melting point agarose and yielded a fragment resolving to a band corresponding to 800 bp (base pairs). The 800 bp band was excised under long-wave UV, the DNA extracted from the gel using the BIO 101 (Irvine, Calif., U.S.A.) Geneclean™ system, and cloned into the EcoRV site of pMOSBlue (blunt ended cloning kit from Amersham Pharmacia Biotech, Piscataway, N.J., U.S.A.) according to the manufacturer's instructions to create pMOSBlue(Flg).

pMOSBlue(Flg) was electroporated into *E. coli* JM83 cells using a Bio-Rad (Hercules, Calif., U.S.A) Gene Pulser™ (1.8 kV, 25 F, 200 ohm) according to the manufacturer's instructions and plated onto Luria agar plates containing ampicillin (50 µg/ml) and tetracycline (15 µg/ml). For blue/white selection, 35 l of X-gal (5-bromo-4-chloro-3-indolyl- -D-galactopyranoside) (50 mg/ml) and 20 l of IPTG (isopropyl- -D-thiogalactopyranoside) (100 mM) was spread onto plates. Plates were incubated overnight at 37° C. The tetracycline ensures that the selectable phenotype containing LacZ M15 is maintained and thus eliminates the background of non-recombinant white colonies which have lost the phenotype. Transformant colonies were picked into Luria broth containing ampicillin (50 µg/ml) and tetracycline (15 µg/ml), and incubated with shaking at 37° C. overnight. Plasmid DNA was extracted using a Qiagen (Hilden, Germany) plasmid purification kit and sequenced in both directions by the University of Cape Town (Microbiology Department; Cape Town, South Africa) DNA sequencing service using standard T7 and U-19 mer primers. On comparison, the *B. halodurans* Alk36 hag ORF demonstrated 100% identity in nucleotide sequence to the *B. halodurans* C-125 hag ORF (FIG. 4).

Cloning the Flanking Regions of the hag Gene Fragment Using Inverse PCR.

Figure 5:
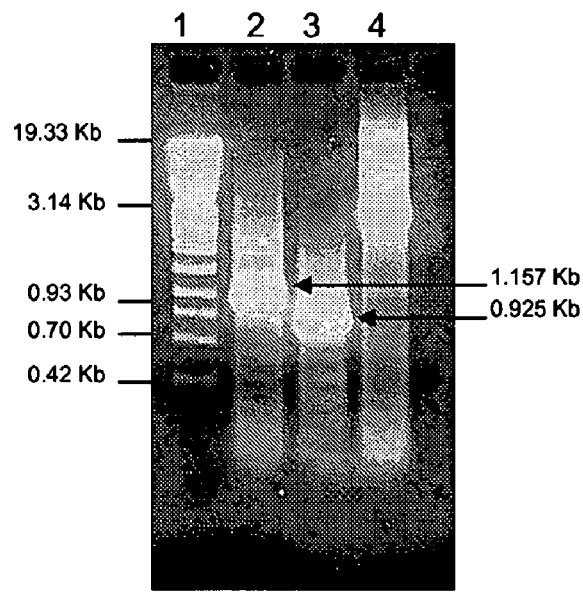
FIG. 5 is a photograph of an ethidium bromide-stained agarose (1%) electrophoretic gel showing inverse-PCR products obtained from B. halodurans Alk36 chromosomal digests. Lane 1, size markers; lane 2, AccI digest (10 l); lane 3, HindIII digest (10 l); lane 4, positive control (plasmid containing flagellin DNA fragment, ScaI digested). The positions of size markers (in Kb) are indicated on the left side of the photograph and the positions on the blot of fragments of 1.157 Kb and 0.925 Kb are indicated by arrows on the right of the photograph.

To complete the cloning of *B. halodurans* Alk36 hag, including its upstream and downstream regulatory regions, the ORF flanking regions were amplified using inverse PCR (iPCR). The method used for iPCR was adapted from the method by Ochman et al., [(1990) Amplification of flanking sequences by inverse PCR. In PCR Protocols: A Guide to Methods and Applications (ed. Innis M. A. et al.), p. 219-227. Academic Press, Inc.] *B. halodurans* Alk36 chromosomal DNA was digested with a variety of restriction enzymes so as to identify restriction enzymes that "restrict" the core region only once and generate fragments of approximately 1 kb flanking the known 800 bp fragment which could be easily amplified. The digested chromosomal DNA was separated on a 1% agarose gel, blotted onto Immobulon-P membrane (Millipore) as described by Reed et al. [(1985) Nucleic Acids Res. 13:7207-7221] and probed with the DIG-labeled 800 bp fragment according to the manufacturer's specifications (Boehringer Mannheim, Mannheim, Germany). The DIG-labeled bands were detected using a chemiluminescent reaction (Boehringer Mannheim). From the blot (FIG. 5), it was concluded that the most promising digests were the HindIII (for the downstream region) and AccI (for the upstream region) digests.

Protocol for Inverse PCR (iPCR)

*B. halodurans* Alk36 chromosomal digests (HindIII and AccI) were separated on a 1% low-melting agarose gel. After electrophoresis, the region of the gel containing the appropriate sized fragments was excised with a razor blade. The gel slice was heated to 68° C. for 20 min to melt the agarose. The DNA fragments were re-ligated under conditions to favour the formation of monomeric circles in a total reaction volume of 50 l containing 10 l of the molten agarose, 5 l of a 10× ligation buffer, 34 l of distilled H$_2$O, and 1 Weiss unit of T4 DNA ligase. The reaction was incubated overnight at 15° C. and terminated by heating to 68° C. for 15 min. 10 l of a ligation mix was used in a 100 l PCR reaction using the following primers:

```
IF:
5' GCT GAG TCT CGT ATC CGT GAC    (SEQ ID NO:30)
(Tm - 56.2° C.))

IR:
5' CCT GCA GCA TCG TCT CCT GCA    (SEQ ID NO:31)
(Tm - 58.1° C.)
```

The PCR reaction was set up as described above and incubated at 94° C. for 2 minutes, followed by a 3-step cycle of 94° C. for 1 minute, 50° C. for 1 minute, and 72° C. for 2 minutes, repeated a total of 35 cycles. A final extension step of 5 minutes at 72° C. was included.

After completion of the iPCR, the reaction products were resolved on a 1% agarose gel and visualized by ethidium bromide staining. From the gel (FIG. 6) it can be seen that PCR products of approximately 1.15 kb and 0.925 kb were amplified with the AccI and HindIII digests respectively. The size of the PCR products correlated well with the results obtained from the southern blot.

Figure 8A:
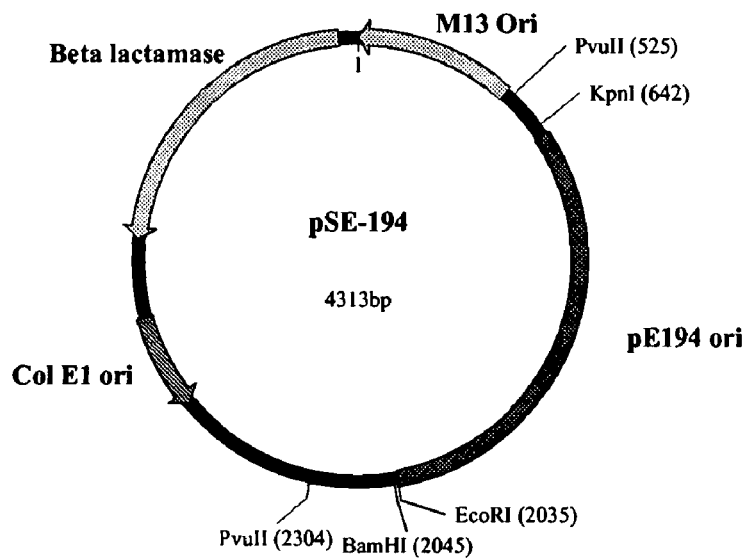
FIG. 8A is a depiction of the pSE194 (4.313 kb) plasmid map.
Figure 8B:
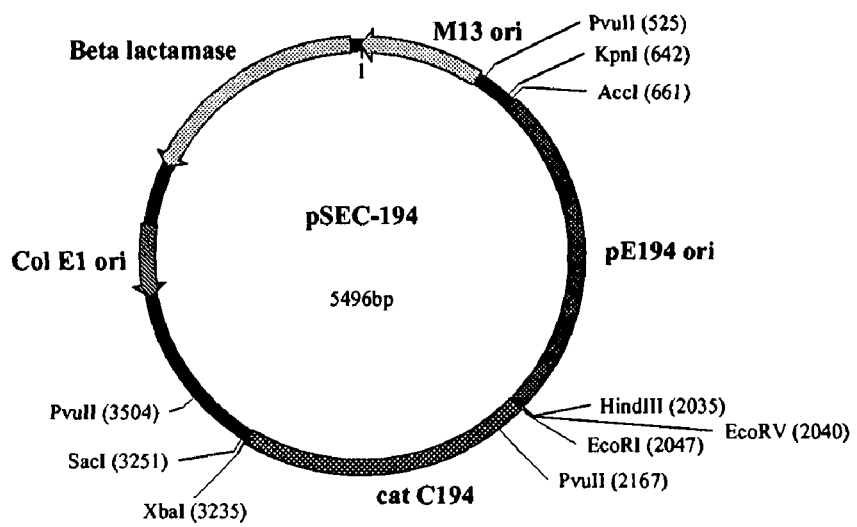
FIG. 8B is a depiction of the pSEC194 (5.496 kb) plasmid map.

The PCR reactions were purified using the High Pure™ PCR purification kit (Boehringer Mannheim). The resulting DNA was used for sequencing with the same two primers as primers for the PCR reactions. DNA sequencing confirmed that both PCR fragments contained the correct up- and downstream regions. The two fragments were cloned into the pMOSBlue vector and again sequenced using the T7 and U19-mer primers. This confirmed the initial sequence of the iPCR sequenced samples. The two clones generated 977 bp of new sequence data upstream of the 800 bp core region and 796 bp downstream (FIG. 7). These sequences are sufficient to include both upstream and downstream regulatory regions. These regulatory region sequences were compared to those of *B. halodurans* C-125 and found to demonstrate significant identity (greater than 99.9%), with only four differing base pairs. The complete hag gene with its regulatory regions is shown in FIG. 8.

Example 4

Inactivation of the Endogenous *B. halodurans* Alk36 Chromosomal Flagellin Gene

The plasmid pE194 (DSMZ 4554) was obtained from the German culture collection DSMZ (Deutsche Sammlung von Mikroorganismen und Zellkulturen GmbH, Mascheroder weg 1b, 38124 Braunschweig, Germany). Plasmid pE194 was isolated from *Staphylococcus aureus* bacteria, transformed into *Bacillus subtilis* bacteria, and shown to be stably maintained at temperatures up to 34° C. However, at temperatures higher than 37° C. the copy number decreases with plasmid loss by segregation [Weisblum et al. (1979) J. Bacteriol. 137:635-643]. Above 42° C. the plasmid cannot replicate and the only way the cell can survive on chloramphenicol is by integrating the plasmid into the chromosome. A shuttle-vector (pSEC194) was created using only the origin of replication from pE194, the chloramphenicol gene from pC194, and the *E. coli* origin of replication as well as the (-lactamase) gene from the Bluescript® pSK vector from Stratagene (La Jolla, Calif., U.S.A). Since pE194 is unstable at temperatures above 37° C. and is unable to replicate above 43° C., this feature was used to force an integration event in *B. halodurans* Alk36.

All *B. halodurans* Alk36 strains were transformed using the protoplast transformation method according to Chang and Cohen [(1979) Mol. Gen. Genet. 168:111-115].

Construction of Shuttle Vector pSEC194

The *Bacillus/E. coli* shuttle vector (pSEC194) was constructed by replacing the erythromycin resistance gene on pE194 with a chloramphenicol resistance gene and ligating the pSK ori to the pE194 ori. Plasmid pE194 was digested with TaqI. The 1.35 kb band containing the ori was ligated to pSK digested with ClaI (2.959 kb) and transformed into *E. coli* DH10B to create pSE194 (FIG. 9A). Plasmid pJM103 was digested with BglII/PvuII to obtain the chloramphenicol gene (1.2 kb) originally from pC194, [Iordanescu et al. (1980) Plasmid 4:256-260]. The fragment containing the gene was ligated to pSE194 digested with BamHI/SmaI and transformed into *E. coli* DH10B to create pSEC194 (FIG. 9B). It was important to screen for transformants in *E. coli* on plates containing ampicillin since screening with chloramphenicol led to deletions in the construct. However, when pSEC194 was transformed into *B. halodurans* and chloramphenicol was used as a marker, clones obtained were stably maintained at 30° C.-34° C. This vector was used as a shuttle vector between *E. coli/B. halodurans* Alk36 and *B. subtilis* and for the integration of genes of interest into the *B. halodurans* Alk36 chromosome.

Construction of Integration Vector pSEC194Flg-

A defective (endogenous gene-disrupting) hag gene was constructed using only the N- and C-terminal ORF regions, as well as some of the upstream and downstream regulatory regions, ligated into pSEC194 and transformed into *B. halodurans* Alk36. In the construction of pSECFlg- most of the internal region of the hag gene (FIG. 10A) has been deleted. The following primers were used to obtain the two PCR products needed for construction of the Flg- fragment:

```
UPFor:
                                        (SEQ ID NO:32)
5' GC GGA TCC GTG TGG TGA CAT TTG AC 3'
   (BamHI)

UPRev:
                                        (SEQ ID NO:33)
5' GC TCT AGA CGA TGC GCA TTC ATT GCT GG 3'
   (XbaI)

DownFor:
                                        (SEQ ID NO:34)
5' GC TCT AGA GAG TCT CGT ATC CGT G 3'
   (XbaI)

DownRev:
                                        (SEQ ID NO:35)
5' CG CTG CAG AAG AGG AAC GTA AAC G 3'
   (PstI)
```

The PCR products were obtained using standard procedures with appropriate optimization and were ligated together into pBCKS (Stratagene), digested with BamHI/PstI in a 3 way ligation to obtain the Flg- fragment. pBCFlg- was then digested with EcoRI and cloned into pSEC194 digested with EcoRI to obtain pSECFlg- (FIG. 10B).

the protocol used for integration was a combination of two different methods described by Biswas et al. [(1993) J. Bacteriol. 175:3628-3635] and Poncet et al. [(1997) Appl. and Environ. Microbiol. 63:4413-4420]. A first crossover (single crossover (sco)) event was forced by incubation of the *B. halodurans* Alk36 transformants containing pSEC194Flg- picked into 25 ml LB (pH 8.5) with chloramphenicol (10 μg/ml) at 52° C. for 16-24 hours. Serial dilutions of the resulting cell suspension were made and plated onto LA Luria agar (pH 8.5, 10 μl/ml chloramphenicol) and LA (pH 8.5) plates and incubated overnight at 52° C. Growth on LA (pH 8.5, 10 μl/ml chloramphenicol) and LA (pH 8.5) plates was compared to determine integration efficiencies. The sco event was determined with colony PCR (FIG. 11). Two chloramphenicol resistant clones, 49 and 50, were identified and clone 49 was then used to create a second cross-over (double cross-over (dco)) event. This was achieved by subsequent incubation of clone 49 in 25 ml LB Luria broth (pH 8.5) for 2-2½ hrs (log phase) at 30° C. in the absence of chloramphenicol. The culture was diluted and plated onto LA (pH 8.5) plates, and incubated at 30° C. overnight. Colonies were picked in duplicate onto LA (pH 8.5, 10 μl/ml chloramphenicol) and LA (pH 8.5) plates. Colonies in which gene replacement had occurred (dco) were chloramphenicol sensitive and non-motile. Chloramphenicol sensitive colonies were picked onto motility assessment plates (Luria plates, pH 8.5, 0.4% agar+0.8% gelatin) to screen for non-motile mutants. A non-motile dco mutant was screened for a dco event by colony PCR (FIG. 10). This mutated non-motile culture was renamed as Strain BhFC01. The double crossover was essential in order to ensure the loss of the chloramphenicol gene, which was also indicative of loss of plasmid sequences, thereby producing a *B. halodurans* Alk36 mutant strain BhFC01 (hag) having a defective hag gene, and demonstrating a non-motile phenotype (motility plates; FIG. 15A).

Different primer sets were used to demonstrate the dco event:

The Sig$^D$F/InvR primer combination was predicted to give a PCR product of 342 bp if an intact hag gene is present on the chromosome.

The Sig$^D$F/FliCR primer set was predicted to amplify both the defective (400 bp) and intact hag (1.150) kb genes present on the chromosome. Only the defective band was shown to be present in the two sco events (FIG. 11, Primer Set B, lanes 1 and 2) even though an intact copy was shown to be present using the Sig$^D$/InvR primer set (FIG. 11, primer set B, lane 1). It seemed likely that the primers preferentially amplify the defective copy. An analogous result was reported by Aquino de Muro et al. [(2000) Res. Microbiol. 151:547-555]; in that study a very prominent band was observed for one copy and a very faint band for the other.

The Sig$^D$F/M13R primer set was predicted to amplify only the hag gene if there was plasmid DNA present on the chromosome, which had been obtained from a sco event. After the dco, all plasmid DNA should be looped out and no PCR product should be obtained. This is what was observed (FIG. 11, primer set C, lanes 3 and 4). The size of the PCR product (sco) was expected to be 2.507 kb (defective hag) or 3.178 (intact hag) depending on whether or not there has been an N-terminal or C-terminal cross-over. Appropriate sized bands were observed.

The UpFor/DownRev primer set was expected to amplify either the defective or complete hag gene depending on the location of the cross-over. As predicted, an N-terminal crossover (defective hag) yielded a PCR product of 1.735 kb (FIG. 11, primer set D, lanes 1-3) and a C-terminal cross-over (intact hag) a product of 2.406 kb (FIG. 11, primer set D, lane 4). After the dco only the smaller band was amplified.

The results obtained from the PCR profiles showed that a dco event was obtained resulting in a flagellin-mutant BhFC01. The next step was to confirm that the mutation was in the hag gene by complementation of the mutation with an intact copy of the hag gene on pSEC194.

Example 5

Complementation Studies Demonstrated Restoration of Flagellin Expression in Strain BhFC01

Primers used for these experiments were:

```
FliCR:
                                        (SEQ ID NO:36)
5' CAA CAA AGT AAC GGT TGA GCG 3'

InvR:
                                        (SEQ ID NO:37)
5' CCT GCA GCA TCG TCT CCT GCA 3'

Sig^P F:
                                        (SEQ ID NO:38)
5' CTC GGT ACC CTC GCG TTA CGC TCT TTC TGT 3'
(KpnI)

UPFor:
                                        (SEQ ID NO:32)
5' GC GGA TCC GTG TGG TGA CAT TTG AC 3'
(BamHI))

DownRev:
                                        (SEQ ID NO:35)
5' CG CTG CAG AAG AGG AAC GTA AAC G 3'
(PstI)

M13R
                                        (SEQ ID NO:39)
5' GGA AAC AGC TAT GAC CAT G 3'
```

The complete hag gene containing the $\sigma^D$ promoter as well as the coding sequence was cloned into pSEC194 and transformed into Strain BhFC01. Plasmid pSEC194FliC (containing the intact flagellin promoter and structural gene), was introduced into BhFC01 by protoplast transformation to assess the ability to compliment the genomic hag deletion with multiple copies of the gene. Transformants were toothpicked onto motility assessment plates and showed clear movement of strain BhFC01 containing pSEC194FliC (FIG. 15). A cell-surface protein extract was obtained of the Strain BhFC01 as in Example 1 and resolved by SDS-PAGE. A protein resolving to a band corresponding to .about.34 kDa demonstrated recovery of flagellin protein expression in Strain BhFC01 transformants (FIG. 14A, lane 6).

Example 6

Protein Modeling of the Variable Region of *B. halodurans* Alk36 Flagellin and Construction of Fusion Protein Expression Vectors 3D-PSSM (three-dimensional, position specific scoring matrix) is a fast, Web-based method for protein fold recognition using 1D and 3D sequence profiles coupled with secondary structure and solvation potential information. A summary of the protocol can be found in the Journal of Molecular Biology, 299:501-522 (Kelley et al. 2000) the disclosure of which is incorporated herein by reference in its entirety. The putative variable region of *B. halodurans* Alk36 flagellin was modeled using 3D-PSSM-software. From the protein model five sites were chosen within the variable region which would allow for peptide insertions. All these sites are situated or involve the manipulation of the externally exposed extendedstrands and coils of the variable region of the *B. halodurans* FliC protein (FIG. 12). Five constructs were created, using the vector pSEC194 KpnI/HincII as the backbone.

The NC1 construct contained a deletion of the flagellin variable region and an insertion of a nine amino acid peptide, while the NC2, NC3, NC5 and NC6 constructs contained insertions of peptides of various sizes.

Construction of pSEC194NC1 pSEC194FliC was used as template to obtain the N and C terminal regions by PCR amplification according to standard procedures with appropriate optimization for the construction of the truncated hag gene (pSEC194NC1). pSECFliC was digested with KpnI/EcoRI to obtain the N-terminal fragment (566 bp). PCR amplification using the FliCR and CterF primers was used to obtain the C-terminal fragment (232 bp).

```
FliCR:
                                        (SEQ ID NO:36)
5' CAA CAA AGT AAC GGT TGA GCG 3'

CterF:
                                        (SEQ ID NO:40)
5' CGC GAA TTC CTA GGA GCT ATG CAA AAC C 3'
(EcoRI)
```

The C-terminal PCR fragment was digested with EcoRI/DraI and ligated with the N-terminal fragment (KpnI/EcoRI) to pSEC194 digested with KpnI/DraI in a 3-way ligation. The resulting truncated flagellin (FliC) protein has a deletion of 89 amino acids from amino acids 114-202. This deletion spans a large area of the variable region of the FliC protein.

Construction of pSEC194NC2 pSEC194NC2(NC2) was obtained by inserting a 15 bp (corresponding to 5 amino acids) multiple cloning site (MCS) insert after nucleotide (nt) 606 of the open reading frame (FIG. 13A). The N-terminal region was PCR amplified using the primers Sig$^P$Kpn and FliN-terRev (see below) and the C-terminal region was PCR amplified using the primers CterF2 and DownRev (see below) using standard procedures with appropriate optimization. *B. halodurans* Alk36 genomic DNA was used as the template for all PCR reactions.

```
FliN-terRev:
                                        (SEQ ID NO:41)
5' CTC CTC GAG CGA CCT TCT GAA ACA GC 3'
(XhoI))

Sig^P Kpn:
                                        (SEQ ID NO:42)
5' CTC GGT ACC CTC GCG TTA CGC TCT TTC TGT
(KpnI)

CterF2:
                                        (SEQ ID NO:43)
5' CAC GAA TTC TCG AGC CCG GGA TCC TCT TCA CTA GGA
GCT ATG CAA AAC 3'
(EcoRI, XhoI, SmaI, BamHI)

DownRev:
                                        (SEQ ID NO:35)
5' CGC TGC AGA AGA GGA ACG TAA ACG 3'
(PstI)
```

The N-terminal fragment was digested with XhoI/KpnI and the C-terminal fragment with XhoI/SspI. pSEC194 was digested with KpnI/HincII and a 3-way ligation resulted in pSEC194NC2.

Construction of pSEC194NC3 pSEC194NC3 differed from pSEC194NC2 in the position of the insert (after nt 459 of rather than nt 606) and the size of the insert (27 bp corresponding to 9 amino acids) (FIG. 13B). The N-terminal region was PCR amplified using the primers Sig$^D$Kpn and VNR2 (see below) and the C-terminal region was amplified using the primers VCF and DownRev (see below) according to standard procedures with appropriate optimization. The template for both reactions was *B. halodurans* Alk36 genomic DNA.

```
Sig^DKpn:
                                              (SEQ ID NO:42)
5' CTC GGT ACC CTC GCG TTA CGC TCT TTC TGT
(KpnI))

VNR2:
                                              (SEQ ID NO:44)
5' CGG CAG CTG TTC ACC AGA ATT AGC ACC AAC 3'
(PvuII)

VCF:
                                              (SEQ ID NO:45)
5' CAC GTC GAC TCG AGC CCG GGA TCC TTA ATT GAA CTT
GAT TTA ACA AAA G 3'
(SalI, XhoI, SmaI, BamHI)

DownRev:
                                              (SEQ ID NO:35)
5' CGC TGC AGA AGA GGA ACG TAA ACG 3'
(PstI)
```

The C-terminal PCR fragment was digested with SalI and PstI and ligated into the pSK vector that had been digested with the same two restriction enzymes to create pSKCter. The N-terminal fragment was digested only with KpnI (the other end was left blunt) and then ligated to pSKCter digested with HincII and KpnI to create pSKNC3. This construct was digested with KpnI and SspI to liberate the NC3 fragment which was then ligated to pSEC194 digested with KpnI and HincII to obtain pSEC194NC3.

Construction of pSEC194NC5 pSEC194NC5 was generated by inserting 21 nucleotides (corresponding to 7 amino acids after nt 387 of (FIG. 13C). The N-terminal region was PCR amplified using primers NC5R and Sig$^D$Kpn (see below) and the C-terminal was amplified using primers NC5F and DownRev (see below) using standard procedures with appropriate optimization. *B. halodurans* genomic DNA was used as the template for all PCR reactions.

```
NC5F:
                                              (SEQ ID NO:46)
5' CAC GTC GAC TCG AGC CCG GGA TCC TTT AAT ACG CAA
AAA TTA CTC 3'
(SalI, XhoI, SmaI, BamHI)

Sig^DKpn:
                                              (SEQ ID NO:42)
5' CTC GGT ACC CTC GCG TTA CGC TCT TTC TGT
(KpnI)

Down Rev:
                                              (SEQ ID NO:35)
5' CGC TGC AGA AGA GGA ACG TAA ACG 3'
(PstI)

NC5R:
                                              (SEQ ID NO:47)
5' CAC CTC GAG TGA GTTGTA TCT TTG ATT C 3'
(XhoI)
```

The N-terminal PCR fragment was digested with KpnI and XhoI. The C-terminal was generated using pwo DNA polymerase (Roche Diagnostics, Basel, Switzerland) and this resulted in a blunt ended PCR product. The C-terminal PCR fragment was then restricted with XhoI and used in a 3-way ligation resulting in pSEC194NC5.

Construction of pSEC194NC6 pSEC194NC6 was generated by inserting 27 bp (corresponding to 9 amino acids after nt 540 of (FIG. 13D). The N-terminal (767 bp) region was PCR amplified using primers SigDKpn and VNR6 and the C-terminal (349 bp), with primers VCF6 and DownRev. The C-terminal product was restricted with SalI/PstI and ligated into pSK restricted with SalI/PstI to obtain pSKCter2. Plasmid pSKCter2 as well as the N-terminal PCR product was restricted with KpnI/SalI and ligated to produce the plasmid pSKNC6. The NC6 fragment from pSKNC6 was PCR amplified with PWO taq using primers SigDKpn and FliCR to obtain a blunt ended PCR product, which was then restricted with KpnI and ligated into pSEC194 (KpnI/HincII) to obtain pSEC194NC6.

```
FliCR:
                                              (SEQ ID NO:36)
5' CAA CAA AGT AAC GGT TGA GCG 3'

Sig^DKpn:
                                              (SEQ ID NO:42)
5' CTC GGT ACC CTC GCG TTA CGC TCT TTC TGT 3'
(KpnI)

VNR6:
                                              (SEQ ID NO:48)
5' GAC GTC GAC AGT GTG GTC AGT AAT ATC CTC 3'
(SalI)

VCF6:
                                              (SEQ ID NO:49)
5' CAC GTC GAC TCG AGC CCG GGA TGG ATC CAG AAT GCA
CAA TCA GCT ATT GAC 3'
(SalI)

DownRev:
                                              (SEQ ID NO:35)
5' CGC TGC AGA AGA GGA ACG TAA ACG 3'
(PstI)
```

In all cases the insert was designed to carry a multiple cloning site (MCS) for the addition of sequences encoding heterologous peptides and proteins. All the NC constructs were generated to identify the functional insertion sites within the FliC protein, determine the level of expression, and observe phenotypic (restoration of motility in *B. halodurans* BhFC01) characteristics after transformation. Cell-surface protein (CS) extracts were produced from *B. halodurans* Alk36 cultures transformed with NC1, NC2, NC3, NC5 and NC6 respectively, and the protein extracts resolved by SDS-PAGE as before. BhFC01 containing the NC3 and NC6 constructs were found to over-express a protein resolving to a band corresponding to that of the FliC protein. (FIG. 14A, lanes 1-5 and FIG. 14B, lanes 2-3). From the electrophoretic gel it is clear that the levels of the modified FliC protein produced by the BhFC04 (NC6) strain compared well with that of WT (wild-type) bacteria. NC6 was the only construct that restored motility to *B. halodurans* non-motile mutants (FIG. 15).

The ~34 kDa protein band in the cell surface (CS) fraction was confirmed to be flagellin, or modified flagellin, by Western Blot analysis (FIG. 14C) with FliC-specific antibodies.

Example 7

Directed Inactivation of the Cell Wall Protease-Encoding wprA gene on the Chromosome of *B halodurans* Strain BhFC01 using the pSEC194 Integration Vector The wprA gene encodes a cell wall protease that could decrease levels of fusion proteins expressed on the surface of relevant recombinant bacteria. A strategy was devised to delete the wprA gene in BhFC01 bacteria.

The plasmid pSECwprA- was constructed by deleting 1056 bp of the internal region of the wprA gene (FIG. 16A). This region included the entire wprA coding sequence. FIG. 16B shows the amino acid sequence of the wprA protein. The following primers were used to obtain the N- and C-terminal PCR products needed for construction of the wprA- fragment.

```
N-For:
                                         (SEQ ID NO:50)
5' GC GAG CTC TGC AGC GTA CTA CAA CCA 3'
(SacI)

N-Rev:
                                         (SEQ ID NO:51)
5' GC GGA TCC AGC TGA TAA CGC TAC GTA 3'
(BamHI)

C-For:
                                         (SEQ ID NO:52)
5' GC GGA TCC TAG CGG ACC TGT AGA TGC TA 3'
(BamHI)

C-Rev:
                                         (SEQ ID NO:53)
5' GG TCT AGA TGC CTT GTC CTT CGC TGT A 3'
(XbaI)
```

The PCR products were digested and ligated together into pSEC194 restricted with SacI/XbaI to obtain pSEC194wprA- (FIG. 16B). The plasmid pSEC194wprA- was transformed as before into strain BhFC01. A transformant containing a sco was used to force a dco event as described in Example 4. The strain obtained was named BhFC04 (hag, ΔwprA). The extracellular and cell surface proteins of *B. halodurans* strains BhFC01 and BhFC04 were extracted and protein and protease profiles were obtained on SDS-PAGE and gelatin-SDS-PAGE gels (FIG. 17).

Results obtained from a reporter gene in both strains showed improvement of protein production and stability in the different fractions of BhFC04 (results not shown). The plasmids pSEC194NC3 and pSEC194NC6 were then transformed into strain BhFC04 to improve production and stability of the modified FliC proteins on the surface.

Applicants deposited under the Budapest Treaty the BhFC04 (Δhag, ΔwprA) *B. halodurans* strain with the NCIMB Culture Collection (NCIMB Ltd, Ferguson Building, Craibstone Estate, Bucksburn, Aberdeen, AB21 9YA) under accession number NCIMB on 28 Nov. 2006. The BhFCO4 strain was assigned the NCIMB accession no. 41357. The strain deposited with the NCIMB culture collection was taken from a deposit maintained by the Council for Industrial and Scientific Research (CSIR) since prior to the priority date of this application. The deposits of the strain will be maintained without restriction in the NCIMB depository for a period of 30 years, or five years after the most recent request, or for the effective life of the patent, whichever is the longer, and will be replaced if the deposit becomes non-viable during that period.

Example 8

Surface Display of Fusion Proteins

Bioremediation and Bio-Mining: Surface Display of a poly-His tag Peptide

Construction of pSEC194NHisC6 pSEC194NHisC6 was constructed as an example of display of a metal binding peptide (poly-His tag) on the surface of strain BhFC04 using the NC6 insertion site. The poly-His tag (containing six histidine residues) has previously been shown to bind Cadmium, Nickel and Copper [Sousa et al. (1996) Nature Biotech. 14:1017-1020]. The tag was thus suitable to demonstrate the use of the flagellin display system for bioremediation or bio-mining of precious metals in the mining industry.

pSEC194NHisC6 was constructed by restricting 3 g pSEC194NC6 with XhoI and BamHI. The poly-His tag was generated by annealing two complimentary oligonucleotides (HisF3 and HisR3; see below) using a method described by IDT (Integrated DNA Technologies, Coralville, Iowa, U.S.A.).

```
HisF3
                                         (SEQ ID NO:54)
    5' TCG AGA CAT CAT CAT CAT CAT CAC AG

HisR3
                                         (SEQ ID NO:55)
    5' GAT CCT GTG ATG ATG ATG ATG ATG TC
```

Briefly, the two oligonucleotides (oligos) were diluted separately in STE buffer (10 mM Tris pH 8, 50 mM NaCl, 1 mM EDTA) at a final concentration of 50 M. An equal volume of each oligo solution was mixed together and diluted to a final concentration of 5 M. The mixture of oligos was heated to 100° C. in a boiling waterbath and then allowed to cool slowly to room temperature by switching off the waterbath. The annealed oligos were purified using the Geneclean™ III Kit (BIO 101). The annealed oligos contained a XhoI and BamHI site at the 5' and 3' ends respectively.

```
5' TCG AGA CAT CAT CAT CAT CAT GAC AG BamHI   (SEQ ID NO:56)

XhoI CT GTA GTA GTA GTA GTA GTG TCC TAG 3'    (SEQ ID NO:57)
```

Ligation of the annealed poly-His tag to the restricted pSEC194NC6 was done according to the Fast-Link™ DNA ligation kit (Epicentre, Madison, Wis.) to give pSEC194NHisC6. 20 ng of pSEC194NC6 and 30 ng annealed His oligo were used in the ligation reaction. The reaction was stopped by heat inactivation at 70° C. for 15 minutes. Two l of the ligation mix was transformed into E. coli DH10B cells by electroporation (25 F, 200 Ohms, 1.6 KV). Clones were screened using colony PCR analysis (25 l) using primers HisF3 and FliCR (5' CAA CAA AGT AAC GGT TGA GCG 3'). Clones were picked into 50 l sterile water and boiled for 5 minutes. Boiled colonies were centrifuged at 12,000 rpm for 30 seconds to pellet cell debris. 5 l of boiled lysate was used in each PCR reaction. Reaction mixtures were as follows, 2.5 l 10× Buffer, 2.5 l 8 mM dNTP's, 0.75 l 50 mM MgCl, 1.25 l 5 M each primer, 0.2 l Taq polymerase (1 unit) and sterile PCR water to 25 l total volume. PCR parameters were: one cycle at 94° C. for 4 min, 35 cycles at 94° C. for 1 minute, 56° C. for 1 minute and 72° C. for 1½ minutes with a final extension of one cycle at 72° C. for 4 minutes. A single positive clone was grown up and plasmid DNA was isolated from the resulting culture. The amino acid sequence (and its encoding nucleotide sequence) of the poly-His peptide and amino acids encoded by parts of the MCS that form the inserted heterologous polypeptide are shown in FIG. 18. The full inserted peptide was 13 amino acids long.

Strain BhFC04 was transformed as described above with pSEC194NhisC6 to determine the metal binding capabilities of this construct. Transformants were confirmed to carry pSEC194NhisC6 with colony PCR's. BhFC04 clones carrying the pSEC194NhisC6 construct were grown in 25 ml LB broth pH 8.5 to determine both the successful display of the peptide but also its ability to bind to MagneHis Ni-Particles.

Production and Functionality of NHisC6 Protein

The locations of the displayed peptide in the bacterial cells were determined by isolating the extracellular (Ex), cell surface (CS), cell wall (CW) and intracellular (IC) protein fractions and separating the protein samples on a 10% SDS-PAGE gel. Fractions were isolated as follows.

Cells were grown at 30° C. in 25 ml Luria broth (LB) pH 8.5 to stationary phase (16 hours). Cells were pelleted and resuspended in 2.5 ml sterile phosphate buffer pH 7.5 and the cell pellet was used for the CS fraction (see next paragraph). The supernatant was precipitated by adding an equal volume of 5% trichloroacetic acid (TCA) and incubated for 30 min at room temperature. The precipitated proteins were pelleted by centrifugation at 17,000×g for 30 minutes and dried at 37° C. for 30 minutes. The protein pellet was resuspended in 300 μl of phosphate buffer pH 7.5 to produce the EX protein fraction.

An equal volume of 0.2M NaOH was added to the resuspended cell pellet and stirred vigorously with a stirrer bar for 30 minutes on ice. The cells were pelleted by centrifugation at 8,000×g for 10 minutes to remove cellular material and obtain the supernatant. An equal volume of 5% TCA (trichloroacteic acid) was added to the supernatant and the resulting mixture was incubated at room temperature with shaking for 30 minutes. Cell surface (CS) proteins were pelleted by centrifugation at 17,000×g for 30 minutes. The pellet was rinsed with sterile water and dried at 37° C. for 30 minutes. The CS proteins were then resuspended in 300 μl phosphate buffer pH 7.5. The cell pellet obtained after "stripping" with NaOH was resuspended in 5 ml phosphate buffer and sonicated for 30 minutes at full strength using a Sonopuls Ultrasonic homogenizer (Bandelin, Berlin, Germany). Lysed cells were centrifuged at 10,000×g for 10 minutes to precipitate the CW fraction. The supernatant (IC) was removed and placed in 2 ml eppendorf tubes. The CW pellet was dried at 37° C. for 30 minutes and resuspended in 500 l phosphate buffer pH 7.5. Protein concentrations were determined by the Bradford method (Bradford, 1976, Anal Biochem 72:248-259). CS fractions were separated on a 10% SDS-PAGE gel and stained using Coomassie stain (FIG. 19).

In order to determine the metal binding capacity of the displayed poly-His tag, the MagneHis™ protein purification system (Promega, Madison, Wis., U.S.A.) was used. This kit makes use of the His-tags ability to bind to nickel particles which can then be isolated using a magnet. Proteins can then be cleaved from the nickel particles using imidazole. Crude cell extracts were obtained by pelleting 6 ml of overnight cultures of pSEC194NHisC6 and pSEC194NC6 transformed bacteria (-ve control), and resuspending the pellets in 5 ml phosphate buffer. Each sample was sonicated as described for the IC extraction above. Proteins were precipitated with an equal volume of 5% TCA and resuspended in 600 l of lysis buffer (MagneHis Kit). All subsequent steps were performed according to the manufacturer's instructions under non-denaturing conditions. Proteins were eluted in a final volume of 100 l.

Successful binding of the His-tag to the MagneHis beads (nickel) were visualized by separating the samples on a 10% SDS-PAGE gel and staining with Coomassie blue (FIG. 20). Three fractions, including unbound proteins (lanes 6 and 7), the bead-bound proteins which were not eluted (lanes 4 and 5), and the bead-bound and eluted proteins (lanes 2 and 3), were included. The fusion of the poly-His tag to flagellin resulted in the successful display of this peptide in a functional form. The fact that the preparation was carried out under non-denaturing conditions also demonstrates that the peptide is displayed on the exposed domain of the flagellin as predicted by sequence alignment studies.

Surface Expression of Antigens: HIV (Human Immunodeficiency Virus) Peptide

Construction of pSEC194NHivC6 pSEC194NHivC6 was constructed to display a foreign antigenic epitope on the surface of *B. halodurans* strain BhFC04. Recombinant organisms such as these can be used as immunogens for generating immune responses of a variety of types and against antigens from a wide variety of sources. The $V_3$ loop portion of the HIV isolate HIV-1 was chosen as an example. The antigenic motif of the gp120 (V3 loop) was found to be conserved (Gly-Pro-Gly-Arg-Ala-Phe) and induces the production of neutralising antibodies. This epitope was also shown to activate both T-helper and cytotoxic T-lymphocyte responses [Goudsmit et al. (1988) Proc. Natl. Acad. Sci. USA. 85: 4478-4482; Javaherian et al. (1989) Proc. Natl. Acad. Sci. USA 86:6788-6772].

pSEC194NHivC6 was constructed by restricting pSEC194NC6 with XhoI and BamHI. The HIV gp120 antigenic epitope was generated by annealing two complimentary oligonucleotides (sequences below) as described above.

```
                                                   (SEQ ID NO:58)
                 XhoI
        HivF3B 5' CAC CTC GAG ACG TTC ATT ATC ATA TGG ACC AGG ACG
TGC
ATT TCG TAC GCG TTG GAT CCA CAG 3'
```

-continued

```
                BamHI
                                                          (SEQ ID NO:59)
          BamHI
    HivR3B 5' CTG TGG ATC CAA CGC GTA CGA AAT GCA CGT CCT GGT
CCA
TAT GAT AAT GAA CGT CTC GAG GTG 3'
                            XhoI
```

The annealed oligo's were restricted with XhoI and BamHI and purified as described above.

```
      5' - TC GAG ACG TTC ATT ATC ATA TGG ACC AGG ACG TGC ATT TCG TAC GCG TTG
BamHI    (SEQ ID NO:60)

XhoI C TGC AAG TAA TAG TAT ACC TGG TCC TGC ACG TAA AGC ATG CGC AAC CAT
G-3'     (SEQ ID NO:61)
```

Ligation of the HIV peptide to the restricted pSEC194NC6 was done using the Fast-Link DNA Ligation Kit (Epicentre) to give pSEC194NHivC6. 20 ng of pSEC194NC6 and 30 ng of the annealed HIV oligo were used in the ligation reaction. The ligation reaction was heat inactivated at 70° C. for 15 minutes.

Two l of the ligation mix was transformed into *E. coli* DH10B cells by electroporation (25 F, 200 Ohms, 1.6 Kv). Clones were screened by colony PCR analysis (25 l) using primers NC5F and FliN-terRev. PCRs were done as described above with the annealing time being reduced from 1½ minutes to 1 minute. All samples were analysed on a 1.5% TAE Agarose gel. A single positive clone grown up and plasmid DNA was isolated from the resulting culture. The amino acid sequence (and its encoding nucleotide sequence) of the HIV V3 loop peptide and amino acids encoded by parts of the MCS that form the inserted heterologous polypeptide are shown in FIG. 21. Sequences were confirmed to be correct and subsequently transformed into *B. halodurans* BhFC04 (hag, wprA).

Western Blot analysis using FliC-specific antibodies showed that the bands obtained on the SDS-PAGE gels were either FliC or functional FliC fusion proteins (FIG. 23).

Biotransformation

Construction of pSEC194NMLipC pSEC194NMLipC3 was constructed to demonstrate the use of the FliC display system for biotransformation. The examples described above focused on small peptides which can be used for bioremediation or antigenic determinants in vaccine development. Ezaki et al. [(1998) J. Ferm. Bioeng. 86:500-503] and Tanskanen [(2000) Appl. Environ. Micro. 66:4152-4156] both demonstrated that large polypeptides (471 and 302 amino acids in length could also be displayed successfully using *E. coli* flagellin. Lipases have been well characterised and play a role in a number of compositions and processes including, without limitation, detergents, glycerolysis of fats and oils, direct esterification, chiral resolution and acylate synthesis [Litthauer et al. (2002) Enz. Micro.

```
    NC5F:   5' CAC GTCGAC TCG AGC CCG GGA TCC TTT AAT ACG CAA AAA TTA CTC
    3'
            (Sa/I)  (SEQ ID NO:46)

FliN-terRev: 5' CTC CTCGAG CGA CCT TCT GAA ACA GC 3'  (XhoI)  (SEQ ID NO:41)
```

Strain BhFC04 was transformed as described above. Positive transformants were confirmed with colony PCR using primers FliN-terRev and NC5F. A single positive clone was chosen to isolate protein fractions as described above. 10 g of CS, 20 g of EX, 40 g of CW and 40 g of IC fractions were loaded onto 10% SDS-PAGE gels and stained using Coomassie blue stain.

On the SDS-PAGE gel, only the CS fraction gave a band resembling the correct size of the flagella-Hiv peptide fusion (FIG. 22). The inclusion of the peptide resulted in the insertion of a 21 aa peptide in the FliC protein and an increase in size of the flagella chimera of approximately 2.3 KDa that is clearly visible on the gel.

Figure 24:
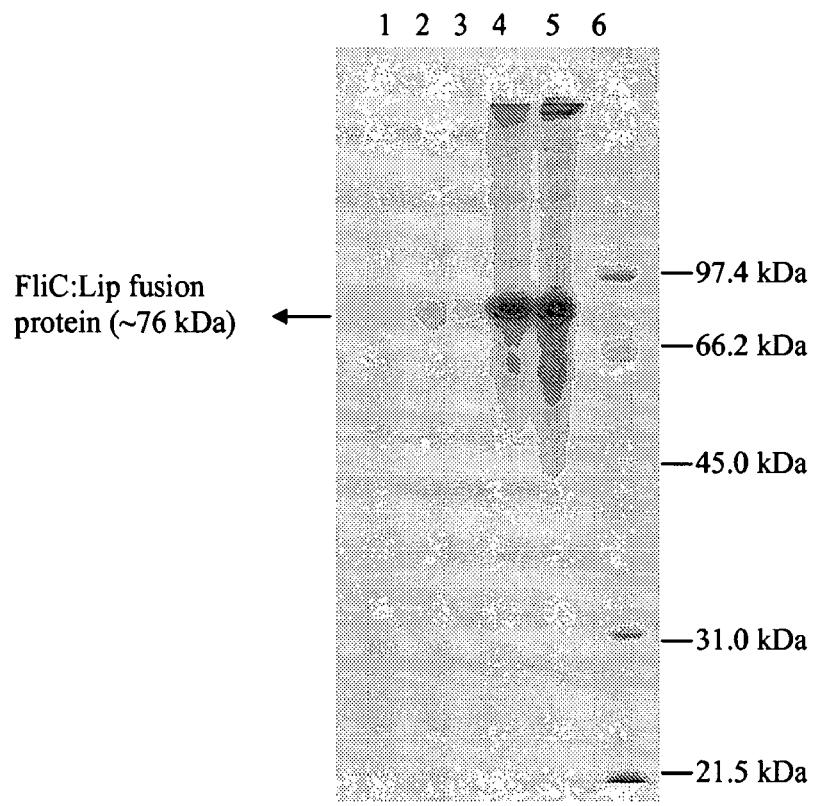

Tech. 30:209-215]. The use of lipases immobilized on the cell surface of *Staphylococcus carnosus* has been demonstrated using the fibronectin binding protein B fused to the *Staphylococcus hyicus* lipase [Strauss et al. (1996) Mol. Microbiol. 21:491-500].

pSEC194NLipC was constructed by restricting pSEC194NC3 with BamHI and XhoI. The mature lipase was PCR amplified from *G thermoleovorans* chromosomal DNA (LipA) so that the signal sequence was not present (FIG. 24). The primers used were LipFSD and LipR (see below). The PCR products were purified and restricted with BamHI and XhoI.

```
          LipFSD:  5' GTC CTCGAG GCT TCG CGA GCC AAC GAT G 3'  (XhoI)   (SEQ ID NO:62)

LipR:    5' GTC GGATCC AGG 000 GAA GCT CGC CA -3'  (BamHI)   (SEQ ID NO:63)
```

Ligation of the lipase polypeptide to the restricted pSEC194NC3 was done using the Fast-Link™ DNA Ligation Kit (Epicentre) to give pSEC194NLipC3. 20 ng of vector DNA and 60 ng of lipase were used for the ligation reaction. The ligation reaction was heat inactivated at 70° C. for 15 minutes. 2 l of the ligation mix was transformed into E. coli DH10B cells as described above. A single positive clone was selected for further analysis.

Figure 25:
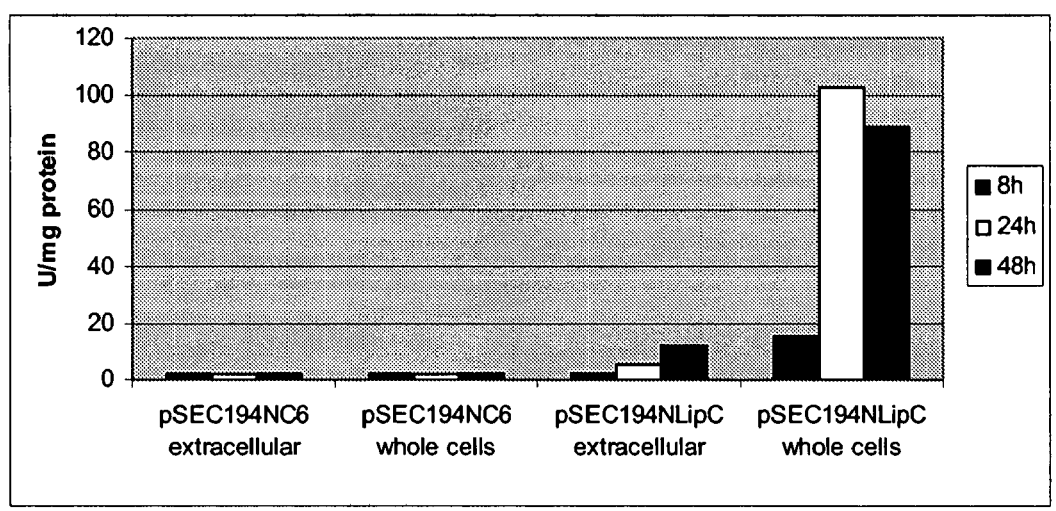

Transformation of B. halodurans BhFC04 with pSECNLipC and Determination of Lipase Activity B. halodurans strain BhFC04 transformation was carried as described above. Clones were screened using colony PCR with primers M13F (5'-GTA AAA CGA CGG CCA GT-3') and LipR. 50 ml LB containing chloramphenicol (10 g/ml) was inoculated from an overnight culture and grown to an $OD_{540}$ of 1.2-1.6. Protein fractions were isolated as described above except that 5 ml LiCl (5M), rather than NaOH, was used to strip the CS proteins from the cell surface. This allowed for maximum lipase activity as NaOH inactivated the lipase enzyme. The EX and CS fractions were TCA precipitated even though this method reduced lipase activity; sufficient activity remained to visualize on a zymogram (activity gel) (FIG. 25). However, this method naturally could not be used to accurately quantify the activity in the EX and CS fractions. Nevertheless, the activity gel is a useful tool for determining the actual size and stability of the fusion protein and performed as described by Takahashi et al. [(1998) J. Ferm. Bioeng. 86:164-168]. Samples were prepared by adding non-denaturing loading dye and incubation for 30 min at 37° C. SDS-PAGE gels were run at a constant current of 30 mA until the dye front reached the end of the gel. The gels were incubated overnight in 25 mM Tris pH 7.5 and 2.5% Triton X-100 to remove the SDS, transferred to equilibration buffer (25 mM Tris pH 7.5) for 30 min, and then stained for lipase activity using 0.1% -naphthyl acetate and 0.2% Fast Red TR Salt in equilibration buffer. The reaction was stopped with 2 washes of TE buffer (10 mM Tris, pH 8, 1 mM EDTA) once the bands could be clearly seen.

Lipase activity was observed in the CS, CW and intracellular fractions but not in the extracellular fraction. These findings indicated that the FliC-lipase fusion remains firmly bound to the CW and CS fractions and are exposed on the cell surface. The reduced activity in the CS fraction was possibly due to the TCA which inactivates lipase. These results also indicate that the fusion protein is very stable.

The next step was to quantify the lipase activity produced in liquid cultures (FIG. 26). Overnight cultures of BhFC04 transformed with pSEC194NC6 (control) or pSEC194NLipC constructs were grown in Luria Broth pH 8.5, chloramphenicol 10 μg/ml at 30° C. Two flasks containing Luria Broth pH 8.5 (60 ml) containing chloramphenicol 10 μg/ml were inoculated from the ON cultures to give a starting $OD_{540}$ of 0.1. The flasks were incubated at 30° C. and samples taken at 8, 24 and 48 hours. Whole cell and extracellular samples were used for lipase assays. Lipolytic activity was determined essentially according to Vorderwülbecke et al. [(1992) Enzym Microb. Technol. 14: 631-639], by a spectrophotometric assay using p-nitrophenyl-palmitate as substrate. Assay solution 1 was prepared by dissolving 90 mg p-nitrophenyl-palmiate in 30 ml propan-2-ol. Assay solution 2 contained Na-deoxycholate (2 g) and gum Arabic (0.5 g) dissolved in 450 ml Tris-HCl buffer pH8. Emulsion solution was prepared by adding 1 ml of assay solution 1 to 9 ml of assay solution 2. Under standard conditions, the assays were performed by incubating 600 μl of emulsion solution and 25 μl enzyme preparation.

The reaction was performed at 65° C. and the absorbance measured at 410 nm. Lipase activity was calculated as U/ml (μmol fatty acids/min/ml enzyme). The extinction coefficient of p-nitrophenol at 410 nm (pH8) is 15 ($1 \times nmol^{-1} \times cm^{-1} = ml \times cm^{-1}$). Protein concentrations of enzyme samples were determined by the method of Bradford (1976) using bovine serum albumin dilutions as standards. Final activity was expressed as U/mg total protein as shown in FIG. 26. This data shows that it is possible to insert an enzyme into the FliC sandwich and retain activity. The FliC/Lipase fusion protein forms a very stable complex within the B halodurans cell wall with lipase activity available to the cell surface. Enzyme activity was shown to be relatively strong and sustained over a long period of time. Very little enzyme activity was detected in the supernatant, both favorable characteristics for biotransformation.

Example 9

Immunogenic Peptide as a Fusion with Flagellin Protein

Adjuvants have the ability to stimulate innate immunity and in turn activate the adaptive immune response. It has already been established that flagellin induces an inflammatory response through the activation of APC's (see above). An example is the successful creation and presentation of a flagellin enhanced green fluorescent protein (EGFP) fusion protein. The flagellin-EGFP fusion was capable of stimulating APC's and also specific anti EGFP T-cell responses. EGFP alone was unable to stimulate neither APC's nor specific T-cell responses (Cuadros et al., 2004, Inf. Immun. Vol 72, 2810-2816, McSorley et al., 2002, J. Immunol. Vol 169, 3914-3919). Other peptides inserted into the flagellin which induced an immune response include Cholera toxin subunit B, Hepatitus B epitopes, *Streptococcus pyogenes* M protein epitope, HIV epitopes (gp 41, gp120), influenza A hemagglutinin epitope and various cell surface antigens from *Plasmodium* sp., Rotavirus, *Corynebacterium diphtheriae* and Meningococcal outer membrane protein (Stocker and Newton, 1994, Intern. Rev. Immunol. Vol 2, 167-178). Newton et al., (1995) Res. Microbiol. 146: 203-216.

A number of embodiments of the invention have been described. Nevertheless, it will be understood that various modifications may be made without departing from the spirit and scope of the invention. Accordingly, other embodiments are within the scope of the following claims.

What is claimed is:

1. A fusion protein comprising:
   all or part of a *Bacillus halodurans* flagellin protein, wherein the part of the flagellin protein comprises the N-terminal and C-terminal conserved regions of the flagellin protein; and
   a heterologous polypeptide sequence within, or replacing, the variable region of the flagellin protein,
   wherein the fusion protein is encoded by a nucleic acid sequence operably linked to a transcriptional regulatory element (TRE) which is a $\sigma^D$ promoter.

2. The fusion protein of claim 1, wherein the heterologous polypeptide is a polypeptide having the ability to bind to a metal ion.

3. The fusion protein of claim 2, wherein the metal ion is selected from the group consisting of nickel, copper, cadmium, platinum, palladium, titanium, silver, and gold.

4. The fusion protein of claim 1, wherein the heterologous polypeptide is a polyhistidine sequence.

5. The fusion protein of claim 4, wherein the polyhistidine sequence comprises six histidine residues.

6. The fusion protein of claim 1, wherein the heterologous polypeptide is an enzyme or a functional fragment of an enzyme.

7. The fusion protein of claim 6, wherein the enzyme is a lipase enzyme.

8. The fusion protein of claim 7, wherein the lipase enzyme is *G. thermoleovorans* lipase A.

9. The fusion protein of claim 6, wherein the enzyme is a hydrolytic enzyme.

10. The fusion protein of claim 6, wherein the enzyme is selected from the group consisting of amylases, proteases, esterases, and cellulases.

11. The fusion protein of claim 1, wherein the heterologous polypeptide is an immunogen.

12. The fusion protein of claim 1, further comprising one to fifteen linker residues N-terminal of the N-terminus of the heterologous polypeptide.

13. The fusion protein of claim 1, further comprising one to fifteen linker residues C-terminal of the C-terminus of the heterologous polypeptide.

14. The fusion protein of claim 1, further comprising cleavable sites N-terminal of the N-terminus of the heterologous polypeptide and C-terminal of the C-terminus of the heterologous polypeptide.

15. A composition comprising the fusion protein of claim 1.

16. The composition of claim 15, wherein the heterologous polypeptide is an immunogen.

17. A nucleic acid encoding the fusion protein of claim 1 operably linked to a transcriptional regulatory element (TRE) which is a $\sigma^D$ promoter.

18. A vector comprising a nucleic acid sequence encoding the fusion protein of claim 1 operably linked to a transcriptional regulatory element (TRE) which is a $\sigma^D$ promoter.

19. A kit comprising the expression vector of claim 18.

20. The kit of claim 19, further comprising at least one restriction enzyme.

21. The kit of claim 19, further comprising a host cell, wherein the host cell is a cell in which the expression vector is capable of replicating.

22. The kit of claim 19, further comprising instructions for inserting a nucleic acid sequence encoding a heterologous polypeptide into the DNA construct.

23. An isolated cell comprising the vector of claim 18.

24. The cell of claim 23, wherein the cell is a prokaryotic cell.

25. The cell of claim 24, wherein the cell is a bacterial cell.

26. The cell of claim 25, wherein the cell is a Gram positive bacterial cell.

27. The cell of claim 26, wherein the cell is of the *Bacillus* genus.

28. The cell of claim 27, wherein the cell is of the *B halodurans* species.

29. The cell of claim 28, wherein the cell is of the strain BhFC04 deposited under Accession Number 41357 at the NCIMB on 28 Nov. 2005.

30. A method of making a fusion protein, the method comprising culturing the cell of claim 23 and obtaining the fusion protein from the culture.

31. A method of producing polypeptides attached to the cell surface of *B. halodurans*, the method comprising growing a *B. halodurans* host cell which has a nucleic acid encoding the fusion protein of claim 1 operably linked to a transcriptional regulatory element (TRE) which is a $\sigma^D$ promoter, and allowing production of said polypeptides to take place.

32. A method of removing one or more metal ions from a liquid, the method comprising:

contacting a liquid comprising one or more metal ions with the fusion protein of claim 1, wherein the heterologous polypeptide is a polypeptide that binds to one more metal ions, and removing one or more ions from the liquid.

33. The method of claim 32, wherein the fusion protein is expressed on a bacterial cell surface.

34. The method of claim 32, wherein the fusion protein is a cell-surface polypeptide.

35. A method of isolating one or more metal ions from a liquid containing the one or more metal ions, the method comprising:

contacting a liquid comprising one or more metal ions with the fusion protein of claim 1, wherein the heterologous polypeptide is a polypeptide that binds to the one or more metal ions, the contacting resulting in binding of the one more metal ions to the fusion protein; and separating the one or more metal ions from the fusion protein.

36. A method of converting a substrate to a product, the method comprising:

contacting an enzyme substrate with the fusion protein of claim 1, wherein the heterologous polypeptide is the enzyme or a functional fragment of the enzyme, wherein the substrate is converted to a product.

37. A method for generating an immune response in a mammalian subject, said method comprising administering the fusion protein of claim 1 to said mammalian subject, wherein the heterologous polypeptide is an immunogen, and wherein an immune response is generated in said mammalian subject.

38. The method of claim 37, wherein the mammalian subject is a human.

39. A method for generating an immune response in a subject, said method comprising administering the fusion protein of claim 1 to said subject, wherein the heterologous polypeptide is an immunogen, and wherein an immune response is generated in said subject.

* * * * *